US008450371B2

(12) United States Patent
Kuo et al.

(10) Patent No.: US 8,450,371 B2
(45) Date of Patent: *May 28, 2013

(54) 4-((PHENOXYALKYL)THIO)-PHENOXYACETIC ACIDS AND ANALOGS

(75) Inventors: Gee-Hong Kuo, Scotch Plains, NJ (US); Rui Zhang, Belle Mead, NJ (US); Aihua Wang, Jamison, PA (US); Alan R. DeAngelis, Pennington, NJ (US)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/597,316

(22) Filed: Aug. 29, 2012

(65) Prior Publication Data

US 2012/0322875 A1    Dec. 20, 2012

Related U.S. Application Data

(60) Continuation of application No. 13/207,809, filed on Aug. 11, 2011, now Pat. No. 8,258,177, which is a continuation of application No. 12/549,431, filed on Aug. 28, 2009, now Pat. No. 8,008,513, which is a division of application No. 10/942,563, filed on Sep. 16, 2004, now Pat. No. 7,598,292.

(60) Provisional application No. 60/504,089, filed on Sep. 19, 2003.

(51) Int. Cl.
*A61K 31/192* (2006.01)
*A61P 9/00* (2006.01)
*A61P 3/04* (2006.01)
*A61P 3/06* (2006.01)

(52) U.S. Cl.
USPC ........................................................ 514/571

(58) Field of Classification Search
USPC ........................................................ 514/571
See application file for complete search history.

(56) References Cited

U.S. PATENT DOCUMENTS

| | | | |
|---|---|---|---|
| 4,125,732 A | 11/1978 | McEnvoy et al. | |
| 4,820,867 A | 4/1989 | Belanger et al. | |
| 5,726,165 A | 3/1998 | Beeley et al. | |
| 7,301,050 B2 | 11/2007 | Kuo et al. | |
| 7,425,649 B2 | 9/2008 | Kuo et al. | |
| 7,598,416 B2 | 10/2009 | Kuo et al. | |
| 7,635,718 B2 | 12/2009 | Kuo et al. | |
| 7,709,682 B2 | 5/2010 | Abdel-Magid et al. | |

| | | |
|---|---|---|
| 2005/0124698 A1 | 6/2005 | Kuo et al. |
| 2006/0058393 A1 | 3/2006 | DeAngelis et al. |
| 2006/0257987 A1 | 11/2006 | Gonzalez Valcarcel |
| 2007/0060649 A1 | 3/2007 | Abdel-Magid et al. |
| 2009/0318332 A1 | 12/2009 | Kuo et al. |

FOREIGN PATENT DOCUMENTS

| | | |
|---|---|---|
| EP | 0056172 A2 | 7/1982 |
| EP | 0092136 A | 10/1983 |
| EP | 0106565 A | 4/1984 |
| JP | 61-268651 A | 11/1986 |
| WO | WO 97/27847 A1 | 8/1997 |
| WO | WO 01/00603 A1 | 1/2001 |
| WO | WO 03/011807 A1 | 2/2003 |
| WO | WO 03/074495 A2 | 9/2003 |
| WO | WO 2005/019151 | 3/2005 |

OTHER PUBLICATIONS

Auboeuf et al., "Tissue Distribution and Quantification of the Expression of mRNAs of Peroxisome Proliferator-Activated Receptors and Liver X Receptor-α in Humans.", Diabetes, 1997, vol. 46, pp. 1319-1327.
Berge et al., "Pharmaceutical Salts.", J. Pharm.Sci., 1977, vol. 66(1), pp. 1-19.
Boden, G., "Free Fatty Acids, Insulin Resistance, and Type 2 Diabetes Mellitus.", Proceedings of the Association of American Physicians, 1991, vol. 111(3), pp. 241-248.
Braissant et al., "Differential Expression of Peroxisome Proliferator-Activated Receptors (PPARs): Tissue Distribution of PPAR-α, -62, and -γ in the Adult Rat*.", Endocrinology, 1996, vol. 137(1), pp. 354-366.
Lawn et al., "The Tangier disease gene product ABC1 controls the cellular apolipoprotein-mediated lipid removal pathway.", J. Clin. Investigation, 1999, vol. 104(8), pp. R25-R31.
Leibowitz et al., "Activation of PPARδ alters lipin metabolism in db/db mice.", FEBS Lett., 2000, vol. 473(3), pp. 333-336.
Oliver et al., "A selective peroxisome proliferator-activated receptor δ agonist promotes reverse cholesterol transport.", PNAS, 2001, vol. 98(9), pp. 5306-5311, USA.
Shi et al., "The peroxisome proliferator-activated receptor ,an integrator of transcriptional repression and nuclear receptor signaling.", Proc Natl. Acad. Sci., 2002, vol. 99(5), pp. 2613-2618, USA.
Sznaidman et al., "Novel Selective Small Molecule Agonists for Peroxisome Proliferator-Activated Receptor δ (PPARδ)-Synthesis and Biological Activity.", Bioorganic & Medicinal Chemistry Letters, 2003, vol. 13. pp. 1517-1521.
Richard B. Silverman, The Organic Chemistry of Drug Design and Drug Action, 1992, pp. 15-20.
International Search Report , International Application No. PCT/US2004/030188, Date of Mailing of International Search Report, Mar. 4, 2005.
Written Opinion, International Application No. PCT/US2004/030188. Date of Mailing of Written Opinion, Mar. 4, 2005.

*Primary Examiner* — Kamal Saeed

(57) ABSTRACT

The invention features 4-((phenoxyalkyl)thio)-phenoxyacetic acids and analogs, compositions containing them, and methods of using them as PPAR delta modulators to treat or inhibit the progression of, for example, dyslipidemia.

10 Claims, No Drawings

4-((PHENOXYALKYL)THIO)-PHENOXYACETIC ACIDS AND ANALOGS

CROSS-REFERENCE TO RELATED APPLICATIONS

This application is a continuation of U.S. patent application Ser. No. 13/207,809, filed Aug. 11, 2011 which is a continuation of U.S. patent application Ser. No. 12/549,431, filed Aug. 28, 2009, now U.S. Pat. No. 8,008,513, which is a divisional application of U.S. application Ser. No. 10/942,563, filed Sep. 16, 2004, now U.S. Pat. No. 7,598,292, which claims priority to U.S. Provisional Patent Application No. 60/504,089, filed Sep. 19, 2003, the disclosures of which are hereby incorporated by reference in their entireties.

STATEMENT REGARDING FEDERALLY SPONSORED RESEARCH OR DEVELOPMENT

The research and development of the invention described below was not federally sponsored.

BACKGROUND OF THE INVENTION

Cardiovascular disease (CVD) is prevalent in the world and is often associated with other disease states such as diabetes and obesity. Many population studies have attempted to identify the risk factors for CVD; of these, high plasma levels of low density lipoprotein cholesterol (LDL-C), high plasma levels of triglycerides (~200 mg/dl), and low levels of high density lipoprotein cholesterol (HDL-C) are considered to be among the most important. Currently, there are few therapies targeting low HDL-C and triglycerides.

The peroxisome proliferator-activated receptors (PPARs) are metabolic sensors regulating the expression of genes involved in glucose and lipid homeostasis. Agonists of the PPARα subtype, such as LOPID® (gemfibrozil) and TRICOR® (fenofibrate), and agonists of the PPARγ subtype, such as AVANDIA® (rosiglitazone maleate), are used for the treatment of dyslipidemia and diabetes, respectively. Another member of this nuclear receptor family, the peroxisome proliferator-activated receptor delta (PPAR delta or PPARδ) is also a necessary transcription factor reported to be involved in regulating genes involved in lipid metabolism and energy expenditure. PPAR delta has been shown to act as a "gateway" receptor modulating the expression of the other PPARs (Shi et al., 2002, Proc Natl. Acad. Sci USA, 99(5): 2613-2618). Each receptor subtype has a distinct tissue distribution: 1) PPARα shows the highest expression in liver, 2) PPARγ appears primarily in adipose tissue, and 3) PPAR has the widest distribution—ubiquitously in adult rat (Braissant et al., 1996, Endocrinology 137(1): 354-366) and in all the human tissues tested to date, including liver, kidney, abdominal adipose and skeletal muscle (Auboeuf et al., 1997, Diabetes 46(8):1319-1327).

Recently, potent ligands for PPARδ have been published, providing a better understanding of its function in lipid metabolism. The main effect of these compounds in db/db mice (Leibowitz et al., 2000, FEBS Lett. 473(3):333-336) and obese rhesus monkeys (Oliver et al., 2001, Proc. Natl. Acad. Sci. USA 98(9):5306-5311) was an increase in high density lipoprotein cholesterol (HDL-C) and a decrease in triglycerides, with little effect on glucose (although insulin levels were decreased in monkeys). HDL-C removes cholesterol from peripheral cells through a process called reverse cholesterol transport. The first and rate-limiting step, a transfer of cellular cholesterol and phospholipids to the apolipoprotein A-I component of HDL, is mediated by the ATP binding cassette transporter A1 (ABCA1) (Lawn et al., 1999, J. Clin. Investigation 104(8): R25-R31). PPARδ activation has been shown to increase HDL-C level through transcriptional regulation of ABCA1 (Oliver et al., 2001, Proc. Natl. Acad. Sci. USA 98(9): 5306-5311). Through induction of ABCA1 mRNA expression in macrophages, PPAR agonists may increase HDL-C levels in patients and remove excess cholesterol from lipid-laden macrophages, thereby inhibiting the development of atherosclerotic lesions. Existing therapy for hypercholesterolemia includes the statin drugs, which decrease LDL-C but show little effect on HDL-C, and the fibrates, the PPARα agonists that have low potency and induce only modest HDL-C elevation. In addition, like the fibrates, PPARδ agonists may also reduce triglycerides, an additional risk factor for cardiovascular disease and diabetes. Elevated free fatty acid level has been shown to contribute to insulin resistance and progression of diabetes (Boden, G. PROCEEDINGS OF THE ASSOCIATION OF AMERICAN PHYSICIANS (1999 May-June), 111(3), 241-8).

Examples of known PPAR delta agonists variously useful for hyperlipidemia, diabetes, or atherosclerosis include L-165041 (Leibowitz et al., 2000) and GW501516 (Oliver et al., Proceedings of the National Academy of Sciences of the United States of America (2001), 98(9), 5306-5311). Treatment of differentiated THP-1 monocytes with GW501516 induced ABCA1 mRNA expression and enhanced cholesterol efflux from these cells.

SUMMARY OF THE INVENTION

The invention features compounds of Formula (I) below:

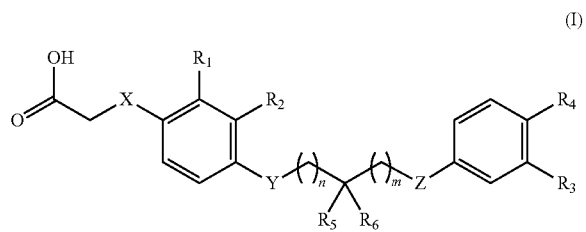

(I)

wherein
X is selected from a covalent bond, S, and O;
Y is S or O;
Z is O or $CH_2$, provided when Y is O, Z is O;
$R_1$ and $R_2$ are independently selected from H, $C_{1-3}$ alkyl, $C_{1-3}$ alkoxy, halo, and $NR_aR_b$ wherein $R_a$ and $R_b$ are independently H or $C_{1-3}$ alkyl;
$R_3$ and $R_4$ are independently selected from H, halo, cyano, $C_{1-5}$ alkyl, hydroxy, $C_{2-4}$ acyl, $C_{1-4}$ alkoxy, and $NR_cR_d$ wherein $R_c$ and $R_d$ are independently H or $C_{1-3}$ alkyl, provided that $R_3$ and $R_4$ are not both H;
$R_5$ and $R_6$ are independently selected from halo, phenyl, $C_{1-9}$ alkyl, $C_{1-6}$ alkoxy, $C_{2-9}$ alkenyl, $C_{2-9}$ alkenyloxy, $C_{3-7}$ cycloalkyl, $C_{3-7}$ cycloalkoxy, $C_{3-7}$cycloalkyl-$C_{1-7}$alkyl, $C_{3-7}$cycloalkyl-$C_{1-7}$alkxoy, $C_{3-7}$cycloalkyloxy-$C_{1-6}$alkyl, and $C_{3-7}$cycloalkyloxy-$C_{1-7}$alkoxy, or $R_5$ and $R_6$ together form $C_{1-9}$ alkylidenyl or $C_{3-9}$ alkenylidenyl, or $R_5$,
$R_6$ and the carbon atom to which they attach together form $C_{3-7}$ cycloalkyl or 5- or 6-membered heterocycle;
n is 0, 1 or 2; and
m is 0, 1 or 2;

or a pharmaceutically acceptable salt thereof.

The invention also features compositions that include one or more compounds of Formula (I) and a pharmaceutical carrier or excipient.

These compositions and the methods below may further include additional pharmaceutically active agents, such as lipid-lowering agents or blood-pressure lowering agents, or both.

Another aspect of the invention includes methods of using the disclosed compounds or compositions in various methods for treating, preventing, or inhibiting the progression of, a condition directly or indirectly mediated by PPAR delta. Said condition includes, but is not limited to, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity.

One embodiment of the present invention is a method for treating a PPAR-delta mediated condition, said method comprising administering to a patient in need of treatment a pharmaceutically effective amount of a compound or composition described herein.

Another embodiment of the present invention is a method for inhibiting the onset and/or inhibiting the progression of a PPAR-delta mediated condition, said method comprising administering to a patient in need of treatment a pharmaceutically effective amount of a compound or composition described herein.

Examples of conditions that can be treated with a PPAR delta-agonist include, without limitation, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity. Dyslipidemia includes hypertriglyceridemia, and mixed hyperlipidemia. For example, dyslipidemia (including hyperlipidemia) may be one or more of the following conditions: low HDL (<35 or 40 mg/dl), high triglycerides (>200 mg/dl), and high LDL (>150 mg/dl).

Additional features and advantages of the invention will become apparent from the detailed discussion, examples, and claims below.

DETAILED DESCRIPTION

The invention features compositions containing compounds of Formula (I) in the above Summary section, and methods of using them.

Preferred compounds of the invention are potent PPAR delta agonists that have at least one and preferably two or three of the following characteristics when administered to patients with hypercholesterolemia, hypertriglyceridemia, low-HDL-C, obesity, diabetes and/or Metabolic X Syndrome: 1) increasing HDL-C level, 2) lowering triglycerides, 3) lowering free fatty acids, and 4) decreasing insulin levels. Improvement in HDL-C and triglyceride levels is beneficial for cardiovascular health. In addition, decreased level of triglycerides and free fatty acids contributes to reduce obesity and ameliorate or prevent diabetes.

PPAR delta, being ubiquitously expressed, can act as a gateway receptor that regulates the expression/activity of other nuclear receptors such as other PPARs. For instance, PPAR delta has been shown to block PPARγ-mediated adipogenesis and acyl-CoA oxidase expression; it has also been shown to be associated with the nuclear receptor corepressors SMRT (silencing mediator for retinoid and thyroid hormone receptors), SHARP (SMART and histone deacetylase-associated repressor protein), and HDACs (histone deacetylase). Thus, conditions directly mediated by these nuclear receptors, such as obesity and type II diabetes, can be indirectly mediated by PPAR delta (See, for example, Shi et al., 2002, Proc Natl. Acad. Sci USA, 99(5): 2613-2618).

Some aspects of the invention relate to treating hypertriglyceridemia, raising levels of HDL, lowering levels of LDL, and/or lowering total cholesterol. Preferably, the methods of treatment are associated with improvements in the extent, duration, or degree of side effects, such as edema, normally associated with other existing therapies.

The invention is further described below. The specification is arranged as follows: A) Terms; B) Compounds; C) Synthesis; D) Formulation and Administration; E) Use; F) Biological Examples; G) Other Embodiments; and claims.

A. TERMS

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation, prevention, treatment, or the delay of the onset or progression of the symptoms of the disease or disorder being treated.

Conditions directly or indirectly mediated by PPAR delta include, but are not limited to, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity.

For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

Unless otherwise noted, as used herein and whether used alone or as part of a substituent group, "alkyl" and "alkoxy" include straight and branched chains having 1 to 8 carbon atoms, such as $C_{1-6}$, $C_{1-4}$, $C_{3-8}$, $C_{2-5}$, or any other range, and unless otherwise noted, include both substituted and unsubstituted moieties. For example, $C_{1-6}$alkyl radicals include methyl, ethyl, n-propyl, isopropyl, n-butyl, isobutyl, sec-butyl, t-butyl, n-pentyl, 3-(2-methyl)butyl, 2-pentyl, 2-methyl butyl, neopentyl, n-hexyl, 2-hexyl and 2-methylpentyl. Alkoxy radicals are formed from the previously described straight or branched chain alkyl groups. "Alkyl" and "alkoxy" include unsubstituted or substituted moieties with one or more substitutions, such as between 1 and 5, 1 and 3, or 2 and 4 substituents. The substituents may be the same (dihydroxy, dimethyl), similar (chloro, fluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, trifluoromethyl, and 3-iodocyclopentyl), hydroxyalkyl (such as hydroxymethyl, hydroxyethyl, 2-hydroxypropyl), aminoalkyl (such as aminomethyl, 2-aminoethyl, 3-aminopropyl, and 2-aminopropyl), alkoxylalkyl, nitroalkyl, alkylalkyl, cyanoalkyl, phenylalkyl, heteroarylalkyl, heterocyclylalkyl, phenoxyalkyl, heteroaryloxyalkyl (such as 2-pyridyloxyalkyl), heterocyclyloxy-alkyl (such as 2-tetrahydropyranoxyalkyl), thioalkylalkyl (such as MeS-alkyl), thiophenylalkyl (such as phS-alkyl), carboxylalkyl, and so on. A di($C_{1-3}$ alkyl) amino group includes independently selected alkyl groups, to form, for example, methylpropylamino and isopropylmethylamino, in addition dialkylamino groups having two of the same alkyl group such as dimethyl amino or diethylamino.

The term "alkenyl" includes optionally substituted straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention. "Alkenyl" may be substituted with one or more substitutions including, but not limited to, cyanoalkenyl, and thioalkenyl.

The term "alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

The term "Ac" as used herein, whether used alone or as part of a substituent group, means acetyl ($CH_3CO$—). The term "acyl" as used herein, referes to a substituent that has a carbonyl group (C=O) and one or more alkyl or alkylene groups. For example, $C_{2-4}$ acyl includes without limitation, acetyl, $CH_3CH_2$—(C=O)—$CH_2$—, and $CH_3CH_2CH_2$(C=O)—.

The term "halogen" or "halo" shall include iodo, bromo, chloro and fluoro.

The terms "aryl" or "Ar" as used herein refer to an unsubstituted or substituted aromatic hydrocarbon ring system such as phenyl and naphthyl. When the Ar or aryl group is substituted, it may have one to three substituents which are independently selected from $C_1$-$C_8$ alkyl, $C_1$-$C_8$ alkoxy, fluorinated $C_1$-$C_8$ alkyl (e.g., trifluoromethyl), fluorinated $C_1$-$C_8$ alkoxy (e.g., trifluoromethoxy), halogen, cyano, $C_1$-$C_8$ alkylcarbonyl such as acetyl, carboxyl, hydroxy, amino, nitro, $C_1$-$C_4$ alkylamino (i.e., —NH—$C_1$-$C_4$ alkyl), $C_1$-$C_4$ dialkylamino (i.e., —N—[$C_1$-$C_4$ alkyl]$_2$ wherein the alkyl groups can be the same or different), or unsubstituted, mono-, di- or tri-substituted phenyl wherein the substituents on the phenyl are independently selected from $C_1$-$C_8$ alkyl, $C_1$-$C_8$ alkoxy, fluorinated $C_1$-$C_8$ alkyl, fluorinated $C_1$-$C_8$ alkoxy, halogen, cyano, acetyl, carboxyl, hydroxy, amino, nitro, alkylamino, dialkylamino or five or six membered heteroaryl having 1-3 heteroatoms selected from N, O and S.

The term "heteroaryl" as used herein represents a stable, unsubsituted or substituted five or six membered monocyclic or bicyclic aromatic ring system which consists of carbon atoms and from one to three heteroatoms selected from N, O and S. The heteroaryl group may be attached at any heteroatom or carbon atom which results in the creation of a stable structure. Examples of heteroaryl groups include, but are not limited to, benzimidazolyl, benzisoxazolyl, benzofuranyl, benzopyrazolyl, benzothiadiazolyl, benzothiazolyl, benzothienyl, benzotriazolyl, benzoxazolyl, furanyl, furazanyl, furyl, imidazolyl, indazolyl, indolizinyl, indolinyl, indolyl, isobenzofuranyl, isoindolyl, isothiazolyl, isoxazolyl, oxazolyl, purinyl, pyrazinyl, pyrazolyl, pyridazinyl, pyridinyl, pyrimidinyl, pyrrolyl, quinolinyl, quinolyl, thiadiazolyl, thiazolyl, thiophenyl, or triazolyl. When the heteroaryl group is substituted, the heteroaryl group may have one to three substituents including, but not limited to, $C_1$-$C_8$ alkyl, halogen, and aryl.

The term "heterocyclyl" includes optionally substituted nonaromatic rings having carbon atoms and at least one heteroatom (O, S, N) or heteroatom moiety ($SO_2$, CO, CONH, COO) in the ring. A heterocyclyl may be saturated, partially saturated, nonaromatic, or fused. Examples of heterocyclyl include cyclohexylimino, imdazolidinyl, imidazolinyl, morpholinyl, piperazinyl, piperidyl, pyridyl, pyranyl, pyrazolidinyl, pyrazolinyl, pyrrolidinyl, pyrrolinyl, and thienyl.

Unless otherwise indicated, heteroaryl and heterocyclyl may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 5 and 7 ring atoms, or between 5 and 6 ring atoms; there may be between 1 and 5 heteroatoms or heteroatom moieties in the ring, and preferably between 1 and 3, or between 1 and 2 heteroatoms or heteroatom moieties.

Heterocyclyl and heteroaryl also include fused, e.g., bicyclic, rings, such as those optionally fused with an optionally substituted carbocyclic or heterocyclic five- or six-membered aromatic ring. For example, "heteroaryl" includes an optionally substituted six-membered heteroaromatic ring containing 1, 2 or 3 nitrogen atoms fused with an optionally substituted five- or six-membered carbocyclic or heterocyclic aromatic ring. Said heterocyclic five- or six-membered aromatic ring fused with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Where chemical moieties are combined, such as in ethoxymethyl or phenylethyl, the term is described in the direction from the periphery to the connection point of the rest of the molecule. For example, ethoxymethyl is $CH_3CH_2OCH_2$— and phenylethyl is a phenyl group linked by —$CH_2CH_2$— to the rest of the molecule (and not a phenyl group linked to the molecule with a $CH_3CH_2$ group as a substituent on the phenyl.) Where parentheses are used, they indicate a peripheral substitution.

As used herein, the term "composition" is intended to encompass a product comprising the specified ingredients in the specified amounts, as well as any product which results, directly or indirectly, from combinations of the specified ingredients in the specified amounts.

Compounds of the invention are further described in the next section.

B. COMPOUNDS

The present invention features compositions containing and methods of using compounds of Formula (I) as described above. Unless otherwise noted, in Formula (I), each hydrocarbyl (alkyl, alkenyl, alkynyl, cycloalkyl, cycloalkenyl, etc) or heterocarbyl (heterocyclyl, heteroaryl, heteroatom moiety such as sulfonyl, amino, amido, etc.) may be substituted or unsubstituted, for example, "alkyl" includes substituted and unsubstituted alkyl and "heterocyclyl" and "aryl" and "alkoxy" and so on, may also be substituted or unsubstituted. For example, where $R_4$ is "methyl or methoxy", unless otherwise indicated, these terms collectively include: methyl, methoxy, trifluoromethyl, trifluoromethoxy, difluoromethyl, difluoromethoxy, fluoromethyl, fluoromethoxy, chlorodifluoromethyl, chlorodifluoromethoxy, dichlorofluoromethyl, and dichlorofluoromethoxy, and so on.

Examples include those compounds wherein: (a) X is S or O; (b) X is a covalent bond; (c) X is O; (d) Y is O; (e) Y is S; (f) Z is O; (g) Z is CH or $CH_2$; (h) m is 1; (i) m is 2; (k) n is 1; (l) $R_1$ and $R_2$ are independently selected from H, $C_{1-3}$ alkyl, $C_{1-3}$ alkoxy, F, Cl, and Br; (m) $R_1$ and $R_2$ are independently selected from H, methyl, methoxy, F and Cl; (n) $R_3$ and $R_4$ are independently selected from H, halo, cyano, acetyl, $C_{1-2}$ alkyl, and $C_{1-2}$ alkoxy; (o) $R_3$ is independently selected from H, F, Cl, methyl, and methoxy; (p) $R_4$ is independently selected from H, halo, cyano, $C_{1-2}$ alkyl, and $C_{1-2}$ alkoxy; (q) $R_3$ is independently selected from H, halo, cyano, $C_{1-2}$ alkyl, and $C_{1-2}$ alkoxy, and $R_4$ is independently selected from F, Cl, methyl, and methoxy; (r) $R_3$ is selected from methyl, methoxy, H, Cl, Br, I, OH, —$CH(CF_3)_2$, $CF_3$, —$OCF_3$, —$N(CH_3)_2$, —O—$CH_2COOH$, and —$COCH_3$, and $R_4$ is selected from H, Cl, and methyl; (s) $R_5$ and $R_6$ together form $C_{1-9}$ alkylidenyl or $C_{3-9}$ alkenylidenyl, or $R_5$, $R_6$ and the carbon atom to which they attach together form $C_{3-7}$ cycloalkyl; (t) $R_5$ and $R_6$ are independently selected from halo, phenyl, $C_{1-9}$ alkyl, $C_{1-8}$ alkoxy, $C_{2-9}$ alkenyloxy, $C_{3-7}$ cycloalkyl, $C_{3-7}$ cycloalkoxy, $C_{3-7}$cycloalkyl-$C_{1-7}$alkyl, $C_{3-7}$cycloalkyl-$C_{1-7}$alkoxy, $C_{3-7}$cycloalkyloxy-$C_{1-6}$alkyl, and $C_{3-7}$cycloalkyloxy-$C_{1-7}$alkoxy; (u) $R_3$ is selected from H, F, Cl, methyl, and methoxy, and $R_4$ is selected from F, Cl, acetyl, methyl, methoxy, trifluoromethyl, trifluoromethoxy, difluoromethyl, difluoromethoxy, fluoromethyl, fluoromethoxy; (v) $R_1$ is selected from H, $CF_3$, methyl, Cl, and methoxy, and $R_2$ is selected from H, Cl, and methyl; (w) X is O and Y is O; (x) Z is O and Y is O; (y) $R_1$ is selected from H, $CF_3$, methyl, Cl, and methoxy, $R_2$ is selected from H, Cl, and methyl, $R_3$ is selected from H, F, Cl, methyl, and methoxy, and $R_4$ is selected from F, Cl, methyl, and methoxy; (z) X is O, Y is O, $R_3$ is selected from H, F, Cl, methyl, and methoxy, and $R_4$ is selected from F, Cl, methyl, and methoxy; (z2) Z is O, Y is O, $R_3$ is selected from H, F, Cl, methyl, and methoxy, and $R_4$ is selected from F, Cl, methyl, and methoxy; (aa) $R_1$ is selected from H, $CF_3$, methyl, Cl, and methoxy, $R_2$ is selected from H, Cl, and methyl, $R_3$ is selected from H, F, Cl, methyl, and methoxy, $R_4$ is selected from F, Cl, methyl, and methoxy, and $R_5$ and $R_6$ together form $C_{1-9}$ alkylidenyl or $C_{3-9}$ alkenylidenyl, or $R_5$, $R_6$ and the carbon atom to which they attach together form $C_{3-7}$ cycloalkyl; (bb) X is O, Y is O, Z is O, $R_1$ is selected from H, $CF_3$, methyl, Cl, and methoxy, $R_2$ is selected from H, Cl, and methyl, $R_3$ is selected from H, F, Cl, methyl, and methoxy, $R_4$ is selected from F, Cl, methyl, and methoxy, and $R_5$ and $R_6$ are independently selected from halo, phenyl, $C_{1-9}$ alkyl, $C_{1-8}$ alkoxy, $C_{2-9}$ alkenyl, $C_{2-9}$ alkenyloxy, $C_{3-7}$ cycloalkyl, $C_{3-7}$ cycloalkoxy, $C_{3-7}$cycloalkyl-$C_{1-7}$alkyl, $C_{3-7}$cycloalkyl-$C_{1-7}$alkoxy, $C_{3-7}$cycloalkyloxy-$C_{1-6}$alkyl, and $C_{3-7}$cycloalkyloxy-$C_{1-7}$alkoxy; (cc) X is O, Y is O, Z is O, $R_1$ is selected from H, $CF_3$, methyl, Cl, and methoxy, $R_2$ is selected from H, Cl, and methyl, $R_3$ is selected from H, F, Cl, methyl, and methoxy, and $R_4$ is selected from F, Cl, methyl, and methoxy; (dd) X is O, Y is O, Z is O, $R_1$ is selected from H, $CF_3$, methyl, Cl, and methoxy, $R_2$ is selected from H, Cl, and methyl, $R_3$ is selected from H, F, Cl, methyl, and methoxy, $R_4$ is selected from F, Cl, methyl, and methoxy, and $R_5$ and $R_6$ together form $C_{1-9}$ alkylidenyl or $C_{3-9}$ alkenylidenyl, or $R_5$, $R_6$ and the carbon atom to which they attach together form $C_{3-7}$ cycloalkyl; (ee) X is O, Y is O, Z is O, $R_1$ is selected from H, $CF_3$, methyl, Cl, and methoxy, $R_2$ is selected from H, Cl, and methyl, $R_3$ is selected from H, F, Cl, methyl, and methoxy, $R_4$ is selected from F, Cl, methyl, and methoxy, and $R_5$ and $R_6$ are independently selected from halo, phenyl, $C_{1-9}$ alkyl, $C_{1-8}$ alkoxy, $C_{2-9}$ alkenyl, $C_{2-9}$ alkenyloxy, $C_{3-7}$ cycloalkyl, $C_{3-7}$ cycloalkoxy, $C_{3-7}$cycloalkyl-$C_{1-7}$alkoxy, $C_{3-7}$cycloalkyloxy-$C_{1-6}$alkyl, and $C_{3-7}$cycloalkyloxy-$C_{1-7}$alkoxy; (ff) X is O, Y is O or S, Z is O, $R_1$ is selected from H, $CF_3$, methyl, Cl, and methoxy, $R_2$ is selected from H, Cl, and methyl, $R_3$ is selected from H, F, Cl, methyl, and methoxy, $R_4$ is selected from F, Cl, methyl, and methoxy, m is 1, and n is 1; (gg) X is O, Y is O or S, Z is O, $R_1$ is selected from H, $CF_3$, methyl, Cl, and methoxy, $R_2$ is selected from H, Cl, and methyl, $R_3$ is selected from H, F, Cl, methyl, and methoxy, $R_4$ is selected from F, Cl, methyl, and methoxy, m is 1, n is 1, and $R_5$ and $R_6$ are independently selected from halo, phenyl, $C_{1-9}$ alkyl, $C_{1-8}$ alkoxy, $C_{2-9}$ alkenyl, $C_{2-9}$ alkenyloxy, $C_{3-7}$ cycloalkyl, $C_{3-7}$ cycloalkoxy, $C_{3-7}$cycloalkyl-$C_{1-7}$alkyl, $C_{3-7}$cycloalkyl-$C_{1-7}$alkxoy, $C_{3-7}$cycloalkyloxy-$C_{1-6}$alkyl, and $C_{3-7}$cycloalkyloxy-$C_{1-7}$alkoxy; or combinations of the above.

Compounds of the present invention further can be selected from:

{2-Methyl-4-[2-(4-trifluoromethyl-phenoxymethyl)-allyl-sulfanyl]phenoxy}-acetic acid;

(2-Methyl-4-{2-[2-(4-trifluoromethyl-phenyl)-ethyl]-allyl-sulfanyl}-phenoxy)-acetic acid;

{2-Methyl-4-[2-(4-trifluoromethoxy-phenoxymethyl)-allyl-sulfanyl]-phenoxy}-acetic acid;

{2-Chloro-4-[2-(4-trifluoromethyl-phenoxymethyl)-allyl-sulfanyl]-phenoxy}-acetic acid;

{2-Methyl-4-[3-methyl-2-(4-trifluoromethyl-phenoxymethyl)-but-2-enylsulfanyl]-phenoxy}-acetic acid;

{4-[3,3-Difluoro-2-(4-trifluoromethyl-phenoxymethyl)-allylsulfanyl]-2-methyl-phenoxy}-acetic acid;

{3-Chloro-4-[2-(4-trifluoromethyl-phenoxymethyl)-allyl-sulfanyl]-phenyl}-acetic acid;

{2-Methyl-4-[1-(4-trifluoromethyl-phenoxymethyl)-cyclopropylmethylsulfanyl]-phenoxy}-acetic acid;

{2-Methyl-4-[2-propyl-2-(4-trifluoromethyl-phenoxymethyl)-pentylsulfanyl]-phenoxy}-acetic acid;

{4-[2-(4-Acetyl-3-hydroxy-2-propyl-phenoxymethyl)-allylsulfanyl]-2-methyl-phenoxy}-acetic acid;

{4-[2-(4-Chloro-phenoxymethyl)-allylsulfanyl]-2-methyl-phenoxy}-acetic acid;

{4-[2-(3,4-Dichloro-phenoxymethyl)-allylsulfanyl]-2-methyl-phenoxy}-acetic acid;

{4-[2-(2,4-Dichloro-phenoxymethyl)-allylsulfanyl]-2-methyl-phenoxy}-acetic acid;

{4-[3-Cyano-2-(4-trifluoromethyl-phenoxymethyl)-allyl-sulfanyl]-2-methyl-phenoxy}-acetic acid;

{2-Methyl-4-[3-phenyl-2-(4-trifluoromethyl-phenoxymethyl)-allyl)sulfanyl]-phenoxy}-acetic acid;
{2-Methyl-4-[3-naphthalen-1-yl-2-(4-trifluoromethyl-phenoxymethyl)-allylsulfanyl]-phenoxy}-acetic acid;
{4-[2,2-Difluoro-3-(4-trifluoromethyl-phenoxy)-propylsulfanyl]-2-methyl-phenoxy}-acetic acid;
{2-Methyl-4-[2-(4-trifluoromethyl-phenoxymethyl)-[1,3]dioxan-2-ylmethylsulfanyl]-phenoxy}-acetic acid;
{4-[2,2-Dimethyl-4-(4-trifluoromethyl-phenoxymethyl)-[1,3]dioxolan-4-ylmethylsulfanyl]-2-methyl-phenoxy}-acetic acid;
[2-Methyl-4-(2-phenoxymethyl-allylsulfanyl)-phenoxy]-acetic acid;
{4-[2-(4-Chloro-3-trifluoromethyl-phenoxymethyl)-allylsulfanyl]-2-methyl-phenoxy}-acetic acid;
{4-[2-(4-Methoxy-phenoxymethyl)-allylsulfanyl]-2-methyl-phenoxy}-acetic acid;
{4-[2-(4-Dimethylamino-phenoxymethyl)-allylsulfanyl]-2-methyl-phenoxy}-acetic acid;
{2-Trifluoromethyl-4-[2-(4-trifluoromethyl-phenoxymethyl)-allylsulfanyl]-phenoxy}-acetic acid;
{3-Chloro-4-[2-(4-trifluoromethyl-phenoxymethyl)-allylsulfanyl]-phenoxy}-acetic acid;
{2-Methoxy-4-[2-(4-trifluoromethyl-phenoxymethyl)-allylsulfanyl]-phenoxy}-acetic acid;
{2-Methyl-4-[3-(4-trifluoromethyl-phenoxy)-but-3-enylsulfanyl]-phenoxy}-acetic acid;
{2-Methyl-4-[2-(4-trifluoromethyl-phenoxy)-allylsulfanyl]-phenoxy}-acetic acid;
{4-[2-Hydroxy-2-(4-trifluoromethyl-phenoxymethyl)-butylsulfanyl]-2-methyl-phenoxy}-acetic acid;
{4-[2-(4-tert-Butyl-phenoxymethyl)-allylsulfanyl]-2-methyl-phenoxy}-acetic acid;
{4-[2-(4-Isopropyl-phenoxymethyl)-allylsulfanyl]-2-methyl-phenoxy}-acetic acid;
{2-Chloro-4-[2-(3,4-dichloro-phenoxymethyl)-allylsulfanyl]-phenoxy}-acetic acid;
{2-Chloro-4-[2-(4-trifluoromethoxy-phenoxymethyl)-allylsulfanyl]-phenoxy}-acetic acid;
{4-[2,2-Dimethyl-3-(4-trifluoromethyl-phenoxy)-propylsulfanyl]-2-methyl-phenoxy}-acetic acid;
{2-Chloro-4-[2,2-dimethyl-3-(4-trifluoromethyl-phenoxy)-propyl)sulfanyl]-phenoxy}-acetic acid;
{2-Chloro-4-[1-(4-trifluoromethyl-phenoxymethyl)-cyclopropylmethylsulfanyl]-phenoxy}-acetic acid;
{3-Chloro-4-[2,2-dimethyl-3-(4-trifluoromethyl-phenoxy)-propylsulfanyl]-phenyl}-acetic acid;
{2-Methyl-4-[2-(4-trifluoromethyl-phenoxymethyl)-allylsulfanyl]-phenoxy}-acetic acid;
{3-Chloro-4-[2,2-dimethyl-3-(4-trifluoromethoxy-phenoxy)-propylsulfanyl]-phenyl}-acetic acid; and
{3-Chloro-4-[3-methyl-2-(4-trifluoromethyl-phenoxymethyl)-but-2-enylsulfanyl]-phenyl}-acetic acid.

Further, the following is a compound of the present invention: acetic acid, [2-methyl-4-[[2-[[4-(trifluoromethyl)phenoxy]methyl]-2-propenyl]thio]phenoxy]-.

The present invention also provides compositions containing and methods of using compounds of Formula (I). In particular, the present invention provides compositions containing and methods of using compounds of Formula (I) as exemplified above.

Examples of preferred compounds include those described in Table 1 below.

TABLE 1

| Compound Number | Structure |
| --- | --- |
| 1 | 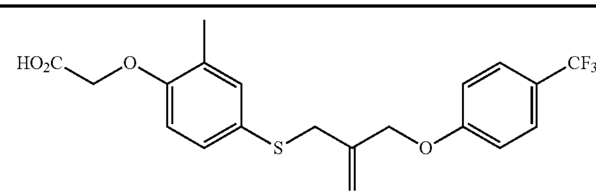 |
| 2 | 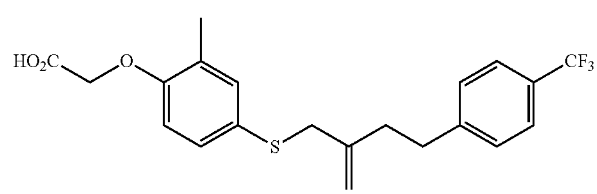 [SMILES: C=C(CCc1ccc(C(F)(F)F)cc1)CSc1ccc(OCC(=O)O)c(C)c1] |
| 3 | 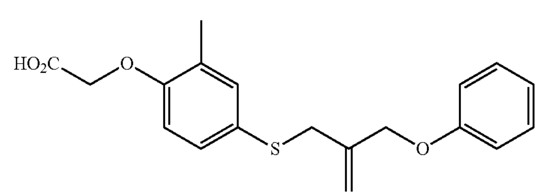 [SMILES: C=C(COc1ccccc1)CSc1ccc(OCC(=O)O)c(C)c1] |
| 4 | 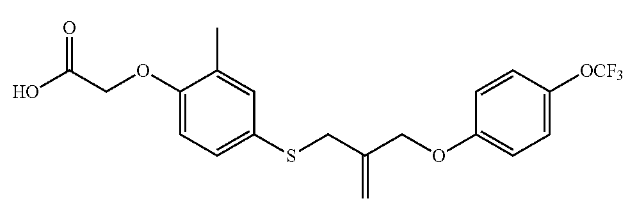 [SMILES: C=C(COc1ccc(OC(F)(F)F)cc1)CSc1ccc(OCC(=O)O)c(C)c1] |

TABLE 1-continued

| Compound Number | Structure |
|---|---|
| 5 | 4-(2-methylphenoxy)acetic acid linked via S-CH2-C(=CH2)-CH2-O to 4-chlorophenyl |
| 6 | 4-(2-methylphenoxy)acetic acid linked via S-CH2-C(=CH2)-CH2-O to 3,4-dichlorophenyl |
| 7 | 4-(2-methylphenoxy)acetic acid linked via S-CH2-C(=CH2)-CH2-O to 2,4-dichlorophenyl |
| 8 | 4-(2-methylphenoxy)acetic acid linked via S-CH2-C(=CH2)-CH2-O to 4-chloro-3-(trifluoromethyl)phenyl |
| 9 | 4-(2-methylphenoxy)acetic acid linked via S-CH2-C(=CH2)-CH2-O to 4-methoxyphenyl |
| 10 | 4-(2-methylphenoxy)acetic acid linked via S-CH2-C(=CH2)-CH2-O to 4-(dimethylamino)phenyl |
| 11 | 4-(2-chlorophenoxy)acetic acid linked via S-CH2-C(=CH2)-CH2-O to 4-(trifluoromethyl)phenyl |
| 12 | 4-(2-(trifluoromethyl)phenoxy)acetic acid linked via S-CH2-C(=CH2)-CH2-O to 4-(trifluoromethyl)phenyl |

TABLE 1-continued

| Compound Number | Structure |
|---|---|
| 13 | 4-[(carboxymethoxy)-2-chlorophenyl] sulfanyl-methyl-2-methylene-3-[(4-trifluoromethylphenoxy)methyl] structure |
| 14 | 4-[(carboxymethoxy)-2-methoxyphenyl] sulfanyl-methyl-2-methylene-3-[(4-trifluoromethylphenoxy)methyl] structure |
| 15 | 4-[(carboxymethoxy)-2-methylphenyl] sulfanyl-methyl-2-(2-methylpropylidene)-3-[(4-trifluoromethylphenoxy)methyl] structure |
| 16 | 4-[(carboxymethoxy)-2-methylphenyl] sulfanyl-methyl-2-(difluoromethylene)-3-[(4-trifluoromethylphenoxy)methyl] structure |
| 17 | 4-[(carboxymethoxy)-2-methylphenyl] sulfanyl-methyl-2-(cyanomethylene)-3-[(4-trifluoromethylphenoxy)methyl] structure |
| 18 | 4-[(carboxymethoxy)-2-methylphenyl] sulfanyl-methyl-2-(phenylmethylene)-3-[(4-trifluoromethylphenoxy)methyl] structure |
| 19 | 4-[(carboxymethoxy)-2-methylphenyl] sulfanyl-methyl-2-(naphthalen-1-ylmethylene)-3-[(4-trifluoromethylphenoxy)methyl] structure |

TABLE 1-continued

| Compound Number | Structure |
| --- | --- |
| 20 | 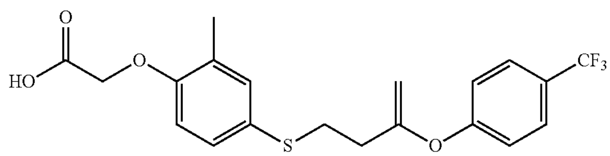 [SMILES: C=C(CCSc1ccc(OCC(=O)O)c(C)c1)Oc1ccc(C(F)(F)F)cc1] |
| 21 | 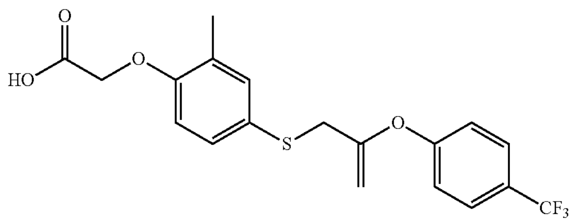 [SMILES: C=C(CSc1ccc(OCC(=O)O)c(C)c1)Oc1ccc(C(F)(F)F)cc1] |
| 22 | 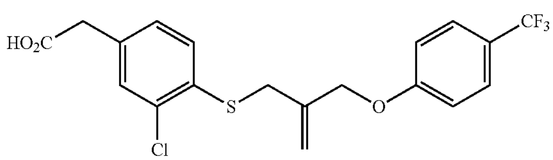 [SMILES: C=C(COc1ccc(C(F)(F)F)cc1)CSc1ccc(CC(=O)O)cc1Cl] |
| 23 | 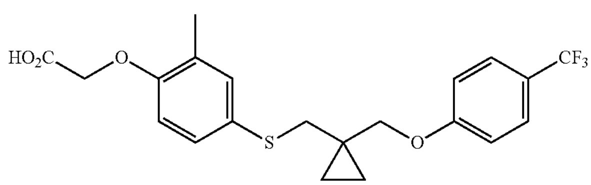 [SMILES: Cc1cc(SCC2(COc3ccc(C(F)(F)F)cc3)CC2)ccc1OCC(=O)O] |
| 24 | 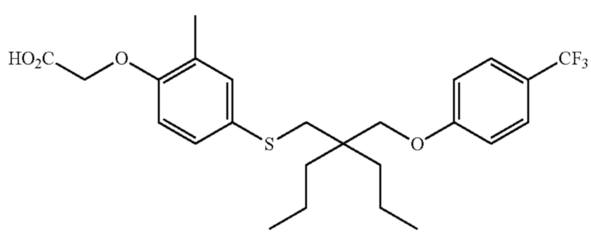 [SMILES: CCCC(CCC)(COc1ccc(C(F)(F)F)cc1)CSc1ccc(OCC(=O)O)c(C)c1] |
| 25 | 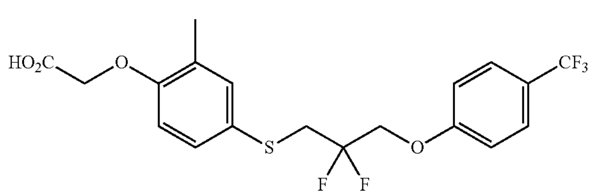 [SMILES: Cc1cc(SCC(F)(F)COc2ccc(C(F)(F)F)cc2)ccc1OCC(=O)O] |
| 26 | 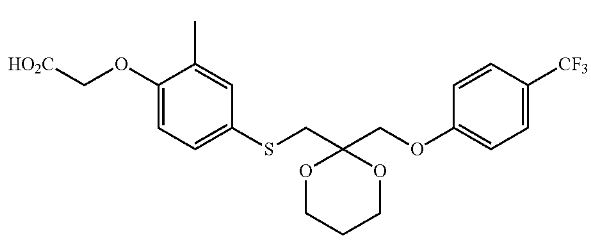 [SMILES: Cc1cc(SCC2(COc3ccc(C(F)(F)F)cc3)OCCCO2)ccc1OCC(=O)O] |

TABLE 1-continued

| Compound Number | Structure |
|---|---|
| 27 | 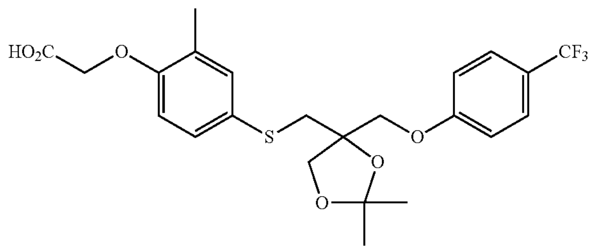 [SMILES: Cc1cc(SCC2(COc3ccc(C(F)(F)F)cc3)COC(C)(C)O2)ccc1OCC(=O)O] |
| 28 | 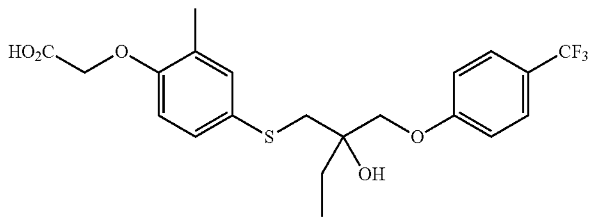 [SMILES: CCC(O)(COc1ccc(C(F)(F)F)cc1)CSc1ccc(OCC(=O)O)c(C)c1] |
| 29 | 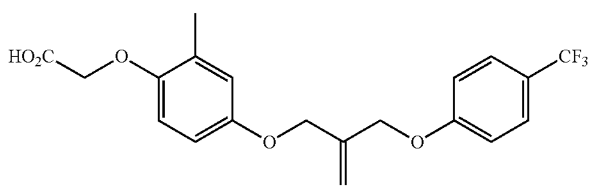 [SMILES: C=C(COc1ccc(C(F)(F)F)cc1)COc1ccc(OCC(=O)O)c(C)c1] |

The present invention also features compounds of Formula (II):

II wherein
X is selected from a covalent bond, S, and O;
Y is S or O;
$R_1$ and $R_2$ are independently selected from H, $C_{1-3}$ alkyl, $C_{1-3}$ alkoxy, halo, and $NR_aR_b$ wherein $R_a$ and $R_b$ are independently H or $C_{1-3}$ alkyl;
$R_3$ and $R_4$ are independently selected from H, halo, cyano, $C_{1-5}$ alkyl, hydroxy, $C_{2-4}$ acyl, $C_{1-4}$ alkoxy, and $NR_cR_d$ wherein $R_c$ and $R_d$ are independently H or $C_{1-3}$ alkyl, provided that $R_3$ and $R_4$ are not both H;
$R_5$ and $R_6$ are independently selected from halo, phenyl, $C_{1-9}$ alkyl, $C_{1-8}$ alkoxy, $C_{2-9}$ alkenyl, $C_{2-9}$ alkenyloxy, $C_{3-7}$ cycloalkyl, $C_{3-7}$ cycloalkoxy, $C_{3-7}$cycloalkyl-$C_{1-7}$alkyl, $C_{3-7}$cycloalkyl-$C_{1-7}$alkoxy, $C_{3-7}$cycloalkyloxy-$C_{1-6}$alkyl, and $C_{3-7}$cycloalkyloxy-$C_{1-7}$alkoxy, or
$R_5$ and $R_6$ together form $C_{1-9}$ alkylidenyl or $C_{3-9}$ alkenylidenyl; or $R_5$,
$R_6$ and the carbon atom to which they are attached together form $C_{3-7}$ cycloalkyl or 5- or 6-membered heterocyclyl;

n is 0, 1 or 2; and
m is 0, 1 or 2;
or a pharmaceutically acceptable salt thereof.

A particular example of such compounds is [2-methyl-4-[[2-[[[4-(trifluoromethyl)phenyl]thio]methyl]-2-propenyl]thio]phenoxy]-acetic acid,

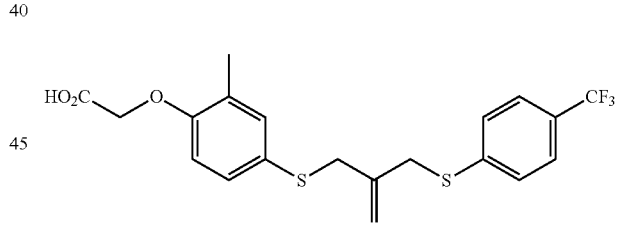

$^1$H NMR (400 MHz, CDCl$_3$) δ 10.64 (brs, 1H), 7.46 (d, J=8.4 Hz, 2H), 7.33 (d, J=8.3 Hz, 2H), 7.17 (s, 1H), 7.12 (dd, J=8.4, 1.5 Hz, 1H), 6.59 (d, J=8.4 Hz, 1H), 4.98 (s, 1H), 4.87 (s, 1H), 4.60 (s, 2H), 3.75 (s, 2H), 3.58 (s, 2H), 2.21 (s, 3H); MS (ES) m/z: 451 (M+Na$^+$); (PPARdleta EC$_{50}$: 80, 45, 38 nM).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

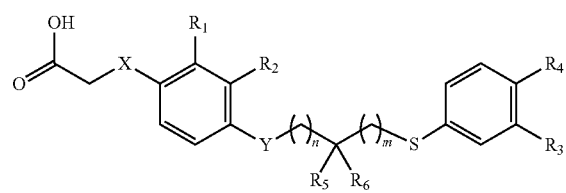

The following are other compounds of interest:

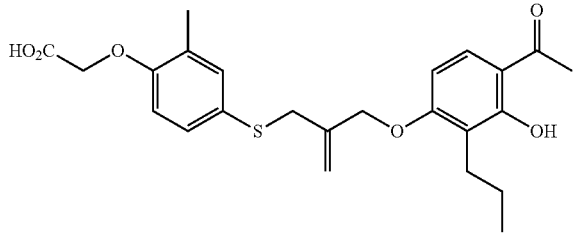 [SMILES: C=C(COc1ccc(C(C)=O)c(O)c1CCC)CSc1ccc(OCC(=O)O)c(C)c1]

{4-[2-(4-acetyl-3-hydroxy-2-propyl-phenoxymethyl)-allylsulfanyl]-2-methyl-phenoxy}-acetic acid $^1$H NMR (300 MHz, CDCl$_3$) δ 7.56 (d, J=9.0 Hz, 1H), 7.20 (s, 1H), 7.17 (d, J=8.4 Hz, 1H), 6.61 (d, J=8.4 Hz, 1H), 6.42 (d, J=9.0 Hz, 1H), 5.15 (s, 1H), 4.99 (s, 1H), 4.67 (s, 2H), 4.61 (s, 2H), 3.57 (s, 2H), 2.63 (t, J=7.6 Hz, 2H), 2.56 (s, 3H), 2.21 (s, 3H), 1.52 (m, 2H), 0.92 (t, J=7.4 Hz, 3H); MS (ES) m/z: 467 (M+Na$^+$); (PPARdleta EC$_{50}$: 13, 18 nM);

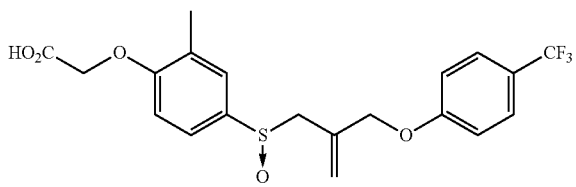 [SMILES: C=C(COc1ccc(C(F)(F)F)cc1)CS(=O)c1ccc(OCC(=O)O)c(C)c1]

[2-methyl-4-[[2-[[4-(trifluoromethyl)phenoxy]methyl]-2-propenyl]sulfinyl]phenoxy]-acetic acid $^1$H NMR (400 MHz, CDCl$_3$) δ 7.52 (m, 3H), 7.35 (s, 1H), 6.93 (d, J=8.6 Hz, 2H), 6.75 (d, J=8.5 Hz, 1H), 5.44 (s, 1H), 5.20 (s, 1H), 4.68 (s, 2H), 4.52 (d, J=12.7 Hz, 1H), 4.42 (d, J=12.7 Hz, 1H), 3.77 (d, J=12.9 Hz, 1H), 3.64 (d, J=12.9 Hz, 1H), 2.28 (s, 3H); MS (ES) m/z: 427 (M−H$^+$); (PPARdleta EC$_{50}$: >3000 nM);

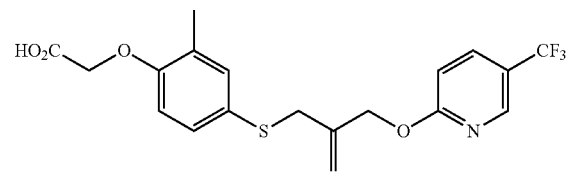

[2-methyl-4-[[2-[[[5-(trifluoromethyl)-2-pyridinyl]oxy]methyl]-2-propenyl]thio]phenoxy]-acetic acid $^1$H NMR (300 MHz, CD$_3$OD) δ 8.02 (s, 1H), 7.67 (dd, J=2.6, 9.6 Hz, 1H), 7.18 (m, 2H), 6.72 (d, J=8.4 Hz, 1H), 6.65 (d, J=9.6 Hz, 1H), 4.82 (s, 1H), 4.78 (s, 2H), 4.70 (s, 2H), 4.66 (s, 1H), 4.56 (s, 2H), 3.48 (s, 2H), 2.25 (s, 3H); MS (ES) m/z: 414 (M+H$^+$). Anal. Calcd for C$_{21}$H$_{22}$F$_3$NO$_4$S+0.4 H$_2$O: C, 54.26; H, 4.51; N, 3.33. Found: C, 54.12; H, 4.28; N, 3.56; (PPARdleta EC$_{50}$: >3000 nM);

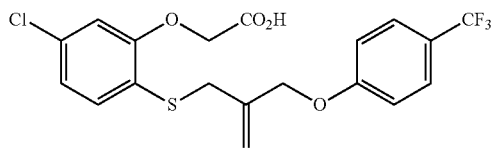 [SMILES: C=C(COc1ccc(C(F)(F)F)cc1)CSc1ccc(Cl)cc1OCC(=O)O]

[5-chloro-2-[[2-[[4-(trifluoromethyl)phenoxy]methyl]-2-propenyl]thio]phenoxy]-acetic acid $^1$H NMR (300 MHz, CDCl$_3$) δ 9.78 (brs, 1H), 7.27 (d, J=8.4 Hz, 1H), 6.95-6.91 (m, 3H), 6.76 (d, J=1.8 Hz, 1H), 5.13 (s, 1H), 5.03 (s, 1H), 4.71 (s, 2H), 4.63 (s, 2H), 3.67 (s, 2H); MS (ES) m/z: 455 (M+Na$^+$). Anal. Calcd for C$_{19}$H$_{16}$ClF$_3$O$_4$S: C, 52.72; H, 3.73. Found: C, 52.53; H, 3.52; (PPARdleta EC$_{50}$: >3000 nM); and

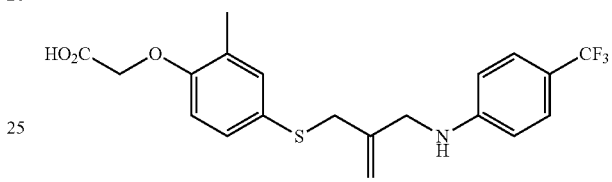

[2-methyl-4-[[2-[[[4-(trifluoromethyl)phenyl]amino]methyl]-2-propenyl]thio]phenoxy]-acetic acid $^1$H NMR (400 MHz, MeOH-d$_4$) δ 7.29 (d, J=8.6 Hz, 2H), 7.21 (s, 1H), 7.19 (dd, J=8.5, 2.0 Hz, 1H), 6.72 (d, J=8.3 Hz, 1H), 6.60 (d, J=8.6 Hz, 2H), 4.94 (s, 1H), 4.80 (s, 1H), 4.61 (s, 2H), 3.88 (s, 2H), 3.49 (s, 2H), 2.21 (s, 3H); MS (ES) m/z: 412 (M+H$^+$); (PPARdleta EC$_{50}$: >500 nM).

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms.

Pharmaceutically acceptable salts, esters, and amides include carboxylate salts (e.g., C$_{1-8}$ alkyl, cycloalkyl, aryl, heteroaryl, or non-aromatic heterocyclic) amino acid addition salts, esters, and amides which are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1-19, which is incorporated herein by reference. Representative pharmaceutically acceptable amides of the invention include those derived from ammonia, primary C$_{1-6}$ alkyl amines and secondary di (C$_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkylamines. Representative pharmaceutically acceptable esters of the invention include $C_{1-7}$ alkyl, $C_{6-7}$ cycloalkyl, phenyl, and phenyl($C_{1-6}$)alkyl esters. Preferred esters include methyl esters.

The invention also includes disclosed compounds having one or more functional groups (e.g., amino, or carboxyl) masked by a protecting group. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl) ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3, 3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4', 4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl) benzoate, p-P-benzoate, a-naphthoate, nitrate, alkyl N,N,N', N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenyl benzoyl.

Assisted Cleavage N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of special NH protective groups include

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N—(N',N'-dimethylaminomethylene).

Protection for the Carboxyl Group

Esters

Examples of esters include formate, benzoylformate, acetate, trichloroacetate, trifluoroacetate, methoxyacetate, phenoxyacetate, p-chlorophenoxyacetate, benzoate.

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, w-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenyl phosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methyl mercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

C. SYNTHESIS

The invention provides methods of making the disclosed compounds according to traditional organic synthetic methods as well as matrix or combinatorial synthetic methods. Schemes A through G describe suggested synthetic routes. Using these Schemes, the guidelines below, and the examples of compounds 1-28, a person of skill in the art may develop analogous or similar methods for a given compound that are within the invention. These methods are representative of the preferred synthetic schemes, but are not to be construed as limiting the scope of the invention.

One skilled in the art will recognize that synthesis of the compounds of the present invention may be effected by purchasing an intermediate or protected intermediate compounds described in any of the schemes disclosed herein. One skilled in the art will further recognize that during any of the processes for preparation of the compounds in the present invention, it may be necessary and/or desirable to protect sensitive or reactive groups on any of the molecules concerned. This may be achieved by means of conventional protecting groups, such as those described in "Protective Groups in Organic Synthesis", John Wiley & Sons, 1991. These protecting groups may be removed at a convenient stage using methods known from the art.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation. The compounds may also be resolved by formation of diastereomeric esters or amides, followed by chromatographic separation and removal of the chiral auxiliary. Alternatively, the compounds may be resolved using a chiral HPLC column.

Examples of the described synthetic routes include Examples 1 through 7. Compounds analogous to the target compounds of these examples can be made according to similar routes. The disclosed compounds are useful in basic research and as pharmaceutical agents as described in the next section.

General Guidance

A preferred synthesis of Formula (I) is demonstrated in Schemes A through G.

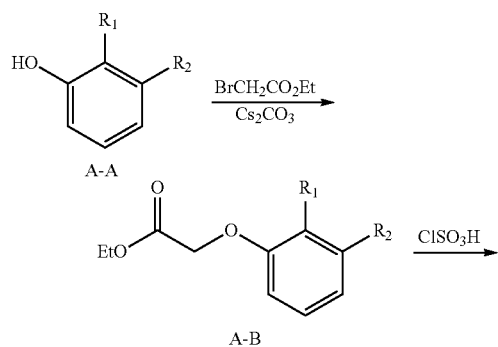

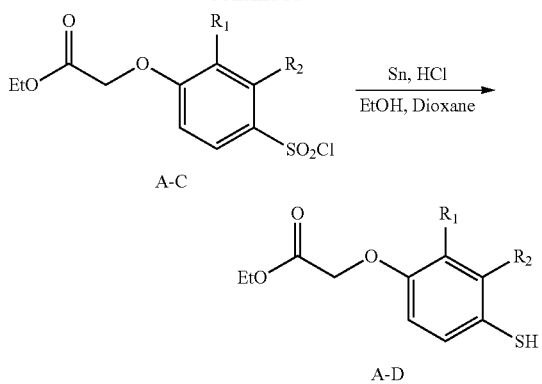

In accordance with Scheme A, phenol A-A, a variety of which are commercially available (such as 3-methylphenol, 2-ethylphenol, 2-propylphenol, 2,3-dimethylphenol, 2-chlorophenol, 2,3-dichlorophenol, 2-bromophenol, and 2-aminophenol), is alkylated to form phenoxyacetic acid ethyl ester A-B with a suitable haloacetic acid ester such as bromoacetic acid ethyl ester, in the presence of an appropriate base such as $Cs_2CO_3$, $K_2CO_3$, or NaH, in a suitable solvent such as $CH_3CN$ or THF. Sulfonation of the phenoxyacetic acid ethyl ester A-B with an appropriate sulfonating agent, such as chlorosulfonic acid, occurs selectively at the para position to provide 4-chlorosulfonylphenoxyacetic acid ethyl ester A-C. Transformation of the sulfonylchloride A-C to benzenethiol A-D is accomplished using a metal as a reducing agent, such as tin or zinc, in an acidic medium such as ethanol or dioxane.

In Schemes B, D, and E, $R_8$ and $R_9$ can be selected from, for example, H, $C_{1-8}$ alkyl, $C_{2-8}$ alkenyl, phenyl, halo, and cyano.

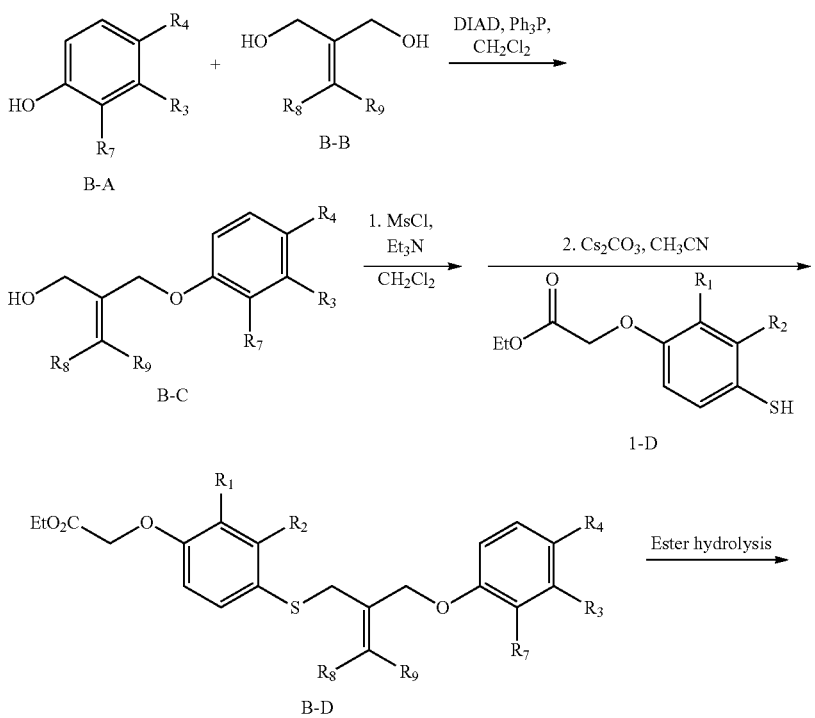

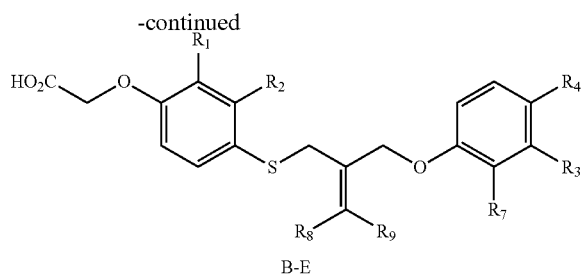

B-E

In Scheme B, Mitsunobu reaction of 1,3-diol B-B with phenol B-A provides alcohol B-C by employing a triarylphosphine such as triphenylphosphine, and an azodicarbonyl reagent such as diisopropyl azodicarboxylate, in a suitable solvent such as THF. Phenoxyacetic acid ethyl ester B-D is obtained in two steps: (1) conversion of the alcohol B-C to mesylate under standard conditions by employing methanesulfonyl chloride and triethylamine in an appropriate solvent such as $CH_2Cl_2$, and (2) alkylation of benzenethiol B-D, prepared according to Scheme A above, with the mesylate intermediate using a suitable base such as $Cs_2CO_3$, $K_2CO_3$, or NaH, in an appropriate solvent such as $CH_3CN$ or THF, under nitrogen. Under standard saponification conditions phenoxyacetic acid ethyl ester B-D is converted to acid B-E under nitrogen. The preferred hydrolysis conditions include using NaOH as a base in an aqueous alcoholic solvent system such as water-methanol, or using LiOH as a base in a milder water-THF system.

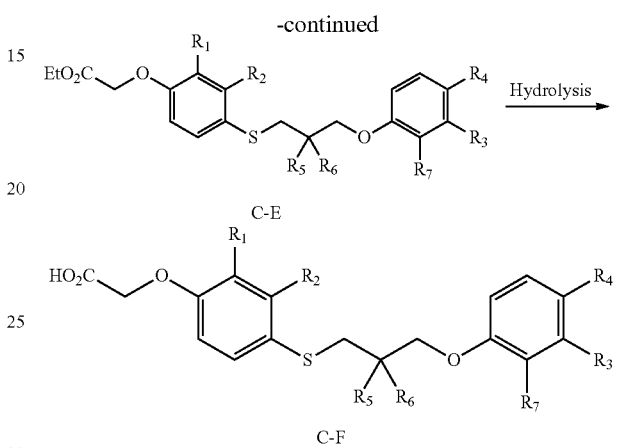

In Scheme C, $R_5$ and $R_6$ substituted malonate C-A is reduced to propane-1,3-diol C-B by using a suitable reducing agent such as lithium aluminum hydride or diisobutylaluminum hydride. After propane-1,3-diol C-B is converted to dimesylate C-C by using methanesulfonyl chloride and triethylamine in an appropriate solvent such as $CH_2Cl_2$, C-C reacts with phenol B-A in the presence of a suitable base such as $Cs_2CO_3$, $K_2CO_3$, or NaH in an appropriate solvent such as $CH_3CN$ or THF to produce mesylate C-D. Phenoxyacetic acid ethyl ester C-E is obtained by alkylation of benzenethiol A-D, prepared according to Scheme A above, with the mesylate C-D using a suitable base such as $Cs_2CO_3$, $K_2CO_3$, or NaH in an appropriate solvent such as $CH_3CN$ or THF under nitrogen. Under standard saponification conditions phenoxyacetic acid ethyl ester C-E is converted to acid C-F under nitrogen. The preferred hydrolysis conditions include using NaOH as a base in an aqueous alcoholic solvent system such as water-methanol, or using LiOH as a base in a milder water-THF system.

Scheme C

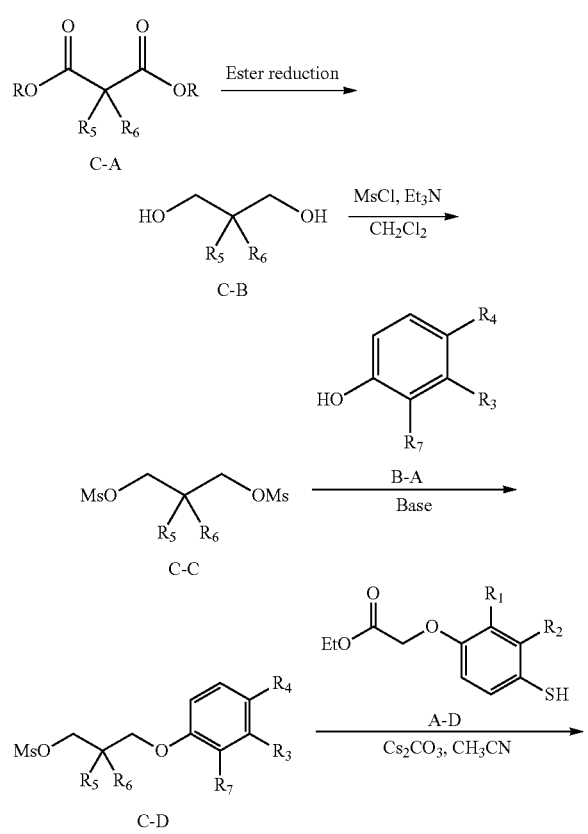

Scheme D

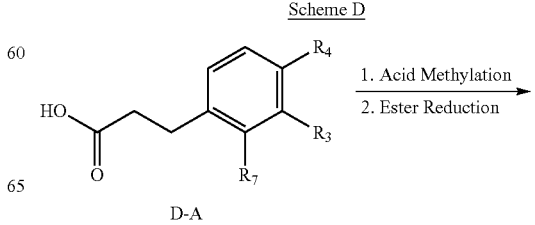

D-A

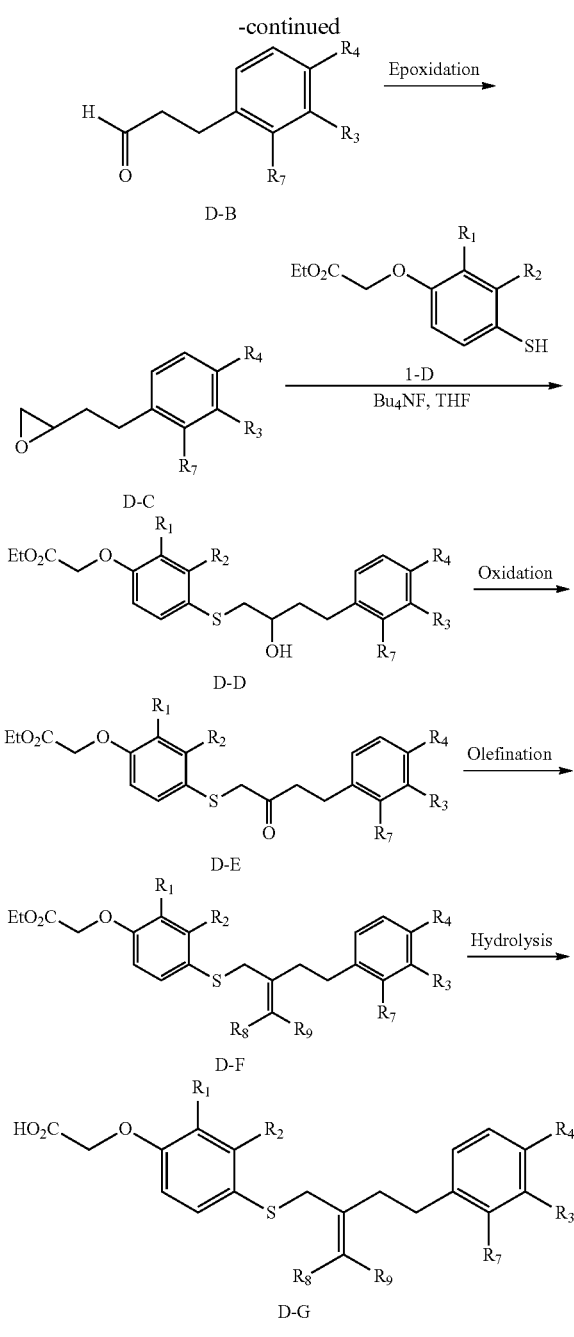

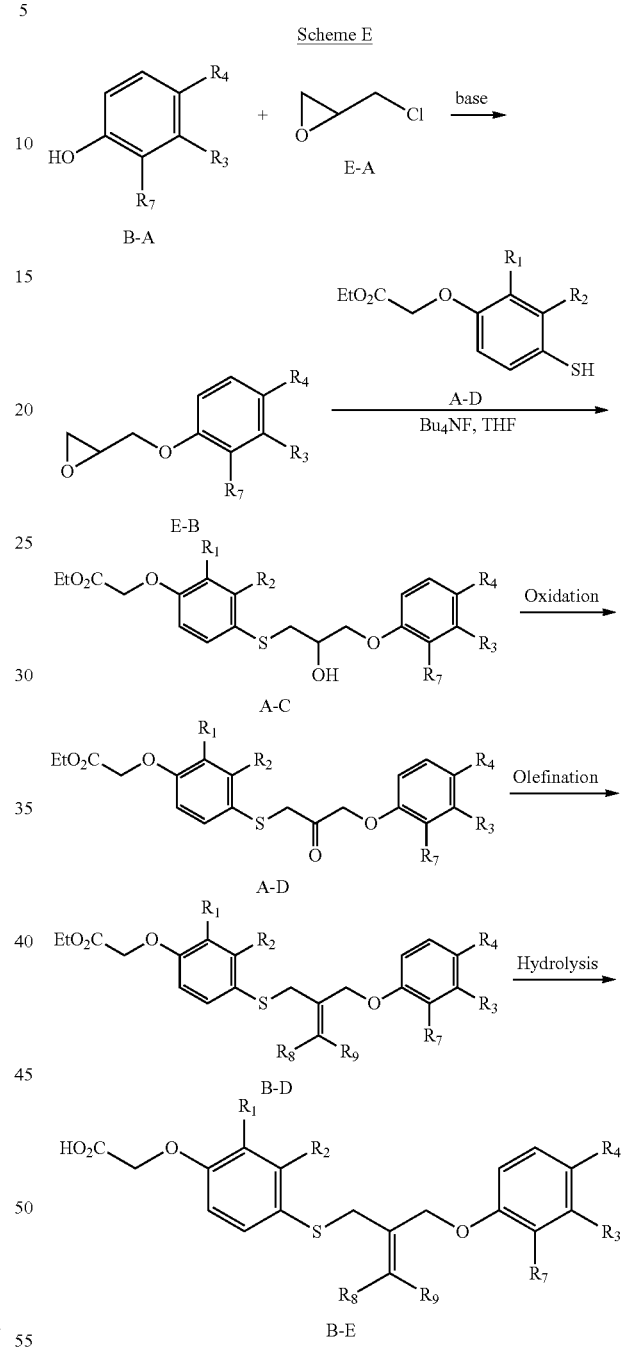

D-E with Tebbe reagent will all give D-F. Finally, saponification of ethyl ester D-F under standard conditions gives acid D-G.

In accordance with Scheme D, aldehyde D-B could be prepared in two steps by methylation of acid D-A using (trimethysilyl)diazomethane as a methylating agent followed by reduction of the methyl ester intermediate with a suitable reducing agent such as diisobutylaluminum hydride. Aldehyde D-B is transformed to epoxide D-C by reacting with dimethylsulfonium methylide, which is generated in-situ from treatment of trimethylsulfonium iodide with a strong base such as DMSO anion. Epoxide ring opening of D-C with benzenethiol A-D in the presence of a catalytic amount of tetrabutylammonium fluoride furnishes alcohol D-D, which is oxidized to ketone D-E under mild oxidation conditions by using acetic anhydride and dimethyl sulfoxide. Several types of olefination of ketone D-E may be carried out to provide alkene D-F. For example, Wittig reaction and olefination of Scheme E shows another route to prepare acid E-E as demonstrated in Scheme B. In Scheme E, epoxide E-B is obtained by treatment of phenol B-A with an appropriate base such as cesium carbonate followed by alkylation with 2-chloromethyl-oxirane E-A. Epoxide ring opening of E-B with benzenethiol A-D, prepared in Scheme A above, in the presence of a catalytic amount of tetrabutylammonium fluoride furnishes alcohol E-C, which is oxidized to ketone E-D under mild oxidation conditions by using acetic anhydride and dimethyl sulfoxide. Several types of olefination of ketone E-D may be carried out to provide alkene B-D. For example, Wittig reaction and olefination of E-D with Tebbe reagent will all give B-D. Finally, saponification of ethyl ester B-D under standard conditions gives acid B-E.

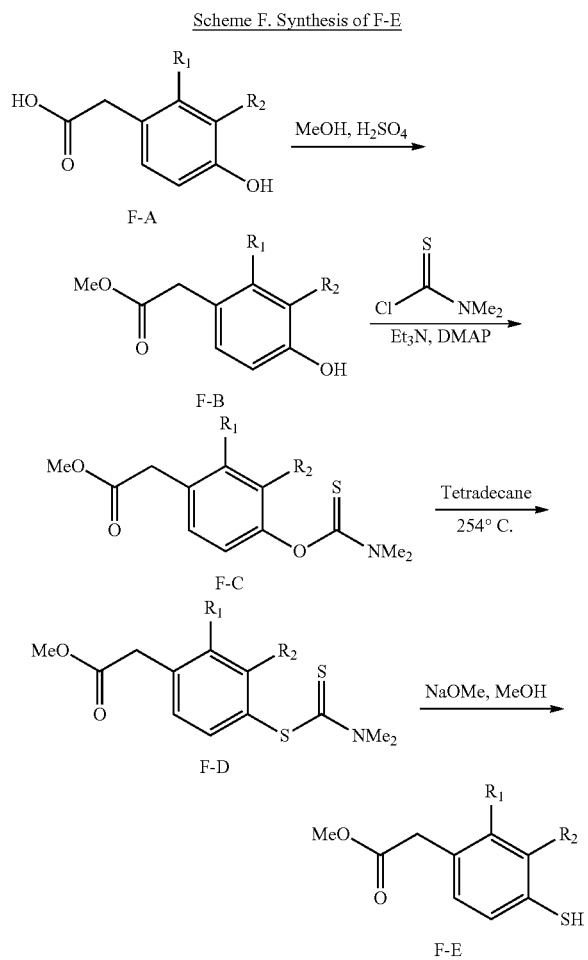

In accordance with Scheme F, (4-hydroxyphenyl) acetic acid F-A, a variety of which are commercially available (such as 3-bromo-4-hydroxyphenyl acetic acid, 3-chloro-4-hydroxyphenyl acetic acid, 3-fluoro-4-hydroxyphenyl acetic acid, 4-hydroxy-3-methoxyphenyl acetic acid, and 4-hydroxy-3-nitrophenyl acetic acid), is methylated to form (4-hydroxyphenyl) acetic acid methyl ester F-B in methanol in the presence of a catalytic amount of a suitable acid such as sulfuric acid or hydrochloric acid. The phenol F-B is converted to (4-dimethylthiocarbamoyloxyphenyl) acetic acid methyl ester F-C by reacting with dimethylthiocarbamoyl chloride in the presence of some appropriate bases such as triethylamine and 4-(dimethylamino)pyridine. At high temperature, in the preferred range of 250 to 300° C., F-C is rearranged to (4-dimethylcarbamoylsulfanylphenyl)acetic acid methyl ester F-D in a high boiling point solvent such as tetradecane. By treatment with a suitable base such as sodium methoxide F-D is transformed to (4-mercaptophenyl) acetic acid methyl ester F-E.

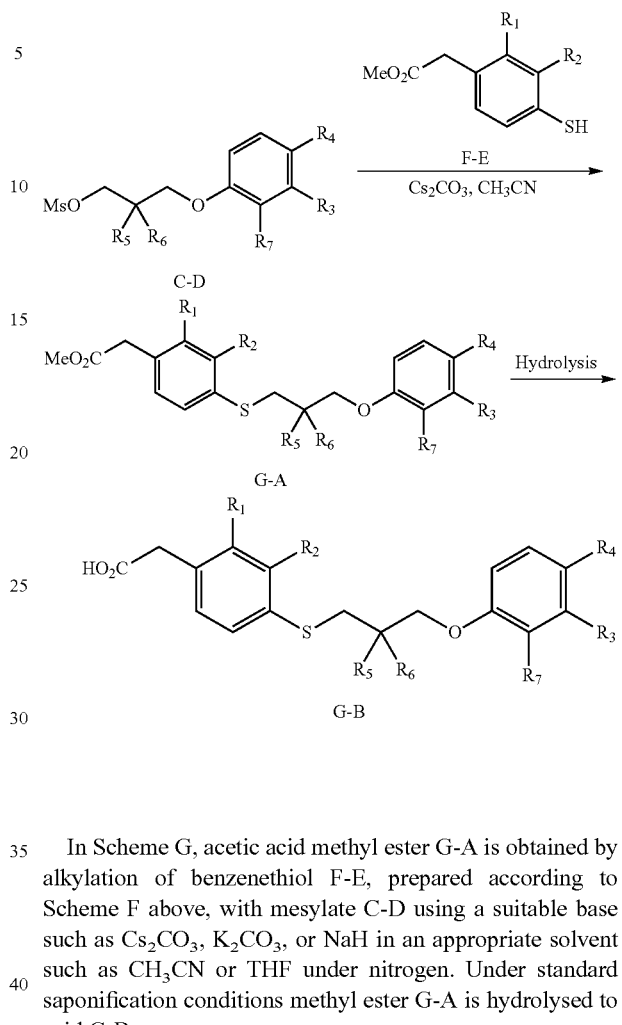

In Scheme G, acetic acid methyl ester G-A is obtained by alkylation of benzenethiol F-E, prepared according to Scheme F above, with mesylate C-D using a suitable base such as $Cs_2CO_3$, $K_2CO_3$, or NaH in an appropriate solvent such as $CH_3CN$ or THF under nitrogen. Under standard saponification conditions methyl ester G-A is hydrolysed to acid G-B.

EXAMPLES

Example I

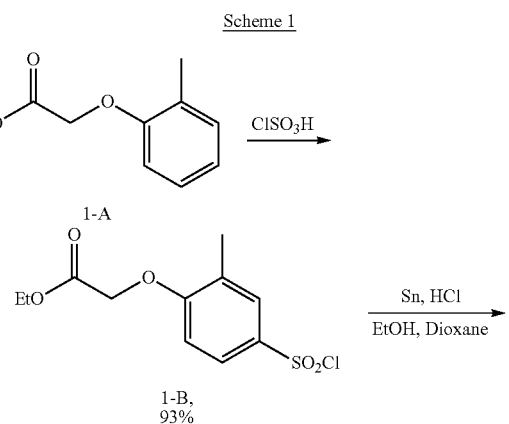

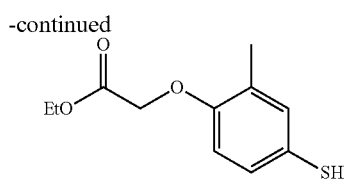

1-C,
98%

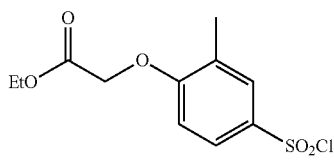

(4-Chlorosulfonyl-2-methyl-phenoxy)-acetic acid ethyl ester

To a flask containing chlorosulfonic acid (15.0 mL, 226 mmol) at 4° C. was added ethyl (2-methylphenoxy)acetate 1-A (10.0 g, 51.6 mmol) slowly. The mixture was stirred at 4° C. for 30 min and room temperature for 2 h, and then poured into ice water. The precipitated white solid was filtered, washed with water, and dried under vacuum overnight to provide 14.0 g (93%) of 1-B as a white solid; $^1$H NMR (300 MHz, CDCl$_3$) δ 7.87-7.84 (m, 2H), 6.80 (d, J=9.5 Hz, 1H), 4.76 (s, 2H), 4.29 (q, J=7.1 Hz, 2H), 2.37 (s, 3H), 1.31 (t, J=7.1 Hz, 3H); MS (ES) m/z: 315 (M+Na$^+$).

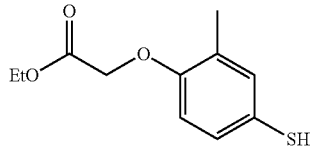

1-C (4-Mercapto-2-methyl-phenoxy)-acetic acid ethyl ester

To a solution of 1-B (4.70 g, 16.1 mmol) in EtOH (20 mL) was added a solution of 4.0 M HCl in dioxane (20 mL) followed by 100 mesh tin powder (9.80 g, 82.6 mmol) portionwise. The mixture was refluxed for 2 h, poured into CH$_2$Cl$_2$/ice (100 mL), and filtered. The filtrate was separated, and the aqueous layer was extracted with CH$_2$Cl$_2$. The combined organic phases were washed with water, dried, and concentrated to give 3.56 g (98%) of 1-C as a yellow oil; $^1$H NMR (300 MHz, CDCl$_3$) δ 7.14-7.03 (m, 2H), 6.59 (d, J=8.4 Hz, 1H), 4.60 (s, 2H), 4.25 (q, J=7.1 Hz, 2H), 2.24 (s, 3H), 1.29 (t, J=7.1 Hz, 3H).

Scheme 2

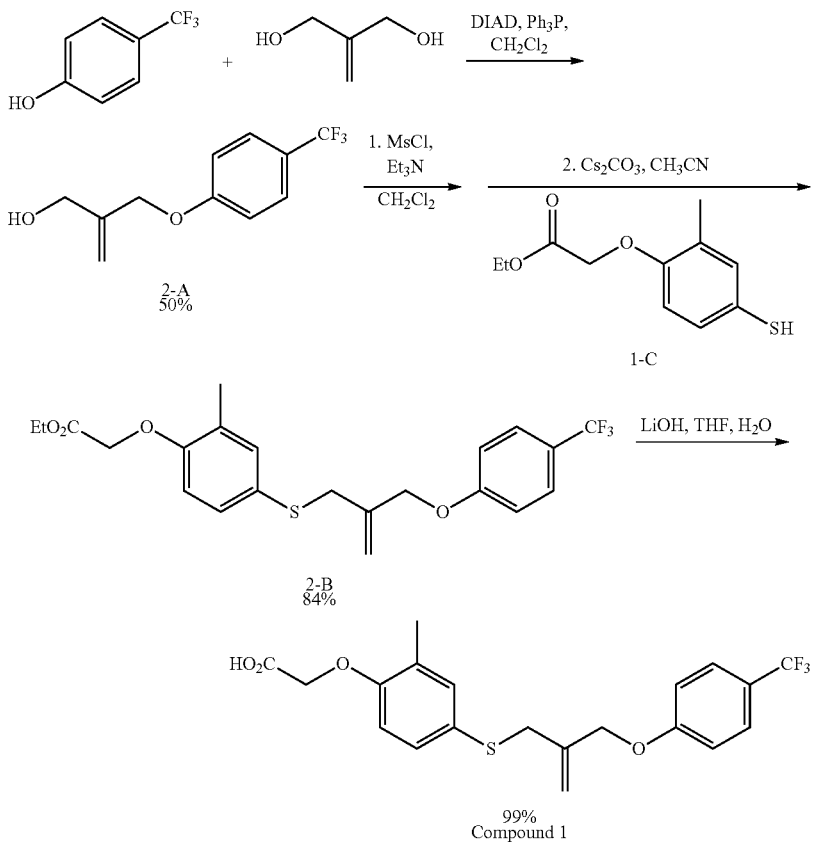

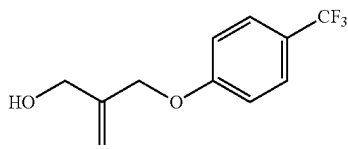

2-A

2-(4-Trifluoromethyl-phenoxymethyl)-prop-2-en-1-ol

To a mixture of 4-trifluoromethylphenol (49.0 g, 302 mmol), 2-methylene-1,3-propanediol (40.0 g, 454 mmol), and diisopropyl azodicarboxylate (67.4 g, 333 mmol) in $CH_2Cl_2$ (400 mL) at 0° C. was charged with a solution of triphenylphosphine (87.2 g, 333 mmol) in $CH_2Cl_2$ (400 mL) dropwise. After the mixture was stirred at 0° C. and then allowed to warm up to room temperature overnight, $CH_2Cl_2$ was evaporated under reduced pressure. To the residue was added $Et_2O$ and hexane, and the mixture was cooled to 0° C. The precipitated solid was filtered, and the filtrate was concentrated and column chromatographed (EtOAc/hexane: 1/4) to give 35.2 g (50%) of 2-A; $^1$H NMR (300 MHz, $CDCl_3$) δ 7.55 (d, J=8.6 Hz, 2H), 6.99 (d, J=8.6 Hz, 2H), 5.33 (d, J=0.9 Hz, 1H), 5.29 (d, J=0.9 Hz, 1H), 4.65 (s, 2H), 4.27 (d, J=6.0 Hz, 2H).

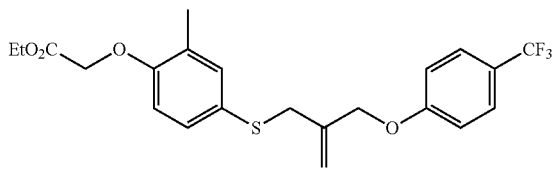

2-B

{2-Methyl-4-[2-(4-trifluoromethyl-phenoxymethyl)-allylsulfanyl]-phenoxy}-acetic acid ethyl ester General Procedure 1 for the Formation of Thioether:

To a solution of 2-A (18.1 g, 78.2 mmol) in $CH_2Cl_2$ (400 mL) at 0° C. were added $Et_3N$ (23.0 mL, 165 mmol) and methanesulfonyl chloride (13.4 g, 117 mmol). The mixture was stirred at 0° C. for 1 h and room temperature overnight and diluted with saturated $NaHCO_3$ (100 mL). The organic layer was separated and the aqueous layer was extracted with $CH_2Cl_2$ (×3). The combined organic phases were dried and concentrated to provide 24.2 g of the crude product.

A mixture of the above crude product, (4-mercapto-2-methyl-phenoxy)acetic acid ethyl ester 1-C (21.2 g, 93.8 mmol), and $Cs_2CO_3$ (76.2 g, 234 mmol) in $CH_3CN$ (290 mL) was stirred at room temperature for 2 h. Water was added and the mixture was extracted with $CH_2Cl_2$. The combined organic layers were dried, concentrated, and column chromatographed (EtOAc/hexane: 1/10) to provide 28.8 g (84%) of 2-B; $^1$H NMR (300 MHz, $CDCl_3$) δ 7.53 (d, J=8.7 Hz, 2H), 7.20 (s, 1H), 7.16 (dd, J=8.4, 2.2 Hz, 1H), 6.96 (d, J=8.6 Hz, 2H), 6.59 (d, J=8.4 Hz, 1H), 5.13 (d, J=0.9 Hz, 1H), 4.98 (s, 1H), 4.65 (s, 2H), 4.60 (s, 2H), 4.26 (q, J=7.1 Hz, 2H), 3.56 (s, 2H), 2.24 (s, 3H), 1.29 (t, J=7.1 Hz, 3H); MS (ES) m/z: 463 (M+Na$^+$).

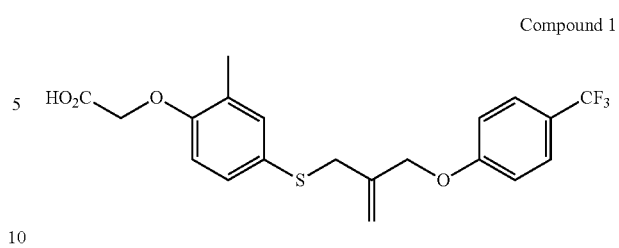

Compound 1

{2-Methyl-4-[2-(4-trifluoromethyl-phenoxymethyl)-allylsulfanyl]-phenoxy}-acetic acid General Procedure 2 for the Hydrolysis of the Ethyl and Methyl Esters:

To a solution of 2-B (28.8 g, 65.5 mmol) in THF (576 mL) at 0° C. under $N_2$ was added 1.0 M LiOH (131 mL, 131 mmol). After stirring at 0° C. for 45 min and at room temperature for 2.5 h, the mixture was cooled to 0° C., acidified with 1 M HCl, and extracted with EtOAc (×3). The extracts were dried, concentrated, and purified by column chromatography to give 26.7 g (99%) of Compound 1; $^1$H NMR (300 MHz, $CDCl_3$) δ 7.52 (d, J=8.6 Hz, 2H), 7.21 (s, 1H), 7.17 (dd, J=8.4, 2.2 Hz, 1H), 6.95 (d, J=8.6 Hz, 2H), 6.62 (d, J=8.4 Hz, 1H), 5.14 (d, J=1.0 Hz, 1H), 4.99 (d, J=1.0 Hz, 1H), 4.65 (s, 4H), 3.57 (s, 2H), 2.23 (s, 3H); MS (ES) m/z: 435 (M+Na$^+$). Analysis calc'd for $C_{20}H_{19}O_4F_3S.0.1H_2O$: C, 57.99; H, 4.67; S, 7.74; F, 13.76, found: C, 58.06; H, 4.64; S, 7.46; F, 13.91.

Example II

Scheme 4

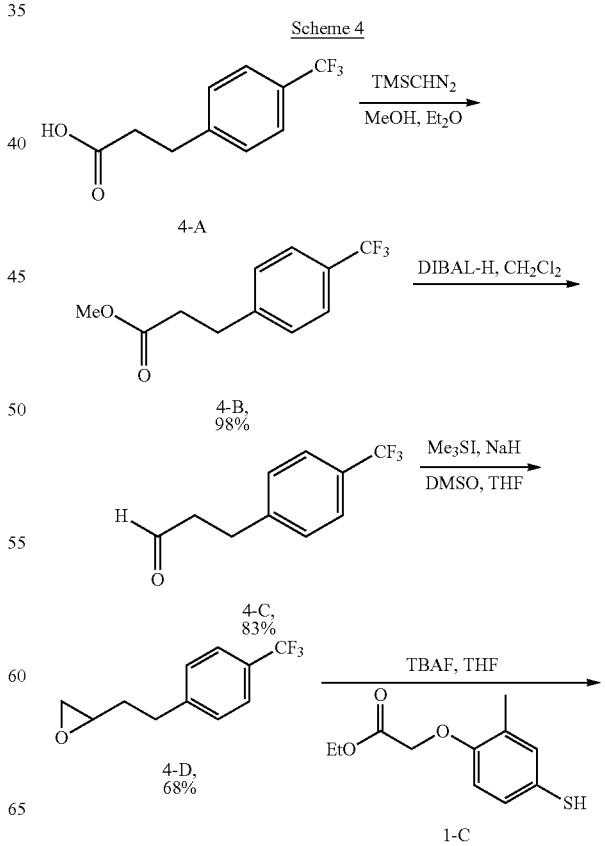

-continued

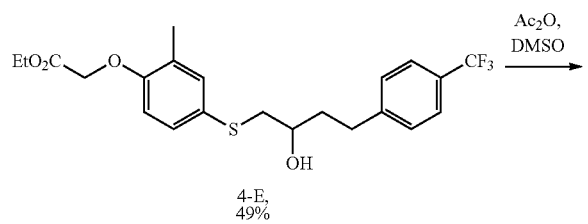

4-E,
49%

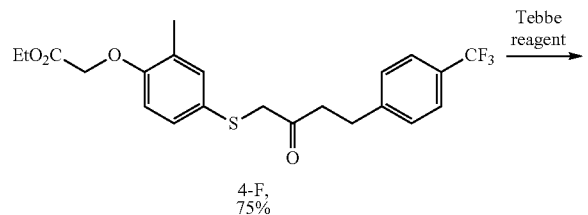

4-F,
75%

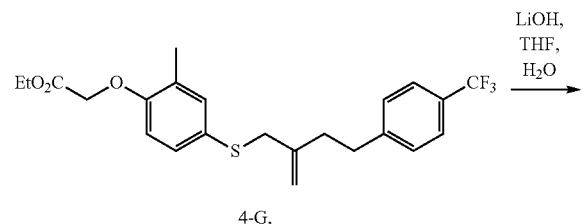

4-G,
19%

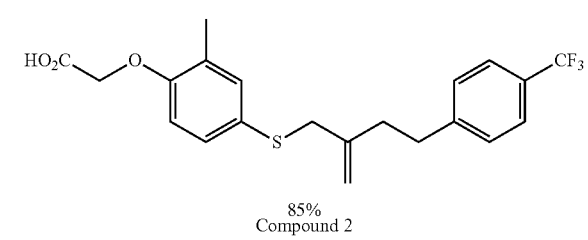

85%
Compound 2

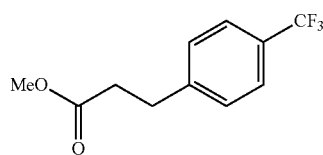

4-B 3-(4-Trifluoromethyl-phenyl)-propionic acid methyl ester

To a solution of 4-A (1.00 g, 4.59 mmol) in Et$_2$O (20 mL) and MeOH (10 mL) was added 1.0 M (trimethylsilyl)diazomethane (9.16 mL, 9.16 mmol) in hexane. After stirring at room temperature for 1 h, the solvents were removed under reduced pressure. The residue was dissolved in Et$_2$O, washed with saturated NaHCO$_3$ and brine, dried, and concentrated to give 1.04 g (98%) of 4-B; $^1$H NMR (300 MHz, CDCl$_3$) δ 7.54 (d, J=8.1 Hz, 2H), 7.31 (d, J=8.1 Hz, 2H), 3.67 (s, 3H), 3.01 (t, J=7.7 Hz, 2H), 2.65 (t, J=7.7 Hz, 2H); MS (ES) m/z: 255 (M+Na$^+$).

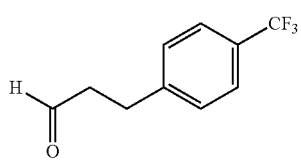

4-C 3-(4-Trifluoromethyl-phenyl)-propionaldehyde

To a solution of 4-B (1.10 g, 4.74 mmol) in CH$_2$Cl$_2$ (20 mL) at −78° C. was added 1.0 M diisobutylaluminum hydride (4.74 mL, 4.74 mmol). The mixture was stirred at −78° C. for 10 min and quenched with 10% HCl in MeOH (5 mL). After warming to room temperature, the mixture was filtered and the filtrate was concentrated and column chromatographed to provide 796 mg (83%) of 4-C; $^1$H NMR (400 MHz, CDCl$_3$) δ 9.82 (d, J=1.0 Hz, 1H), 7.54 (d, J=8.1 Hz, 2H), 7.31 (d, J=8.0 Hz, 2H), 3.01 (t, J=7.4 Hz, 2H), 2.82 (t, J=7.3 Hz, 2H).

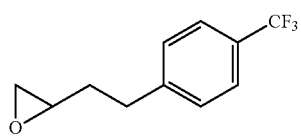

4-D

2-[2-(4-Trifluoromethyl-phenyl)-ethyl]-oxirane

A mixture of NaH (52 mg, 1.3 mmol; 60% in mineral oil) in DMSO (15 mL) was heated at 70° C. for 30 min and allowed to cool to room temperature. After diluting with THF (10 mL), to the mixture at 0° C. was slowly added a solution of trimethylsulfonium iodide (306 mg, 1.50 mmol) in DMSO (10 mL). After stirring for 10 min at 0° C., a solution of 4-C (202 mg, 1.00 mmol) in THF (10 mL) was introduced. Stirring was continued for 1 h at 0° C. and the mixture was diluted with water and extracted with Et$_2$O. The extracts were dried, concentrated, and column chromatographed (EtOAc/hexane: 1/7) to provide 147 mg (68%) of 4-D; $^1$H NMR (300 MHz, CDCl$_3$) δ 7.54 (d, J=8.1 Hz, 2H), 7.31 (d, J=8.0 Hz, 2H), 2.97-2.90 (m, 1H), 2.88-2.78 (m, 2H), 2.75 (m, 1H), 2.47 (dd, J=4.9, 2.7 Hz, 1H), 1.98-1.73 (m, 2H).

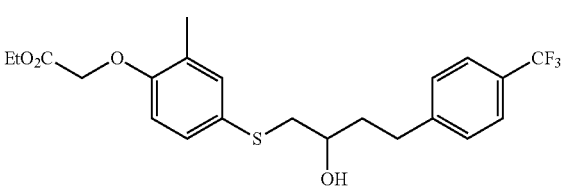

4-E

{4-[2-Hydroxy-4-(4-trifluoromethyl-phenyl)-butyl-sulfanyl]-2-methyl-phenoxy}-acetic acid ethyl ester A mixture of 4-D (251 mg, 1.16 mmol), (4-mercapto-2-methylphenoxy)acetic acid ethyl ester 1-C (394 mg, 1.74 mmol), and tetrabutylammonium fluoride (0.12 mL, 0.12 mmol; 1.0 M in THF) in THF (5 mL) was stirred at room temperature overnight and concentrated. The residue was purified by column chromatography (EtOAc/hexane: 1/5) to give 250 mg (49%) of 4-E; ¹H NMR (300 MHz, CDCl₃) δ 7.51 (d, J=8.0 Hz, 2H), 7.26 (d, J=8.0 Hz, 2H), 7.23 (d, J=2.1 Hz, 1H), 7.18 (dd, J=8.4, 2.3 Hz, 1H), 6.61 (d, J=8.4 Hz, 1H), 4.62 (s, 2H), 4.26 (q, J=7.1 Hz, 2H), 3.63-3.55 (m, 1H), 3.01 (dd, J=13.6, 3.4 Hz, 1H), 2.91-2.81 (m, 1H), 2.79-2.66 (m, 2H), 2.56 (brs, 1H), 2.25 (s, 3H), 1.84-1.76 (m, 2H), 1.30 (t, J=7.1 Hz, 3H); MS (ES) m/z: 465 (M+Na⁺).

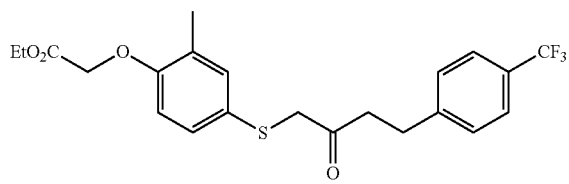

4-F

{2-Methyl-4-[2-oxo-4-(4-trifluoromethyl-phenyl)-butylsulfanyl]-phenoxy}-acetic acid ethyl ester A mixture of 4-E (370 mg, 0.837 mmol) in Ac₂O (2.5 mL) and DMSO (4 mL) was stirred at room temperature for 24 h, diluted with water, and extracted with Et₂O. The extracts were dried, concentrated, and purified by column chromatography to give 278 mg (75%) of 4-F; ¹H NMR (300 MHz, CDCl₃) δ 7.51 (d, J=8.1 Hz, 2H), 7.26 (d, J=8.0 Hz, 2H), 7.15 (d, J=1.7 Hz, 1H), 7.04 (dd, J=8.5, 2.3 Hz, 1H), 6.57 (d, J=8.5 Hz, 1H), 4.60 (s, 2H), 4.26 (q, J=7.1 Hz, 2H), 3.52 (s, 2H), 2.92 (s, 4H), 2.23 (s, 3H), 1.29 (t, J=7.1 Hz, 3H); MS (ES) m/z: 463 (M+Na⁺).

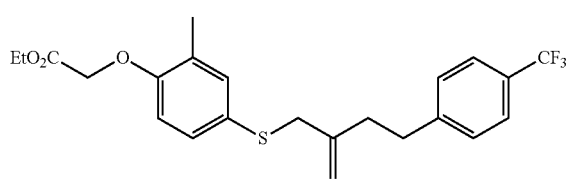

4-G (2-Methyl-4-{2-[2-(4-trifluoromethyl-phenyl)-ethyl]-allylsulfanyl}-phenoxy)-acetic acid ethyl ester To a solution of 4-F (53 mg, 0.12 mmol) in THF (1 mL) at −78° C. was slowly added 0.5 M Tebbe reagent (0.24 mL, 0.12 mmol) in toluene. The mixture was gradually warmed to 0° C., stirred at the same temperature for 4.5 h, diluted with saturated NaHCO₃, and extracted with Et₂O. The combined organic layers were dried, concentrated, and column chromatographed (EtOAc/hexane: 1/10) to give 10 mg (19%) of 4-G; ¹H NMR (300 MHz, CDCl₃) δ 7.53 (d, J=8.1 Hz, 2H), 7.29 (d, J=8.0 Hz, 2H), 7.18 (d, J=1.9 Hz, 1H), 7.12 (dd, J=8.4, 2.2 Hz, 1H), 6.60 (d, J=8.4 Hz, 1H), 4.79 (s, 2H), 4.61 (s, 2H), 4.26 (q, J=7.1 Hz, 2H), 3.45 (s, 2H), 2.82 (t, J=8.0 Hz, 2H), 2.50 (t, J=8.0 Hz, 2H), 2.25 (s, 3H), 1.28 (t, J=7.1 Hz, 3H); MS (ES) m/z: 461 (M+Na⁺).

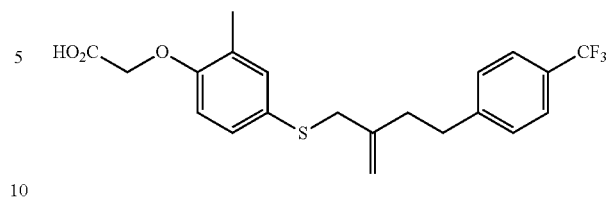

Compound 2

(2-Methyl-4-{2-[2-(4-trifluoromethyl-phenyl)-ethyl]-allylsulfanyl}-phenoxy)-acetic acid Following general procedure 2 gave Compound 2 (85%); ¹H NMR (300 MHz, CDCl₃) δ 7.51 (d, J=8.0 Hz, 2H), 7.25 (d, J=7.7 Hz, 2H), 7.11 (s, 1H), 7.06 (d, J=7.5 Hz, 1H), 6.56 (d, J=6.8 Hz, 1H), 4.78 (s, 1H), 4.77 (s, 1H), 3.41 (s, 2H), 2.79 (t, J=8.0 Hz, 2H), 2.47 (t, J=8.0 Hz, 2H), 2.15 (s, 3H); MS (ES) m/z: 433 (M+Na⁺).

Example III

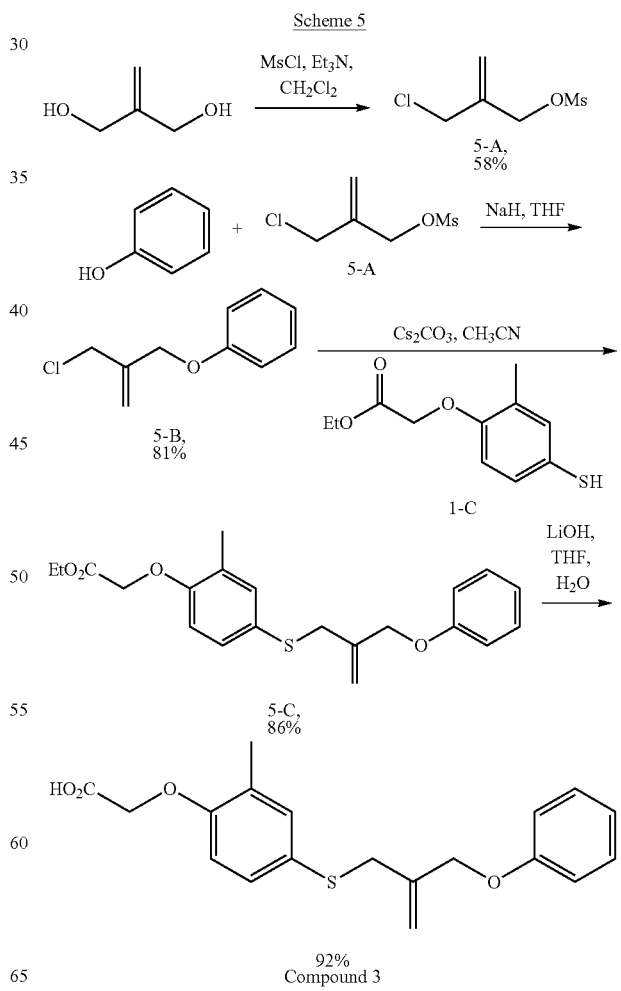

Scheme 5

Compound 3

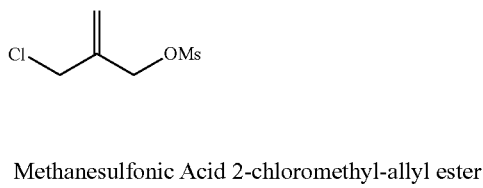

5-A

Methanesulfonic Acid 2-chloromethyl-allyl ester

To a solution of 2-methylenepropane-1,3-diol (257 mg, 2.92 mmol) in CH$_2$Cl$_2$ (4 mL) and CH$_3$CN (4 mL) at 0° C. were added Et$_3$N (1.76 mL, 12.6 mmol) and methanesulfonyl chloride (1.01 g, 8.79 mmol). After the mixture was stirred at 0° C. for 2 h and then allowed to warmed up to room temperature overnight, saturated NaHCO$_3$ was added. The organic layer was separated and the aqueous layer was extracted with CH$_2$Cl$_2$. The combined organic phases were dried, concentrated, and column chromatographed (EtOAc/hexane: 1/3) to give 313 mg (58%) of 5-A; $^1$H NMR (300 MHz, CDCl$_3$) δ 5.47 (s, 1H), 5.42 (s, 1H), 4.82 (s, 2H), 4.16 (s, 2H), 3.06 (s, 3H); MS (ES) m/z: 207 (M+Na$^+$).

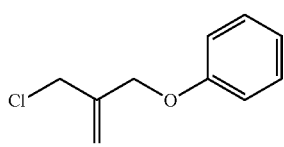

5-B

(2-Chloromethyl-allyloxy)-benzene

To a suspension of NaH (40 mg, 1.0 mmol; 60% in mineral oil) in THF (2 mL) was added a solution of phenol (94 mg, 1.0 mmol) in THF (1 mL). After stirring at room temperature for 15 min, the mixture was transferred to a solution of methanesulfonic acid 2-chloromethylallyl ester 5-A (185 mg, 1.00 mmol) in THF (2 mL). The mixture was stirred at room temperature for 1 h, then heated at 40° C. overnight, diluted with water, and extracted with EtOAc. The extracts were dried, concentrated, and column chromatographed (EtOAc/hexane: 1/9) to provide 148 mg (81%) of 5-B; $^1$H NMR (300 MHz, CDCl$_3$) δ 7.30-7.27 (m, 2H), 6.97-6.91 (m, 3H), 5.35 (s, 1H), 5.34 (s, 1H), 4.60 (s, 2H), 4.16 (s, 2H).

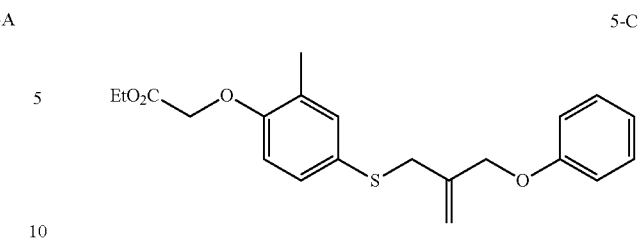

5-C

[2-Methyl-4-(2-phenoxymethyl-allylsulfanyl)phenoxy]-acetic acid ethyl ester

General Procedure 3 for the Formation of Thioether:

A mixture of 5-B (96 mg, 0.53 mmol), (4-mercapto-2-methyl-phenoxy)acetic acid ethyl ester 1-C (145 mg, 0.642 mmol), and Cs$_2$CO$_3$ (417 mg, 1.28 mmol) in CH$_3$CN (3 mL) was stirred for 5 h at room temperature. Water was added and the mixture was extracted with Et$_2$O. The combined organic layers were dried, concentrated, and column chromatographed (EtOAc/hexane: 1/10) to provide 168 mg (85%) of 5-C; $^1$H NMR (400 MHz, CDCl$_3$) δ 7.28-7.23 (m, 2H), 7.20 (d, J=2.0 Hz, 1H), 7.16 (dd, J=8.4, 2.3 Hz, 1H), 6.95-6.89 (m, 3H), 6.59 (d, J=8.4 Hz, 1H), 5.13 (s, 1H), 4.95 (s, 1H), 4.60 (s, 2H), 4.58 (s, 2H), 4.24 (q, J=7.1 Hz, 2H), 3.56 (s, 2H), 223 (s, 3H), 1.27 (t, J=7.4 Hz, 3H); MS (ES) m/z: 395 (M+Na$^+$).

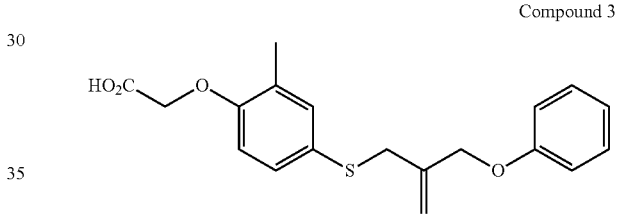

Compound 3

[2-Methyl-4-(2-phenoxymethyl-allylsulfanyl)-phenoxy]-acetic acid

Following general procedure 2 gave Compound 3 (86%); $^1$H NMR (300 MHz, CDCl$_3$) δ 7.29-7.24 (m, 2H), 7.21 (s, 1H), 7.18 (d, J=8.4 Hz, 1H), 6.97-6.89 (m, 3H), 6.62 (d, J=8.4 Hz, 1H), 5.15 (s, 1H), 4.98 (s, 1H), 4.66 (s, 2H), 4.61 (s, 2H), 3.58 (s, 2H), 2.23 (s, 3H); MS (ES) m/z: 367 (M+Na$^+$).

Example IV

Scheme 6

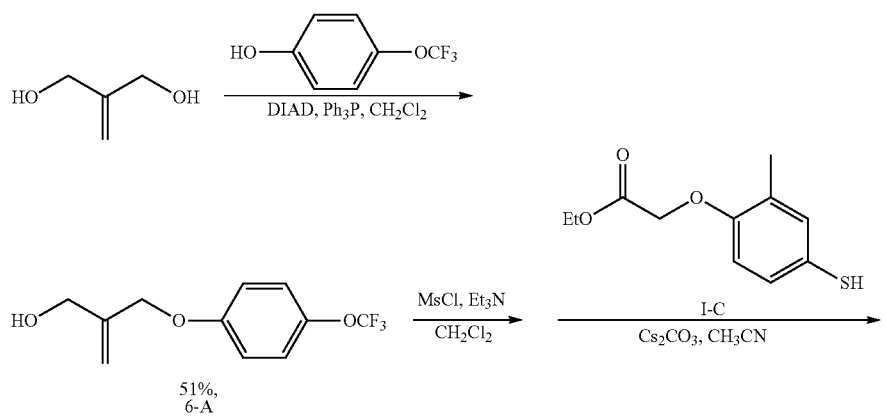

-continued

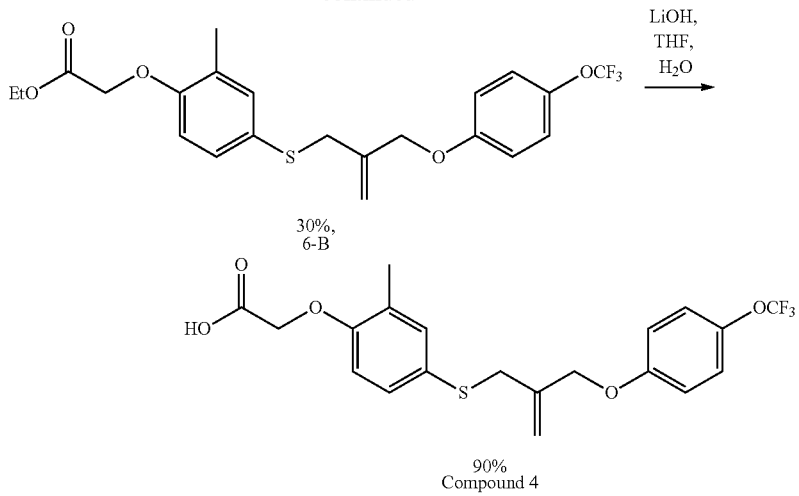

30%,
6-B

LiOH, THF, H₂O

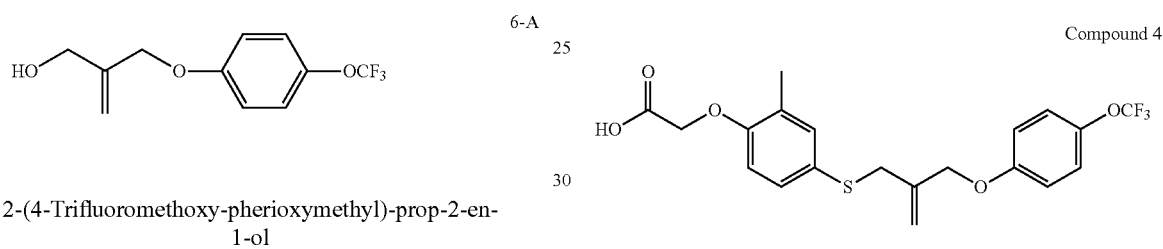

90%
Compound 4

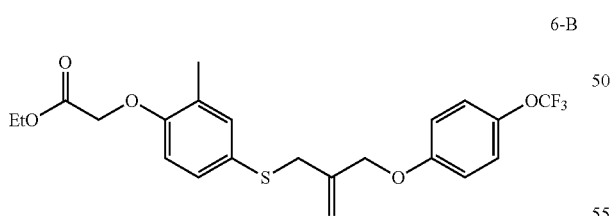

2-(4-Trifluoromethoxy-pherioxymethyl)-prop-2-en-1-ol

To a mixture of 4-trifluoromethoxyphenol (2.37 g, 13.1 mmol), 2-methylene-propane-1,3-diol (1.73 g, 19.6 mmol), and diisopropyl azodicarboxylate (3.96 g, 19.6 mmol) in CH$_2$Cl$_2$ (50 mL) was added a solution of Ph$_3$P (5.13 g, 19.6 mmol) in 50 mL of CH$_2$Cl$_2$ in 30 minutes. After stirring for 5 hours, the mixture was diluted with Et$_2$O (100 mL), washed with 1 N NaOH, dried, concentrated, and column chromatographed to give 1.7 g (51%) of 6-A; $^1$H NMR (300 MHz, CDCl$_3$) δ 7.13 (d, J=9.1 Hz, 2H), 6.91 (dd, J=9.2, 2.3 Hz, 2H), 5.31 (d, J=0.9 Hz, 1H), 5.28 (d, J=0.9 Hz, 1H), 4.59 (s, 2H), 4.26 (d, J=6.1 Hz, 2H), 1.63 (t, J=6.1 Hz, 1H).

6-B

{2-Methyl-4-[2-(4-trifluoromethoxy-phenoxymethyl)-allylsulfanyl]-phenoxy}-acetic acid ethyl ester Following general procedure 1 gave 6-B; $^1$H NMR (300 MHz, CDCl$_3$) δ 7.21-7.11 (m, 4H), 6.88 (dd, J=9.2, 2.3 Hz, 2H), 6.60 (d, J=8.4 Hz, 1H), 5.13 (d, J=1.1 Hz, 1H), 4.96 (d, J=0.7 Hz, 1H), 4.60 (s, 4H), 4.26 (q, J=7.1 Hz, 2H), 3.56 (s, 2H), 2.24 (s, 3H), 1.29 (t, J=7.1 Hz, 3H); MS (ES) m/z: 479 (M+Na$^+$).

Compound 4

[2-Methyl-4-(2-p-tolyloxymethyl-allylsulfanyl)-phenoxy]-acetic acid

Following general procedure 2 gave Compound 4; $^1$H NMR (300 MHz, CDCl$_3$) δ 7.19-7.10 (m, 4H), 6.88 (d, J=9.2 Hz, 2H), 6.62 (d, J=7.9 Hz, 1H), 5.13 (s, 1H), 4.98 (s, 1H), 4.59 (s, 4H), 3.56 (s, 2H), 2.21 (s, 3H); MS (ES) m/z: 428 (M+H$^+$); Anal. Calcd. for C$_{20}$H$_{19}$F$_3$O$_5$S.0.2H$_2$O: C, 55.60; H, 4.53. Found: C, 55.61; H, 4.36.

Example V

Scheme 7

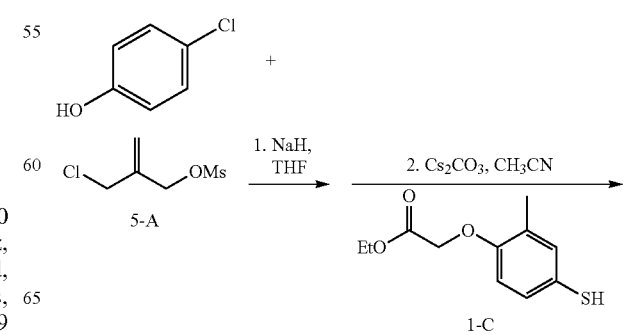

-continued

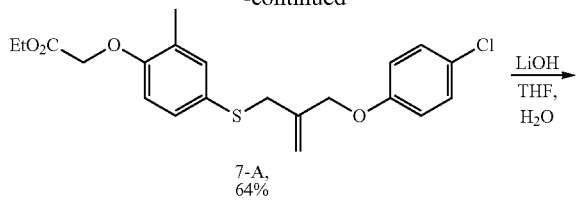

7-A, 64%

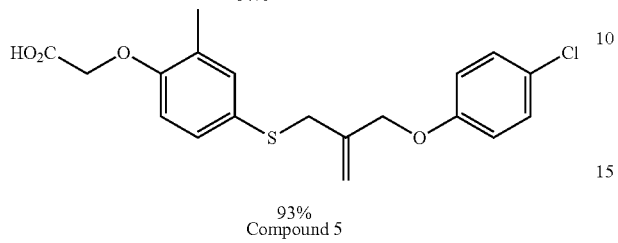

93%
Compound 5

7-A

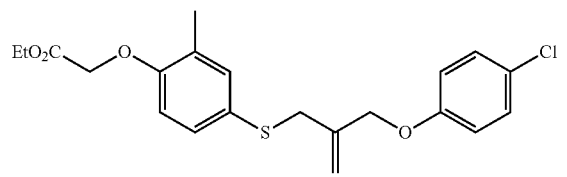

{4-[2-(4-Chloro-phenoxymethyl)-allylsulfanyl]-2-methyl-phenoxy}-acetic acid ethyl ester General Procedure 4 for Formation of Both Ether and Thioether:

To a suspension of NaH (28 mg, 0.70 mmol; 60% in mineral oil) in THF (1 mL) was added a solution of 4-chlorophenol (89 mg, 0.69 mmol) in THF (1 mL). After stirring at room temperature for 30 min, a solution of methanesulfonic acid 2-chloromethylallyl ester 5-A (128 mg, 0.693 mmol) in THF (1 mL) was added, and the mixture was heated at 50° C. overnight. To the mixture (4-mercapto-2-methylphenoxy)acetic acid ethyl ester 1-C (204 mg, 0.901 mmol), Cs$_2$CO$_3$ (450 mg, 1.38 mmol), and CH$_3$CN (5 mL) were added sequentially. After stirring at room temperature for 1 h, the reaction mixture was diluted with water and extracted with Et$_2$O. The organic phase was dried, concentrated, and column chromatographed (EtOAc/hexane) to provide 180 mg (64%) of 7-A; $^1$H NMR (400 MHz, CDCl$_3$) δ 7.20 (d, J=8.9 Hz, 2H), 7.21-7.19 (m, 1H), 7.15 (dd, J=8.4, 2.2 Hz, 1H), 6.82 (d, J=9.0 Hz, 2H), 6.59 (d, J=8.4 Hz, 1H), 5.11 (d, J=1.0 Hz, 1H), 4.95 (s, 1H), 4.60 (s, 2H), 4.57 (s, 2H), 4.25 (q, J=7.1 Hz, 2H), 3.55 (s, 2H), 2.24 (s, 3H), 1.28 (t, J=7.1 Hz, 3H); MS (ES) m/z: 429 (M+Na$^+$).

Compound 5

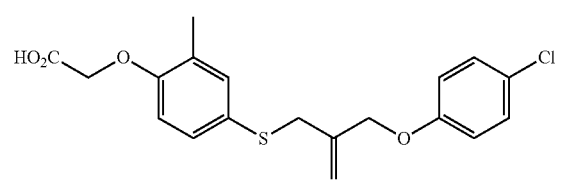

{4-[2-(4-Chloro-phenoxymethyl)-allylsulfanyl]-2-methyl-phenoxy}-acetic acid

Following general procedure 2 gave Compound 5(93%); $^1$H NMR (400 MHz, CDCl$_3$) δ 7.22-7.20 (m, 1H), 7.20 (d, J=8.8 Hz, 2H), 7.16 (d, J=8.4 Hz, 1H), 6.82 (d, J=8.9 Hz, 2H), 6.61 (d, J=8.4 Hz, 1H), 5.12 (s, 1H), 4.97 (s, 1H), 4.66 (s, 2H), 4.57 (s, 2H), 3.56 (s, 2H), 2.23 (s, 3H); MS (ES) m/z: 401 (M+Na$^+$).

Example VI

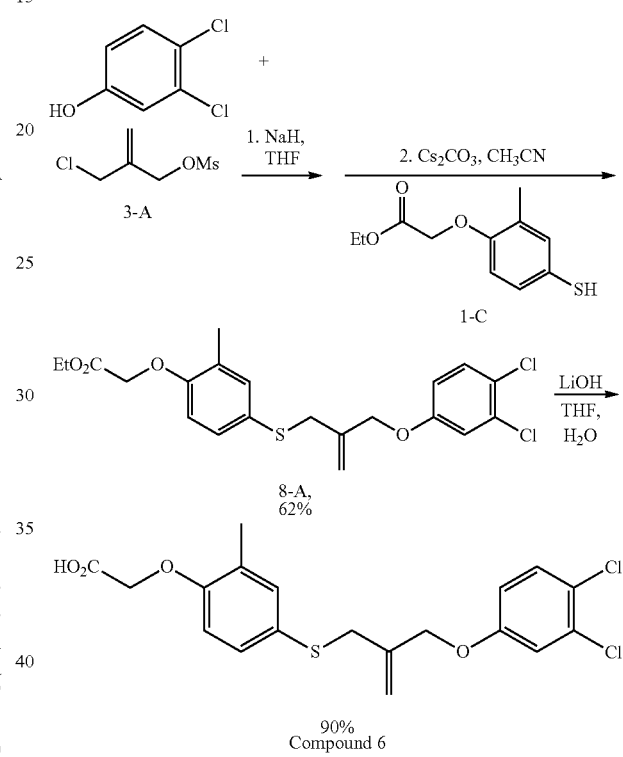

{4-[2-(3,4-Dichloro-phenoxymethyl)-allylsulfanyl]-2-methyl-phenoxy}-acetic acid ethyl ester Following general procedure 4 gave 8-A (62%); $^1$H NMR (400 MHz, CDCl$_3$) δ 7.28 (d, J=8.9 Hz, 1H), 7.20 (d, J=2.0 Hz, 1H), 7.15 (dd, J=8.4, 2.2 Hz, 1H), 6.99 (d, J=2.9 Hz, 1H), 6.74 (dd, J=8.9, 2.9 Hz, 1H), 6.59 (d, J=8.4 Hz, 1H), 5.09 (s, 1H), 4.95 (s, 1H), 4.60 (s, 2H), 4.56 (s, 2H), 4.25 (q, J=7.1 Hz, 2H), 3.53 (s, 2H), 2.24 (s, 3H), 1.28 (t, J=7.1 Hz, 3H); MS (ES) m/z: 463 (M+Na$^+$).

Compound 6

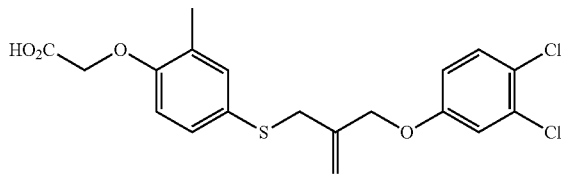

{4-[2-(3,4-Dichloro-phenoxymethyl)-allylsulfanyl]-2-methyl-phenoxy}-acetic acid

Following general procedure 2 gave Compound 6 (90%); $^1$H NMR (300 MHz, CDCl$_3$) δ 7.28 (d, J=8.9 Hz, 1H), 7.20 (s, 1H), 7.16 (dd, J=8.4, 1.9 Hz, 1H), 6.98 (d, J=2.8 Hz, 1H), 6.73 (dd, J=8.9, 2.9 Hz, 1H), 6.61 (d, J=8.4 Hz, 1H), 5.10 (s, 1H), 4.97 (s, 1H), 4.65 (s, 2H), 4.56 (s, 2H), 3.54 (s, 2H), 2.22 (s, 3H); MS (ES) m/z: 435 (M+Na$^+$).

Example VII

9-A

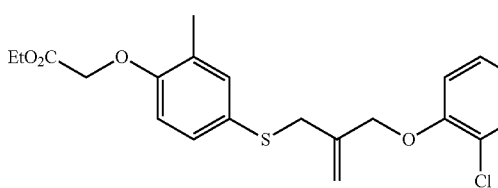

{4-[2-(2,4-Dichloro-phenoxymethyl)-allylsulfanyl]-2-methyl-phenoxy}-acetic acid ethyl ester Following general procedure 4 gave the title compound 9-A (56%); $^1$H NMR (400 MHz, CDCl$_3$) δ 7.34 (d, J=2.5 Hz, 1H), 7.19 (s, 1H), 7.19 (s, 1H), 7.16 (m, 1H), 7.13 (dd, J=8.6, 2.4 Hz, 1H), 6.81 (d, J=8.8 Hz, 1H), 6.58 (d, J=8.4 Hz, 1H), 5.15 (s, 1H), 4.98 (s, 1H), 4.63 (s, 2H), 4.59 (s, 2H), 4.25 (q, J=7.1 Hz, 2H), 3.59 (s, 2H), 2.23 (s, 3H), 1.28 (t, J=7.1 Hz, 3H); MS (ES) m/z: 463 (M+Na$^+$). Anal. Calcd for C21H22Cl2O4S: C, 57.15; H, 5.02. Found: C, 57.52; H, 4.92.

Compound 7

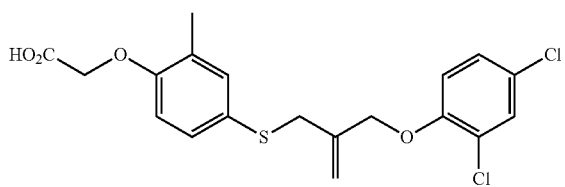

{4-[2-(2,4-Dichloro-phenoxymethyl)-allylsulfanyl]-2-methyl-phenoxy}-acetic acid

Following general procedure 2 gave Compound 7 (91%); $^1$H NMR (400 MHz, CDCl$_3$) δ 7.35 (d, J=2.5 Hz, 1H), 7.20 (s, 1H), 7.18-7.12 (m, 2H), 6.81 (d, J=8.8 Hz, 1H), 6.61 (d, J=8.4 Hz, 1H), 5.16 (s, 1H), 5.01 (s, 1H), 4.66 (s, 2H), 4.64 (s, 2H), 3.60 (s, 2H), 2.23 (s, 3H); MS (ES) m/z: 435 (M+Na$^+$).

Example VIII

10-A

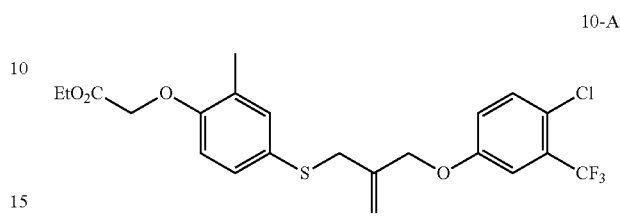

{4-[2-(4-Chloro-3-trifluoromethyl-phenoxymethyl)-allylsulfanyl]-2-methyl-phenoxy}-acetic acid ethyl ester Following general procedure 4 gave the title compound 10-A (83%); $^1$H NMR (400 MHz, CDCl$_3$) δ 7.36 (d, J=8.8 Hz, 1H), 7.21 (d, J=3.0 Hz, 1H), 7.20 (d, J=8.0 Hz, 1H), 7.15 (dd, J=8.4, 2.1 Hz, 1H), 6.97 (dd, J=8.8, 2.9 Hz, 1H), 6.59 (d, J=8.4 Hz, 1H), 5.11 (s, 1H), 4.97 (s, 1H), 4.61 (s, 2H), 4.60 (s, 2H), 4.25 (q, J=7.1 Hz, 2H), 3.55 (s, 2H), 2.23 (s, 3H), 1.28 (t, J=7.1 Hz, 3H), MS (ES) m/z: 497 (M+Na$^+$). Anal. Calcd for C$_{22}$H$_{22}$ClF$_3$O$_4$S: C, 55.64; H, 4.67. Found: C, 55.76; H, 4.52.

Compound 8

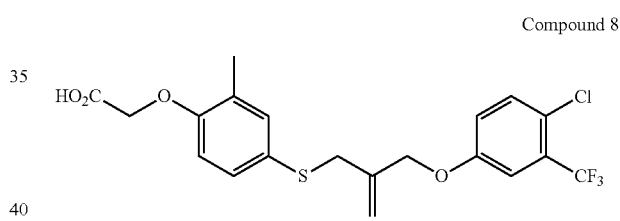

{4-[2-(4-Chloro-3-trifluoromethyl-phenoxymethyl)-allylsulfanyl]-2-methyl-phenoxy}-acetic acid Following general procedure 2 gave Compound 8 (86%); $^1$H NMR (300 MHz, CDCl$_3$) δ 7.35 (d, J=8.8 Hz, 1H), 7.21 (s, 1H), 7.20 (s, 1H), 7.16 (dd, J=8.5, 2.1 Hz, 1H), 6.96 (dd, J=8.8, 3.0 Hz, 1H), 6.61 (d, J=8.4 Hz, 1H), 5.12 (d, J=0.9 Hz, 1H), 4.99 (s, 1H), 4.65 (s, 2H), 4.61 (s, 2H), 3.56 (s, 2H), 2.23 (s, 3H); MS (ES) m/z: 469 (M+Na$^+$).

Example IX

11-A

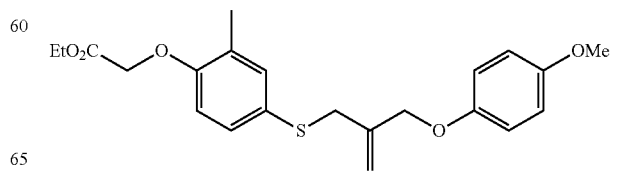

{4-[2-(4-Methoxy-phenoxymethyl)-allylsulfanyl]-2-methyl-phenoxy}-acetic acid ethyl ester Following general procedure 4 gave the title compound 11-A (60%); $^1$H NMR (300 MHz, CDCl$_3$) δ 7.19 (d, J=1.8 Hz, 1H), 7.14 (dd, J=8.4, 2.2 Hz, 1H), 6.85-6.77 (m, 4H), 6.58 (d, J=8.4 Hz, 1H), 5.11 (s, 1H), 4.57 (s, 2H), 4.54 (s, 2H), 4.23 (q, J=7.1 Hz, 2H), 3.73 (s, 3H), 3.55 (s, 2H), 2.23 (s, 3H), 1.26 (t, J=7.1 Hz, 3H); MS (ES) m/z: 425 (M+Na$^+$).

Compound 9

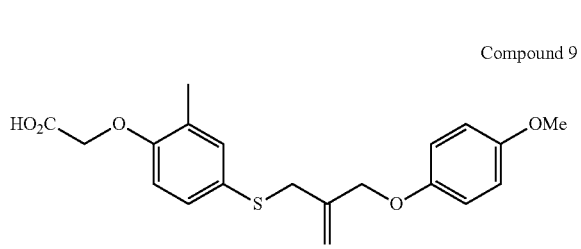 [SMILES: C=C(COc1ccc(OC)cc1)CSc1ccc(OCC(=O)O)c(C)c1]

{4-[2-(4-Methoxy-phenoxymethyl)-allylsulfanyl]-2-methyl-phenoxy}-acetic acid Following general procedure 2 gave Compound 9 (90%); MS (ES) m/z: 397 (M+Na$^+$).

Example X

12-A

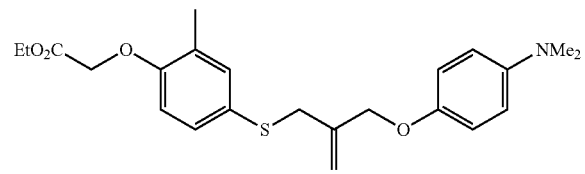

{4-[2-(4-Dimethylamino-phenoxymethyl)-allylsulfanyl]-2-methyl-phenoxy}-acetic acid ethyl ester Following general procedure 4 gave the title compound 12-A (80%); $^1$H NMR (300 MHz, CDCl$_3$) δ 7.20 (s, 1H), 7.16 (dd, J=8.4, 2.2 Hz, 1H), 6.73 (d, J=9.0 Hz, 2H), 6.60 (d, J=8.4 Hz, 1H), 6.85 (d, J=9.1 Hz, 2H), 5.13 (d, J=1.1 Hz, 1H), 4.94 (s, 1H), 4.60 (s, 2H), 4.56 (s, 2H), 4.25 (q, J=7.1 Hz, 2H), 3.57 (s, 2H), 2.87 (s, 6H), 2.24 (s, 3H), 1.29 (t, J=7.1 Hz, 3H); MS (ES) m/z: 416 (M+Na$^+$).

Compound 10

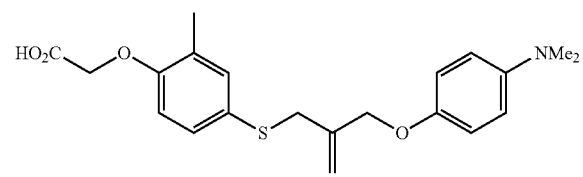

{4-[2-(4-Dimethylamino-phenoxymethyl)-allylsulfanyl]-2-methyl-phenoxy}-acetic acid Following general procedure 2 gave Compound 10 (85%); $^1$H NMR (400 MHz, MeOH-d$_4$) δ 7.17 (s, 1H), 7.15 (dd, J=8.5, 2.1 Hz, 1H), 6.92 (d, J=9.1 Hz, 2H), 6.82 (d, J=9.2 Hz, 2H), 6.69 (d, J=8.4 Hz, 1H), 5.04 (d, J=1.3 Hz, 1H), 4.90 (s, 1H), 4.56 (s, 2H), 4.54 (s, 2H), 3.55 (s, 2H), 2.88 (s, 6H), 2.18 (s, 3H); MS (ES) m/z: 388 (M+H$^+$).

Example XI

Scheme 13

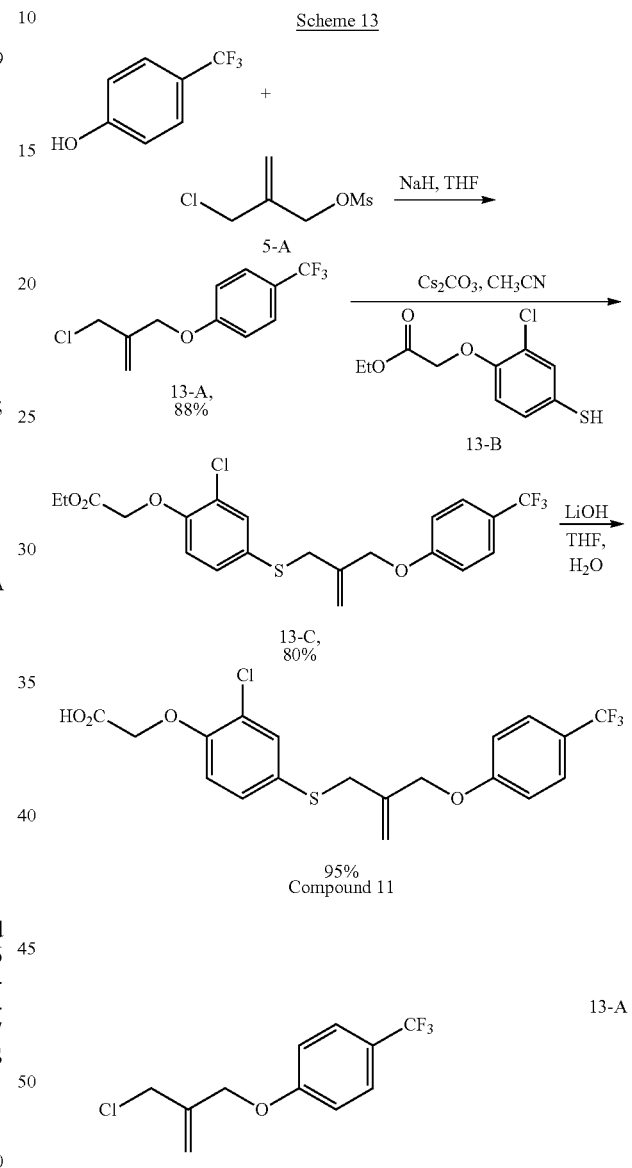

1-(2-Chloromethyl-allyloxy)-4-trifluoromethyl-benzene

To a suspension of NaH (60 mg, 1.5 mmol; 60% in mineral oil) in THF (2 mL) was added a solution of 4-trifluoromethylphenol (162 mg, 1.00 mmol) in THF (1 mL). After stirring at room temperature for 15 min, the mixture was transferred to a solution of methanesulfonic acid 2-chloromethylallyl ester 5-A (185 mg, 1.00 mmol) in THF (3 mL) at 0° C. The mixture was heated at 60-70° C. for 3 h and 40-50° C. overnight, diluted with water, and extracted with EtOAc. The extracts were dried, concentrated, and column chromatographed (EtOAc/hexane: 1/10) to provide 221 mg (88%) of 13-A; ¹H NMR (300 MHz, CDCl₃) δ 7.55 (d, J=8.6 Hz, 2H), 7.00 (d, J=8.6 Hz, 2H), 5.42 (s, 1H), 5.37 (s, 1H), 4.68 (s, 2H), 4.19 (s, 2 H).

13-C

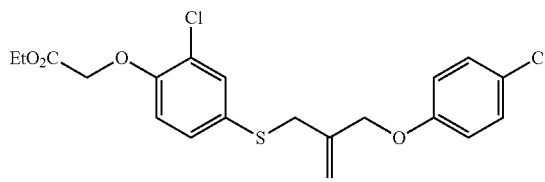

{2-Chloro-4-[2-(4-trifluoromethyl-phenoxymethyl)-allylsulfanyl]-phenoxy}-acetic acid ethyl ester Replacing (4-mercapto-2-methyl-phenoxy)acetic acid ethyl ester 1-C with (2-chloro-4-mercapto-phenoxy)acetic acid ethyl ester 13-B and following general procedure 3 gave 13-C (80%); ¹H NMR (400 MHz, CDCl₃) δ 7.53 (d, J=8.8 Hz, 2H), 7.43 (d, J=2.3 Hz, 1H), 7.20 (dd, J=8.5, 2.3 Hz, 1H), 6.96 (d, J=8.8 Hz, 2H), 6.73 (d, J=8.6 Hz, 1H), 5.17 (s, 1H), 5.01 (s, 1H), 4.66 (s, 2H), 4.65 (s, 2H), 4.26 (q, J=7.1 Hz, 2H), 3.59 (s, 2H), 1.28 (t, J=7.1 Hz, 3H); MS (ES) m/z: 483 (M+Na⁺).

Compound 11

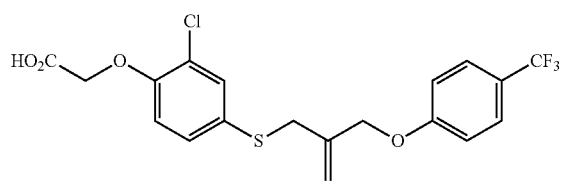

{2-Chloro-4-[2-(4-trifluoromethyl-phenoxymethyl)-allylsulfanyl]-phenoxy}-acetic acid Following general procedure 2 gave Compound 11 (95%); ¹H NMR (300 MHz, CDCl₃) δ 7.54 (d, J=8.6 Hz, 2H), 7.44 (d, J=2.2 Hz, 1H), 7.22 (dd, J=8.5, 2.2 Hz, 1H), 6.96 (d, J=8.6 Hz, 2H), 6.77 (d, J=8.5 Hz, 1H), 5.19 (s, 1H), 5.04 (s, 1H), 4.71 (s, 2H), 4.65 (s, 2H), 3.61 (s, 2H); MS (ES) m/z: 455 (M+Na⁺). Anal. Calcd for C₁₉H₁₆ClF₃O₄S: C, 52.72; H, 3.72. Found: C, 52.79; H, 3.59.

Example XII

Scheme 14

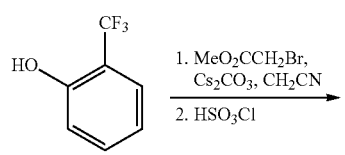

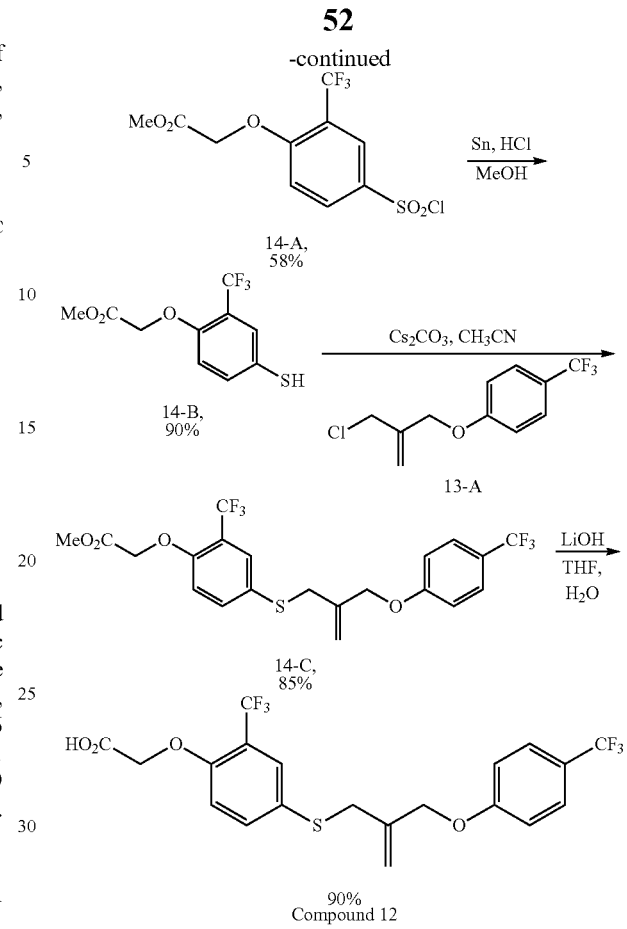

(4-Chlorosulfonyl-2-trifluoromethyl-phenoxy)-acetic acid methyl ester

A mixture of 2-trifluoromethylphenol (4.66 g, 28.8 mmol), bromoacetic acid methyl ester (4.01 g, 26.2 mmol), and Cs₂CO₃ (18.8 g, 57.6 mmol) in CH₃CN (50 mL) was stirred at room temperature overnight, filtered, and washed with CH₃CN. The filtrate was concentrated, the residue was dissolved in Et₂O and washed with 1 N NaOH (×3) and H₂O (×2). The organic phase was dried and concentrated to give 5.87 g (87%) of the alkylated product, (2-trifluoromethylphenoxy)acetic acid methyl ester.

To a flask containing chlorosulfonic acid (5.93 g, 50.9 mmol) at 0° C. was slowly added the above prepared compound (2.65 g, 11.3 mmol). After the resulting solution was stirred at 0° C. for 30 min and room temperature for 2 h, it was poured into ice with stirring. The precipitated solid was filtered, dissolved in CH₂Cl₂, washed with brine, dried, and concentrated to provide 2.50 g (66%) of 14-A; ¹H NMR (300 MHz, CDCl₃) δ 8.28 (d, J=2.3 Hz, 1H), 8.17 (dd, J=9.0, 2.4 Hz, 1H), 7.04 (d, J=9.0 Hz, 1H), 4.90 (s, 2H), 3.84 (s, 3H); MS (ES) m/z: 355 (M+Na⁺).

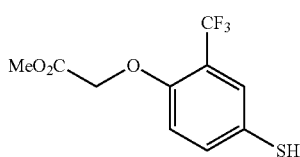

14-B (4-Mercapto-2-trifluoromethyl-phenoxy)-acetic acid methyl ester

To a solution of 14-A (2.30 g, 6.91 mmol) in MeOH (12 mL) was added a solution of 4 M HCl in dioxane (12 mL, 48 mmol) followed by tin (4.10 g, 34.5 mmol) powder portionwise. The resulting mixture was refluxed for 3 h, poured into ice/$CH_2Cl_2$. The aqueous layer was separated and extracted with $CH_2Cl_2$. The organic extracts were dried and concentrated to give 14-B; $^1$H NMR (300 MHz, $CDCl_3$) δ 8.28 (d, J=2.3 Hz, 1H), 7.41 (dd, J=8.6, 2.3 Hz, 1H), 6.78 (d, J=8.6 Hz, 1H), 4.70 (s, 2H), 3.79 (s, 3H), 3.47 (s, 1H); MS (ES) m/z: 289 (M+Na+).

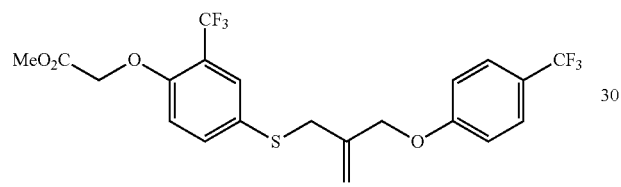

14-C

{2-Trifluoromethyl-4-[2-(4-trifluoromethyl-phenoxymethyl)-allylsulfanyl]-phenoxy}-acetic acid methyl ester Replacing (4-mercapto-2-methyl-phenoxy)acetic acid ethyl ester 1-C with (4-mercapto-2-trifluoromethyl-phenoxy)-acetic acid methyl ester 14-B and following general procedure 3 gave 14-C (85%); $^1$H NMR (400 MHz, $CDCl_3$) δ 7.63 (d, J=2.2 Hz, 1H), 7.53 (d, J=8.8 Hz, 2H), 7.47 (dd, J=8.6, 2.2 Hz, 1H), 6.96 (d, J=8.8 Hz, 2H), 6.77 (d, J=8.6 Hz, 1H), 5.19 (s, 1H), 5.01 (s, 1H), 4.70 (s, 2H), 4.65 (s, 2H), 3.79 (s, 3H), 3.61 (s, 2H); MS (ES) m/z: 503 (M+Na+).

Compound 12

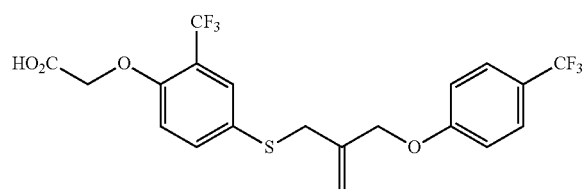

{2-Trifluoromethyl-4-[2-(4-trifluoromethyl-phenoxymethyl)-allylsulfanyl]-phenoxy}-acetic acid Following general procedure 2 gave Compound 12 (90%); $^1$H NMR (300 MHz, $CDCl_3$) δ 7.63 (d, J=2.1 Hz, 1H), 7.53 (d, J=8.7 Hz, 2H), 7.48 (dd, J=8.6, 2.2 Hz, 1H), 6.95 (d, J=8.7 Hz, 2H), 6.80 (d, J=8.6 Hz, 1H), 5.19 (s, 1H), 5.02 (s, 1H), 4.71 (s, 2H), 4.65 (s, 2H), 3.61 (s, 2H); MS (ES) m/z: 489 (M+Na+). Anal. Calcd for $C_{20}H_{16}F_6O_4S$: C, 52.72; H, 3.73. Found: C, 52.53; H, 3.52.

Example XIII

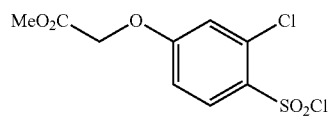

15-A (3-Chloro-4-chlorosulfonyl-phenoxy)-acetic acid methyl ester

Following the same procedure as in the preparation of 14-A provided 15-A (75%); $^1$H NMR (300 MHz, $CDCl_3$) δ 8.09 (d, J=2.3 Hz, 1H), 7.13 (d, J=2.6 Hz, 1H), 6.92 (dd, J=9.1, 2.6 Hz, 1H), 4.75 (s, 2H), 3.84 (s, 3H); MS (ES) m/z: 321 (M+Na+).

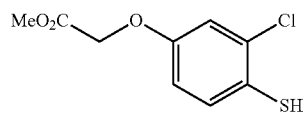

15-B (3-Chloro-4-mercapto-phenoxy)-acetic acid methyl ester

Following the same procedure as in the preparation of 14-B provided the title compound 15-B (94%); $^1$H NMR (300 MHz, $CDCl_3$) δ 7.27 (d, J=8.6 Hz, 1H), 6.97 (d, J=2.7 Hz, 1H), 6.74 (dd, J=8.7, 2.7 Hz, 1H), 4.60 (s, 2H), 3.81 (s, 3H), 3.71 (d, J=5.6 Hz, 1H); MS (ES) m/z: 231 (M−H+).

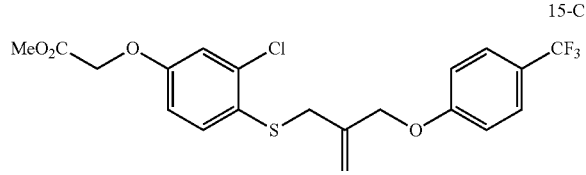 [SMILES: C=C(COc1ccc(C(F)(F)F)cc1)CSc1ccc(OCC(=O)OC)cc1Cl]

15-C

{3-Chloro-4-[2-(4-trifluoromethyl-phenoxymethyl)-ailysulfanyl]-phenoxy}-acetic acid methyl ester Replacing (4-mercapto-2-methyl-phenoxy)acetic acid ethyl ester 1-C with (3-chloro-4-mercapto-phenoxy)-acetic acid methyl ester 15-B and following general procedure 3 gave the title compound 15-C (88%); $^1$H NMR (300 MHz, $CDCl_3$) δ 7.53 (d, J=8.6 Hz, 2H), 7.35 (d, J=8.7 Hz, 1H), 6.98-6.95 (m, 3H), 6.73 (dd, J=8.7, 2.8 Hz, 1H), 5.14 (d, J=1.0 Hz, 1H), 5.00 (d, J=0.8 Hz, 1H), 4.66 (s, 2H), 4.59 (s, 2H), 3.81 (s, 3H), 3.62 (s, 2H); MS (ES) m/z: 469 (M+Na+). Anal. Calcd for $C_{20}H_{18}ClF_3O_4S$: C, 53.76; H, 4.06. Found: C, 54.05; H, 3.78.

Compound 13

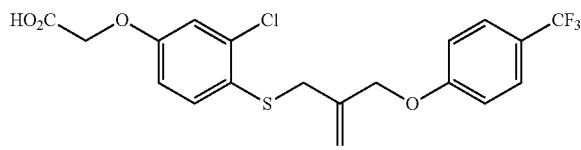

{3-Chloro-4-[2-(4-trifluoromethyl-phenoxymethyl)-allylsulfanyl]-phenoxy}-acetic acid Following general procedure 2 gave Compound 13 (95%); $^1$H NMR (300 MHz, CDCl$_3$) δ 7.52 (d, J=8.7 Hz, 2H), 7.34 (d, J=8.7 Hz, 1H), 6.99-6.94 (m, 3H), 6.74 (dd, J=8.7, 2.6 Hz, 1H), 5.15 (d, J=0.7 Hz, 1H), 5.00 (s, 1H), 4.66 (s, 2H), 4.62 (s, 2H), 3.62 (s, 2H); MS (ES) m/z: 455 (M+Na$^+$).

Example XIV

16-A

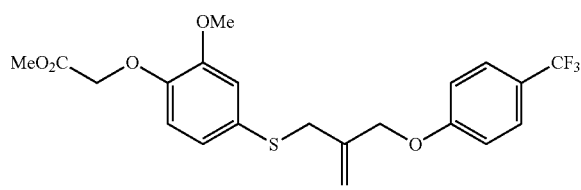

{2-Methoxy-4-[2-(4-trifluoromethyl-phenoxymethyl)-allylsulfanyl]-phenoxy}-acetic acid methyl ester Following general procedure 3 gave the title compound 16-A (87%); $^1$H NMR (300 MHz, CDCl$_3$) δ 7.53 (d, J=8.6 Hz, 2H), 7.03 (dd, J=8.4, 2.1 Hz, 1H), 6.97 (d, J=8.6 Hz, 2H), 6.91 (d, J=2.1 Hz, 1H), 6.79 (d, J=8.4 Hz, 1H), 5.13 (d, J=1.0 Hz, 1H), 4.96 (s, 1H), 4.65 (s, 4H), 3.85 (s, 3H), 3.78 (s, 3H), 3.55 (s, 2H); MS (ES) m/z: 465 (M+Na$^+$).

Compound 14

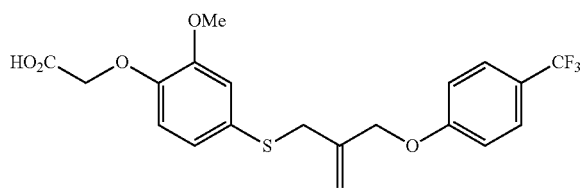

{2-Methoxy-4-[2-(4-trifluoromethyl-phenoxymethyl)-allylsulfanyl]-phenoxy}-acetic acid Following general procedure 2 gave Compound 14 (94%); $^1$H NMR (300 MHz, MeOH-d$_4$) δ 7.54 (d, J=8.6 Hz, 2H), 7.04 (d, J=8.6, 2 H), 7.03-6.99 (m, 2H), 6.88 (d, J=8.3 Hz, 1H), 5.11 (s, 1H), 4.97 (s, 1H), 4.69 (s, 2H), 4.55 (s, 2H), 3.81 (s, 3H), 3.60 (s, 2H); MS (ES) m/z: 451 (M+Na$^+$).

Example XV

Scheme 17

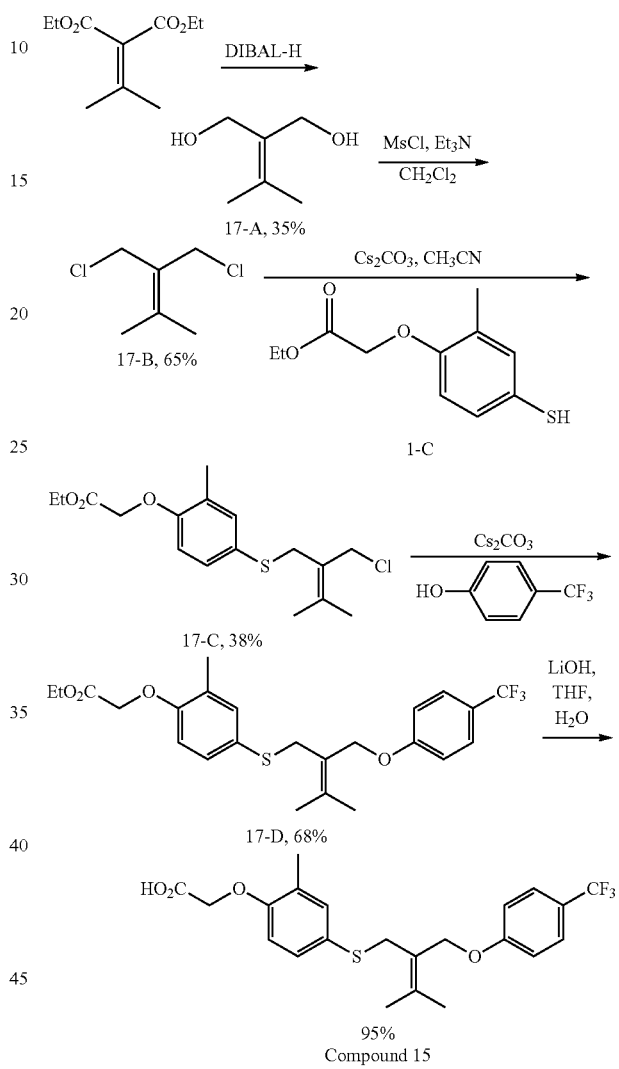

17-A

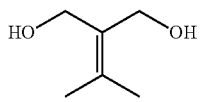

2-Isopropylidene-propane-1,3-diol

To a solution of diisobutylaluminum hydride (1.0 M in CH$_2$Cl$_2$, 6.75 mL, 6.75 mmol) in CH$_2$Cl$_2$ (5 mL) at −78° C. was added a solution of 2-isopropylidene malonic acid diethyl ester (300 mg, 1.50 mmol) in CH$_2$Cl$_2$ (2 mL). The reaction mixture was allowed to warmed up to 0° C., stirred at this temperature for 1 h, and quenched with MeOH (8 mL). The precipitated solid was filtered through Celite and washed with CH$_2$Cl$_2$/MeOH. The filtrate was concentrated to give 61 mg (35%) of 17-A; $^1$H NMR (300 MHz, CDCl$_3$) δ 4.27 (s, 4H), 3.25 (brs, 2H), 1.78 (s, 6H).

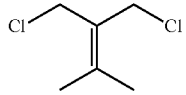

17-B

1-Chloro-2-chloromethyl-3-methyl-but-2-ene

To a solution of 17-A (200 mg, 1.72 mmol) in CH$_2$Cl$_2$ (3 mL) at 0° C. were added Et$_3$N (0.960 mL, 6.90 mmol) and methanesulfonyl chloride (592 mg, 5.17 mmol). The mixture was allowed to warm up to room temperature, stirred at the same temperature for 3 h, and diluted with saturated NaHCO$_3$. The organic layer was separated and the aqueous layer was extracted with CH$_2$Cl$_2$. The combined organic phases were dried, concentrated, and column chromatographed (EtOAc/hexane: 1/7) to provide 171 mg (65%) of 17-B; $^1$H NMR (300 MHz, CDCl$_3$) δ 4.26 (s, 4H), 1.87 (s, 6H).

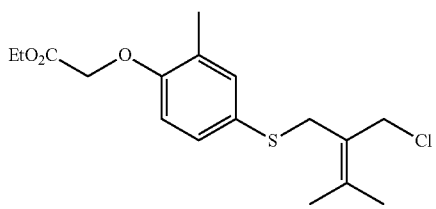

17-C

[4-(2-Chloromethyl-3-methyl-but-2-enylsulfanyl)-2-methyl-phenoxy]-acetic acid ethyl ester Following general procedure 3 gave 17-C (38%); $^1$H NMR (300 MHz, CDCl$_3$) δ 7.20 (s, 1H), 7.17 (dd, J=8.4, 2.1 Hz, 1H), 6.61 (d, J=8.4 Hz, 1H), 4.62 (s, 2H), 4.28 (s, 2H), 4.26 (q, J=7.1 Hz, 2H), 3.61 (s, 2H), 2.26 (s, 3H), 1.78 (s, 3H), 1.53 (s, 3H), 1.29 (t, J=7.1 Hz, 3H); MS (ES) m/z: 365 (M+Na$^+$).

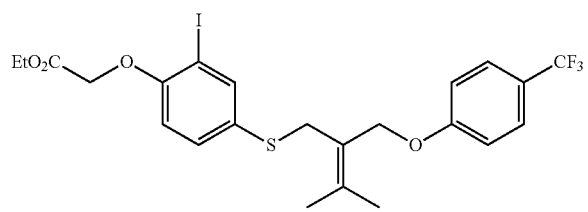

17-D

{2-Methyl-4-[3-methyl-2-(4-trifluoromethyl-phenoxymethyl)-but-2-enylsulfanyl]-phenoxy}-acetic acid ethyl ester Replacing (4-mercapto-2-methyl-phenoxy)-acetic acid ethyl ester 1-C with 4-trifluoromethyl-phenol and following general procedure 3 gave 17-D (68%); $^1$H NMR (300 MHz, CDCl$_3$) δ 7.54 (d, J=8.6 Hz, 2H), 7.20 (s, 1H), 7.17 (dd, J=8.4, 2.2 Hz, 1H), 6.97 (d, J=8.6 Hz, 2H), 6.59 (d, J=8.4 Hz, 1H), 4.65 (s, 2H), 4.60 (s, 2H), 4.25 (q, J=7.1 Hz, 2H), 3.65 (s, 2H), 2.23 (s, 3H), 1.78 (s, 3H), 1.59 (s, 3H), 1.29 (t, J=7.1 Hz, 3H); MS (ES) m/z: 491 (M+Na$^+$). Anal. Calcd for C$_{24}$H$_{27}$F$_3$O$_4$S: C, 61.52; H, 5.81. Found: C, 61.69; H, 5.99.

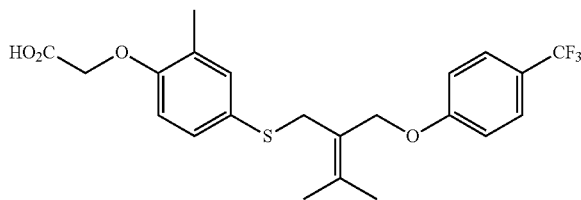

Compound 15

{2-Methyl-4-[3-methyl-2-(4-trifluoromethyl-phenoxymethyl)-but-2-enylsulfanyl]-phenoxy}-acetic acid Following general procedure 2 gave Compound 15 (95%); $^1$H NMR (400 MHz, CDCl$_3$) δ 7.52 (d, J=8.6 Hz, 2H), 7.18 (s, 1H), 7.15 (d, J=8.5 Hz, 1H), 6.96 (d, J=8.6 Hz, 2H), 6.57 (d, J=8.1 Hz, 1H), 4.64 (s, 2H), 4.56 (s, 2H), 3.65 (s, 2H), 2.18 (s, 3H), 1.78 (s, 3H), 1.60 (s, 3H); MS (ES) m/z: 463 (M+Na$^+$).

Example XVI

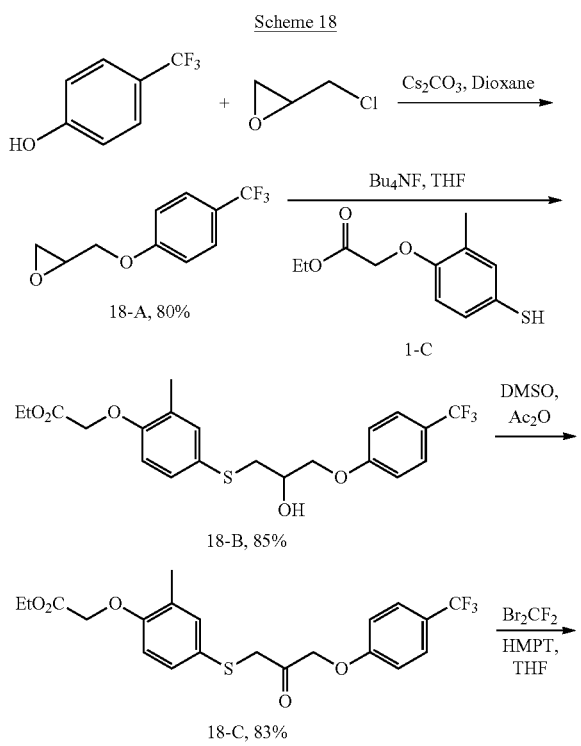

Scheme 18

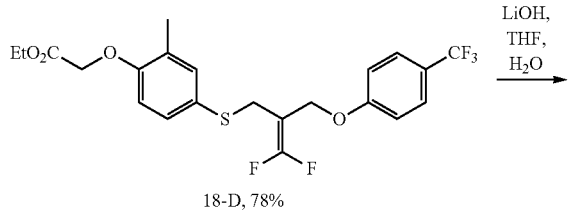

18-D, 78%

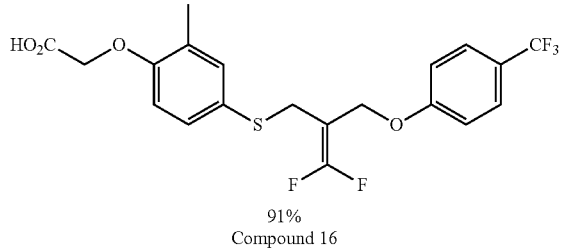

91%
Compound 16

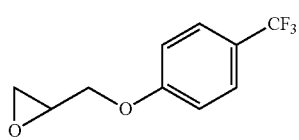

2-(4-Trifluoromethyl-phenoxymethyl)-oxirane

A mixture of 4-trifluoromethylphenol g, 48.1 mmol), 2-chloromethyloxirane (11.2 g, 121 mmol), and $Cs_2CO_3$ (15.7 g, 48.2 mmol) in dioxane (8 mL) was refluxed for 3-4 h and then allowed to cool to room temperature. Water and $Et_2O$ were added, the organic phase was separated, and the aqueous phase was extracted with $Et_2O$. The combined organic layers were dried, concentrated, and column chromatographed ($CH_2Cl_2$/hexane: 1/1) to provide 8.40 g (80%) of 18-A; $^1$H NMR (300 MHz, CDCl$_3$) δ 7.55 (d, J=8.5 Hz, 2H), 6.99 (d, J=8.5 Hz, 2H), 4.29 (dd, J=11.1, 3.0 Hz, 1H), 3.98 (dd, J=11.1, 5.8 Hz, 1H), 3.37 (m, 1H), 2.93 (m, 1H), 2.77 (dd, J=4.9, 2.6 Hz, 1H).

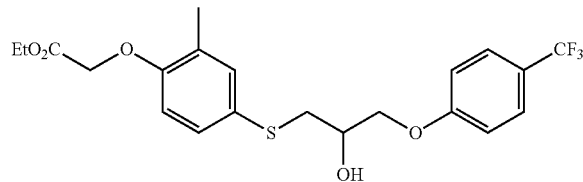

{4-[2-Hydroxy-3-(4-trifluoromethyl-phenoxy)-propylsulfanyl]-2-methyl-phenoxy}-acetic acid ethyl ester To a mixture of 18-A (2.57 g, 11.8 mmol) and (4-mercapto-2-methyl-phenoxy)acetic acid ethyl ester 1-C (4.00 g, 17.7 mmol) in THF (20 mL) was added 1.0 M tetrabutylammonium fluoride in THF (0.44 mL, 0.44 mmol). The reaction mixture was stirred at room temperature for 1.5 h, heated at 60° C. for 1 h, concentrated, and purified by column chromatography ($CH_2Cl_2$) to give 4.45 g (85%) of 18-B; $^1$H NMR (400 MHz, CDCl$_3$) δ 7.50 (d, J=8.9 Hz, 2H), 7.25 (d, J=2.2 Hz, 1H), 7.21 (dd, J=8.4, 2.3 Hz, 1H), 6.89 (d, J=8.8 Hz, 2H), 6.58 (d, J=8.4 Hz, 1H), 4.58 (s, 2H), 4.24 (q, J=7.1 Hz, 2H), 4.05-4.00 (m, 3H), 3.13 (dd, J=13.7, 5.1 Hz, 1H), 3.04 (dd, J=13.9, 6.5 Hz, 1H), 2.92 (d, J=4.2 Hz, 1H), 2.23 (s, 3H), 1.28 (t, J=7.1 Hz, 3H); MS (ES) m/z: 467 (M+Na$^+$).

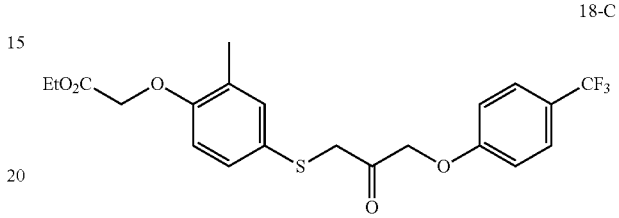

{2-Methyl-4-[2-oxo-3-(4-trifluoromethyl-phenoxy)-propylsulfanyl]-phenoxy}-acetic acid ethyl ester A reaction mixture of 18-B (1.08 g, 2.43 mmol), Ac$_2$O (2.56 mL, 27.2 mmol), and DMSO (3.84 mL) was stirred at room temperature for 24 h, and diluted with saturated NaHCO$_3$ and Et$_2$O. The organic phase was separated, washed with water (×3), dried, and column chromatographed (EtOAc/hexane: 1/4) to give 892 mg (83%) of 18-C; $^1$H NMR (300 MHz, CDCl$_3$) δ 7.53 (d, J=8.6 Hz, 2H), 7.24 (d, J=2.0 Hz, 1H), 7.20 (dd, J=8.4, 2.3 Hz, 1H), 6.88 (d, J=8.6 Hz, 2H), 6.61 (d, J=8.4 Hz, 1H), 4.77 (s, 2H), 4.60 (s, 2H), 4.25 (q, J=7.1 Hz, 2H), 3.72 (s, 2H), 2.24 (s, 3H), 1.29 (t, J=7.1 Hz, 3H); MS (ES) m/z: 465 (M+Na$^+$).

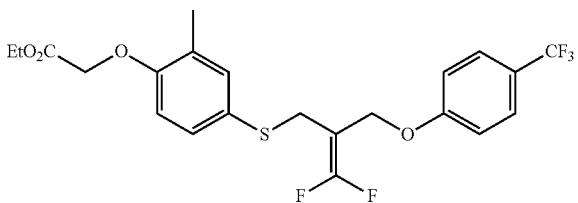

{4-[3,3-Difluoro-2-(4-trifluoromethyl-phenoxymethyl)-allylsulfanyl]-2-methyl-phenoxy}-acetic acid ethyl ester To a flask containing THF (3 mL) at 0° C. was injected Br$_2$CF$_2$ (0.091 mL, 1.0 mmol) followed by HMPT (0.364 mL, 2.00 mmol). The mixture was allowed to warm up to room temperature, and a solution of 18-C (221 mg, 0.500 mmol) in THF (2 mL) was added. After stirring overnight, the mixture was diluted with water and extracted with EtOAc. The extracts were dried, concentrated, and chromatographed (EtOAc/hexane: 1/9) to give 186 mg (78%) of 18-D; $^1$H NMR (400 MHz, CDCl$_3$) δ 7.53 (d, J=8.6 Hz, 2H), 7.22 (s, 1H), 7.18 (d, J=8.4 Hz, 1H), 6.93 (d, J=8.6 Hz, 2H), 6.59 (d, J=8.4 Hz, 1H), 4.65 (s, 2H), 4.59 (s, 2H), 4.24 (q, J=7.1 Hz, 2H), 3.57 (s, 2H), 2.23 (s, 3H), 1.27 (t, J=7.1 Hz, 3H); MS (ES) m/z: 499 (M+Na$^+$).

Compound 16

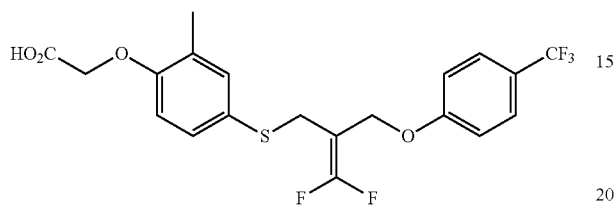

{4-[3,3-Difluoro-2-(4-trifluoromethyl-phenoxymethyl)-allylsulfanyl]-2-methyl-phenoxy}-acetic acid Following general procedure 2 gave Compound 16 (91%); $^1$H NMR (300 MHz, CDCl$_3$) δ 7.54 (d, J=8.7 Hz, 2H), 7.22 (s, 1H), 7.19 (dd, J=8.4, 2.2 Hz, 1H), 6.94 (d, J=8.7 Hz, 2H), 6.62 (d, J=8.4 Hz, 1H), 4.66 (s, 4H), 3.58 (t, J=1.7 Hz, 2H), 2.22 (s, 3H); MS (ES) m/z: 471 (M+Na$^+$).

Example XVII

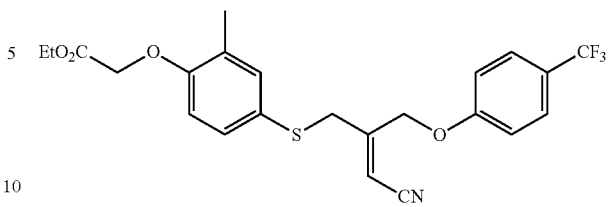

{4-[3-Cyano-2-(4-trifluoromethyl-phenoxymethyl)-allylsulfanyl]-2-methyl-phenoxy}-acetic acid ethyl ester A mixture of 18-C (80 mg, 0.18 mmol) and (triphenylphosphoranylidene) acetonitrile (109 mg, 0.362 mmol) in CH$_2$Cl$_2$ (2 mL) was stirred at room temperature overnight and concentrated. The residue was purified by column chromatography (CH$_2$Cl$_2$/hexane: 1/1) to give 76 mg (90%) of 19-A; $^1$H NMR (300 MHz, CDCl$_3$) δ 7.56 (d, J=8.7 Hz, 2H), 7.28-7.23 (m, 2H), 6.93 (d, J=8.7 Hz, 2H), 6.64 (d, J=8.4 Hz, 1H), 5.49 (s, 1H), 4.76 (d, J=1.7 Hz, 2H), 4.62 (s, 2H), 4.25 (q, J=7.1 Hz, 2H), 3.81 (s, 2H), 2.25 (s, 3H), 1.28 (t, J=7.1 Hz, 3H); MS (ES) m/z: 488 (M+Na$^+$).

Scheme 19

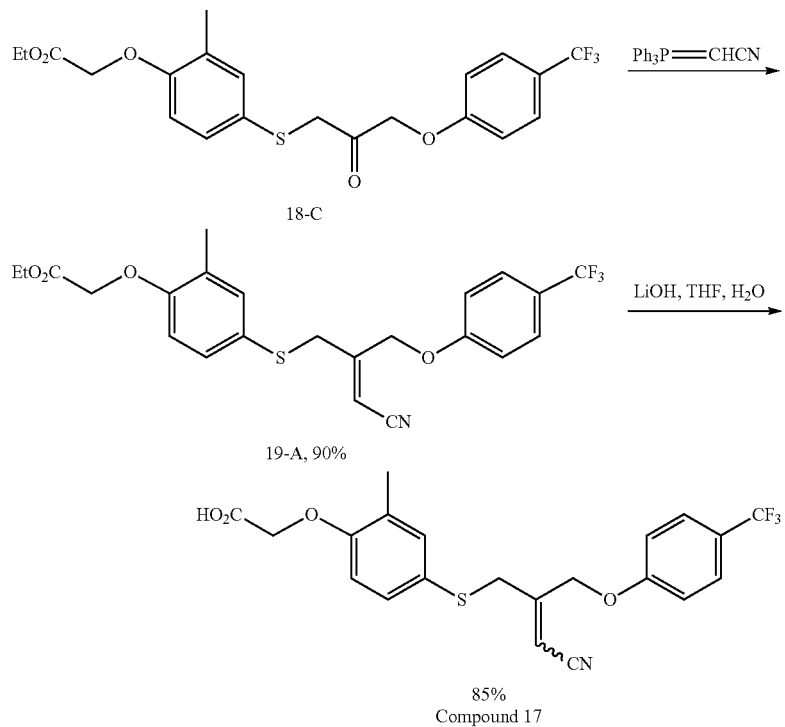

Compound 17
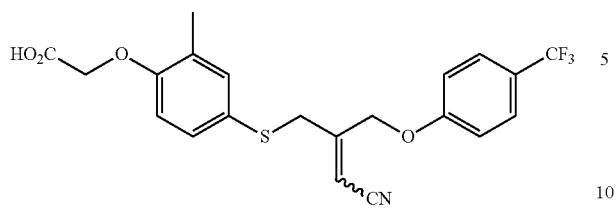
{4-[3-Cyano-2-(4-trifluoromethyl-phenoxymethyl)-allylsulfanyl]-2-methyl-phenoxy}-acetic acid
Following general procedure 2 gave Compound 17 (85%); MS (ES) m/z: 460 (M+Na⁺).
Example XVIII
Scheme 20
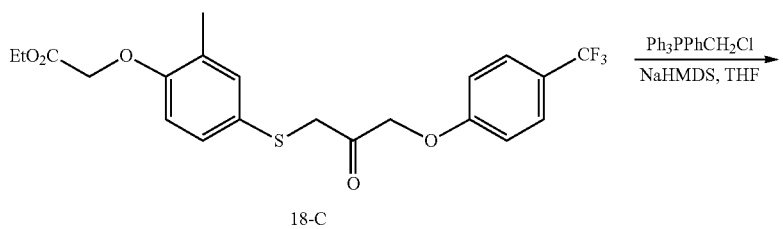
18-C
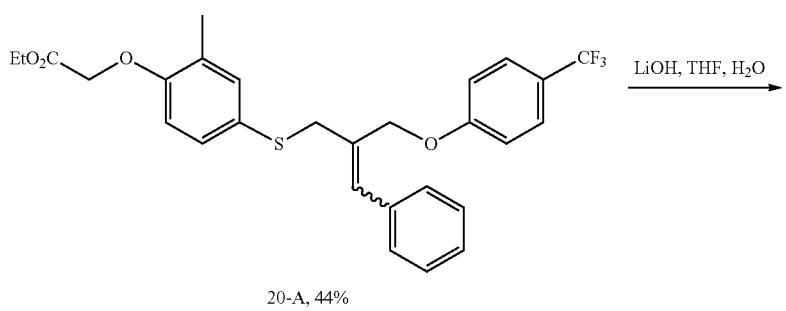
20-A, 44%
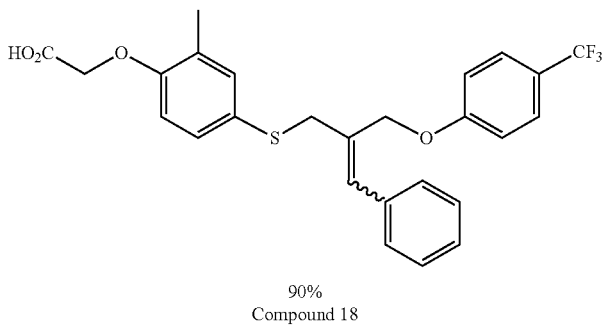
90%
Compound 18

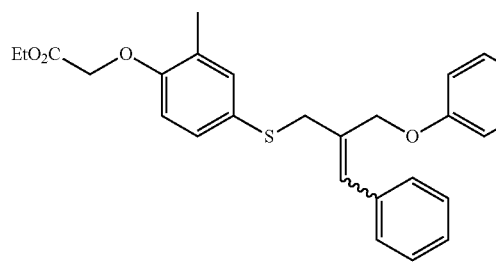

20-A

{2-Methyl-4-[3-phenyl-2-(4-trifluoromethyl-phenoxymethyl)-allylsulfanyl]-phenoxy}-acetic acid ethyl ester A solution of benzyltriphenylphosphonium chloride (98 mg, 0.25 mmol) in THF (2 mL) was treated with 1.0 M NaHMDS in THF (0.230 mL, 0.230 mmol) at 0° C. for 30 min, and then a solution of 18-C (100 mg, 0.226 mmol) in THF (1 mL) was added. The reaction mixture was allowed to warm up to room temperature, stirred for 2 h, diluted with saturated $NaHCO_3$, and extracted with $Et_2O$. The extracts were dried, concentrated, and column chromatographed (EtOAc/hexane: 1/9) to give 52 mg (44%) of 20-A as a mixture of E- and Z-isomers. Major component (58% of the mixture): $^1$H NMR (300 MHz, $CDCl_3$) δ 7.50 (d, J=8.7 Hz, 2H), 7.34-7.17 (m, 5H), 7.11-7.06 (m, 2H), 6.89 (d, J=8.7 Hz, 2H), 6.60 (d, J=8.4 Hz, 1H), 6.38 (s, 1H), 4.80 (s, 2H), 4.59 (s, 2H), 4.24 (q, J=7.1 Hz, 2H), 3.69 (s, 2H), 2.23 (s, 3H), 1.27 (t, J=7.1 Hz, 3H); MS (ES) m/z: 539 (M+Na$^+$).

Minor component (42% of the mixture): $^1$H NMR (300 MHz, $CDCl_3$) δ 7.54 (d, J=8.7 Hz, 2H), 7.34-7.17 (m, 5H), 7.11-7.06 (m, 2H), 6.99 (d, J=8.7 Hz, 2H), 6.72 (s, 1H), 6.52 (d, J=9.1 Hz, 1H), 4.76 (s, 2H), 4.57 (s, 2H), 4.25 (q, J=7.1 Hz, 2H), 3.80 (s, 2H), 2.16 (s, 3H), 1.28 (t, J=7.1 Hz, 3H).

Compound 18

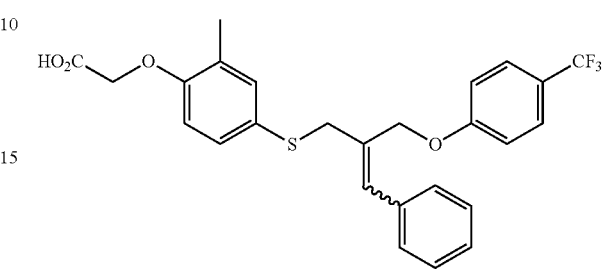

{2-Methyl-4-[3-phenyl-2-(4-trifluoromethyl-phenoxymethyl)-allylsulfanyl]-phenoxy}-acetic acid Following general procedure 2 gave Compound 18 (90%). Major component (58% of the mixture in E- and Z-isomers); $^1$H NMR (300 MHz, $CDCl_3$) δ7.46-6.40 (m, 13 H), 4.74 (s, 2H), 4.28 (s, 2H), 3.64 (s, 2H), 2.07 (s, 3H); MS (ES) m/z: 511 (M+Na$^+$).

Minor component (42% of the mixture in E- and Z-isomers); $^1$H NMR (300 MHz, $CDCl_3$) δ 7.49-6.47 (m, 13 H), 4.69 (s, 2H), 4.28 (s, 2H), 3.75 (s, 2H), 2.01 (s, 3H).

Example XIX

Scheme 21

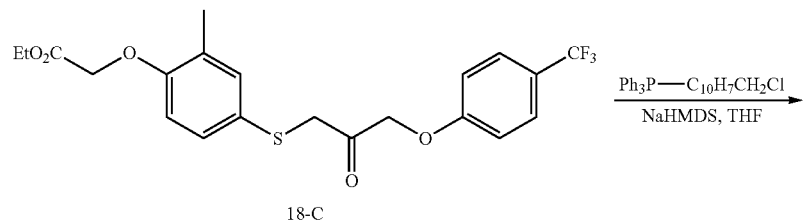

18-C

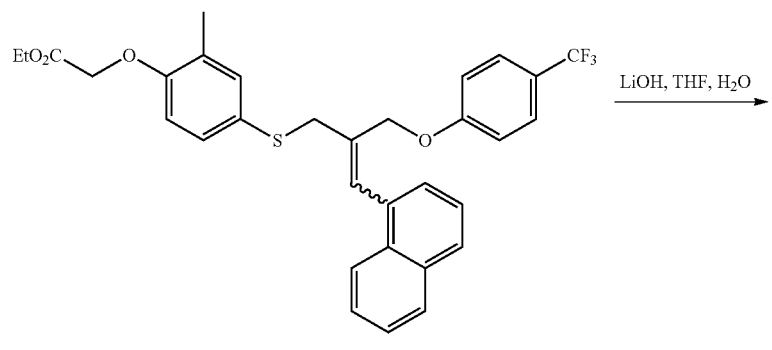

21-A, 38%

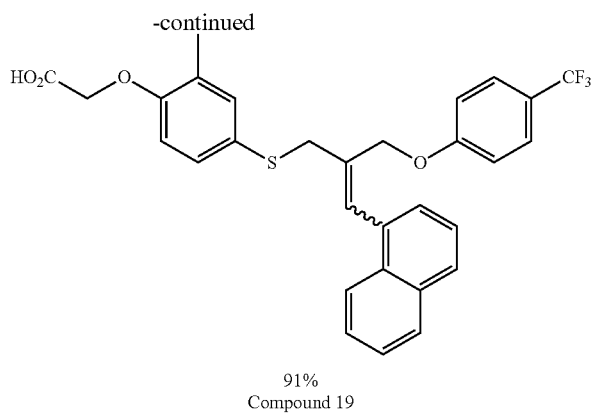

91%
Compound 19

{2-Methyl-4-[3-naphthalen-1-yl-2-(4-trifluoromethyl-phenoxymethyl)-allylsulfanyl]-phenoxy}-acetic acid Following general procedure 2 gave Compound 19 (91%) as a 1:1 mixture of E- and Z-isomers; $^1$H NMR (300 MHz, CDCl$_3$) δ 7.64-6.66 (m, 30 H), 4.76 (s, 2H), 4.56 (s, 2H), 3.92 (s, 4H), 3.68 (s, 2H), 3.57 (s, 2H), 1.97 (s, 3H), 1.72 (s, 3H); MS (ES) m/z: 537 (M−H$^+$).

Example XX

Scheme 22

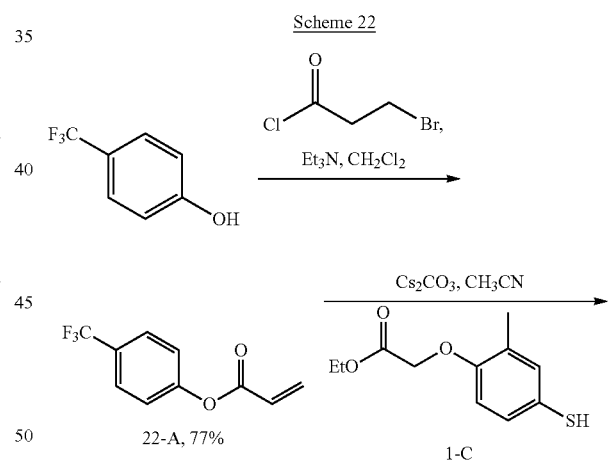

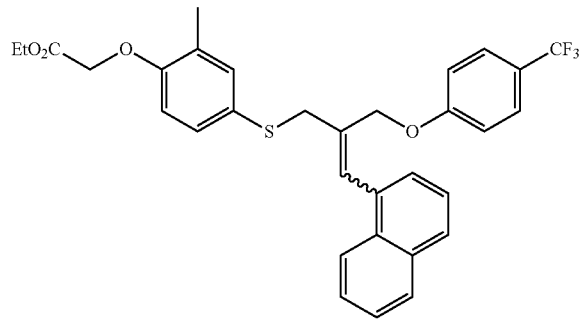

{2-Methyl-4-[3-naphthalen-1-yl-2-(4-trifluoromethyl-phenoxymethyl)-allylsulfanyl]-phenoxy}acetic acid ethyl ester A solution of (1-naphthylmethyl)triphenylphosphonium chloride (111 mg, 0.253 mmol) in THF (3 mL) was treated with 1.0 M NaHMDS in THF (0.230 mL, 0.230 mmol) at 0° C. for 20 min, and then a solution of 18-C (100 mg, 0.226 mmol) in THF (1 mL) was added. The reaction mixture was allowed to warm up to room temperature, stirred for 3 h, concentrated, and column chromatographed (EtOAc/hexane: 1/10) to give 49 mg (38%) of 21-A as a 1:1 mixture of E- and Z-isomers: $^1$H NMR (300 MHz, CDCl$_3$) δ 7.82 (d, J=8.1 Hz, 2H), 7.76 (d, J=8.2 Hz, 2H), 7.59-7.56 (m, 3H), 7.49-7.15 (m, 13 H), 7.09-7.06 (m, 3H), 6.95-6.92 (m, 2H), 6.83-6.80 (m, 3H), 6.65 (d, J=8.2 Hz, 1H), 6.29 (d, J=8.3 Hz, 1H), 4.95 (d, J=1.0 Hz, 2H), 4.71 (s, 2H), 4.61 (s, 2H), 4.47 (s, 2H), 4.25 (q, J=7.1 Hz, 2H), 4.23 (q, J=7.1 Hz, 2H), 3.84 (s, 2H), 3.72 (s, 2H), 2.26 (s, 3H), 2.00 (s, 3H), 1.28 (t, J=7.1 Hz, 3H), 1.25 (t, J=7.1 Hz, 3H); MS (ES) m/z: 589 (M+Na$^+$).

Compound 19

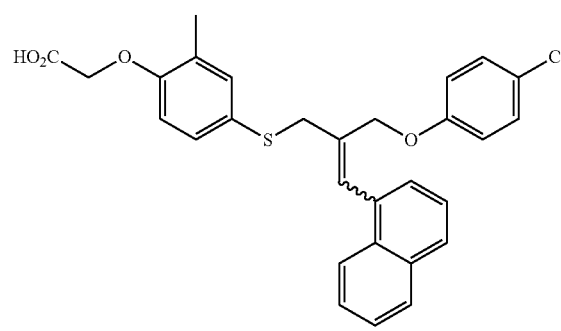

-continued

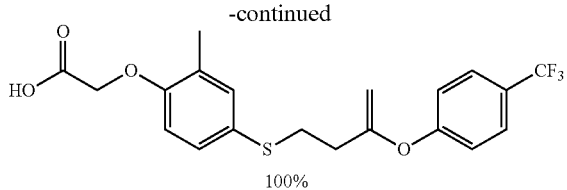

100%
Compound 20

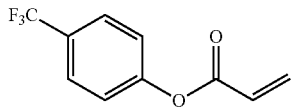

22-A

Acrylic acid 4-trifluoromethyl-phenyl ester

To a solution of trifluoromethylphenol (2.00 g, 12.3 mmol) in CH$_2$Cl$_2$ (20 mL) at 0° C. were added 3-bromopropionyl chloride (2.55 g, 14.9 mmol) and triethylamine (3.4 mL, 24 mmol). After stirring at room temperature overnight, the solvent was evaporated under reduced pressure. To the residue was added Et$_2$O, and the solid was filtered and rinsed with Et$_2$O. The filtrate was washed with water, dried, concentrated, and purified by column chromatography to give 2.04 g (77%) of 22-A as a yellow oil; $^1$H NMR (300 MHz, CDCl$_3$) δ 7.67 (d, J=8.4 Hz, 2H), 7.27 (d, J=8.3 Hz, 2H), 6.64 (dd, J=17.3, 1.2 Hz, 1H), 6.33 (dd, J=17.3, 10.4 Hz, 1H), 6.06 (dd, J=10.4, 1.2 Hz, 1H);

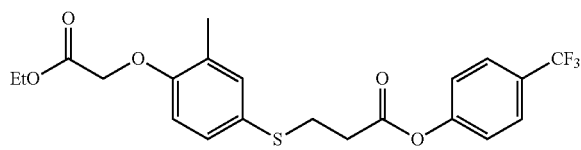

22-B 3-(4-Ethoxycarbonylmethoxy-3-methyl-phenylsulfanyl)-propionic acid 4-trifluoromethyl-phenyl ester Following general procedure 3 gave 22-B (70%, clear oil); $^1$H NMR (300 MHz, CDCl$_3$) δ 7.65 (d, J=8.5 Hz, 2H), 7.29 (s, 1H), 7.26 (dd, J=8.3, 2.3 Hz, 1H), 7.21 (d, J=8.7 Hz, 2H), 6.65 (d, J=8.3 Hz, 1H), 4.63 (s, 2H), 4.27 (q, J=7.1 Hz, 2H), 3.16 (t, J=7.2 Hz, 2H), 2.84 (t, J=7.2 Hz, 2H), 2.28 (s, 3H), 1.30 (t, J=7.1 Hz, 3H); MS (ES) m/z: 465 (M+Na$^+$).

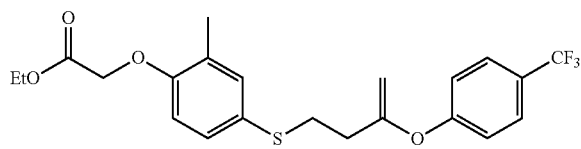

22-C

{2-Methyl-4-[3-(4-trifluoromethyl-phenoxy)-but-3-enylsulfanyl]-phenoxy}-acetic acid ethyl ester To a solution of 22-B (540 mg, 1.22 mmol) in THF (10 mL) at −20° C. was added 0.5 M Tebbe reagent (3.0 mL, 1.5 mmol) in toluene. The mixture was stirred at −20° C. for 1 h then allowed to warm up to 0° C., quenched with saturated NH$_4$Cl, and partitioned between Et$_2$O and water. The organic layer was dried, concentrated, and purified by column chromatography and preparative TLC (SiO$_2$) twice to give 44 mg (8%) of 22-C as a clear oil; $^1$H NMR (400 MHz, CDCl$_3$) δ 7.59 (d, J=8.7 Hz, 2H), 7.25 (d, J=2.2 Hz, 1H), 7.20 (dd, J=8.4, 2.3 Hz, 1H), 7.13 (d, J=8.6 Hz, 2H), 6.63 (d, J=8.4 Hz, 1H), 4.63 (s, 2H), 4.36 (d, J=2.0 Hz, 1H), 4.27 (q, J=7.1 Hz, 2H), 4.16 (d, J=2.1 Hz, 1H), 3.08 (t, J=7.5 Hz, 2H), 2.55 (t, J=7.5 Hz, 2H), 2.27 (s, 3H), 1.30 (t, J=7.1 Hz, 3H); MS (ES) m/z: 463 (M+Na$^+$).

Compound 20

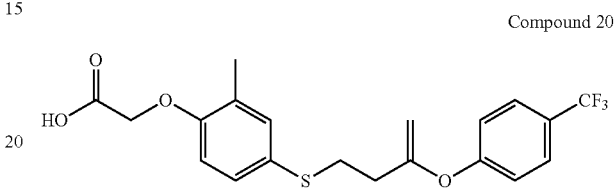

{2-Methyl-4-[3-(4-trifluoromethyl-phenoxy)-but-3-enylsulfanyl]-phenoxy}-acetic acid Following general procedure 2 gave Compound 20 (100%, clear oil); $^1$H NMR (300 MHz, CDCl$_3$) δ 7.59 (d, J=8.6 Hz, 2H), 7.24 (s, 1H), 7.20 (d, J=8.2 Hz, 1H), 7.12 (d, J=8.3 Hz, 2H), 6.66 (d, J=8.2 Hz, 1H), 4.67 (s, 2H), 4.36 (d, J=1.9 Hz, 1H), 4.16 (d, J=2.1 Hz, 1H), 3.08 (t, J=7.4 Hz, 2H), 2.54 (t, J=7.4 Hz, 2H), 2.26 (s, 3H); MS (ES) m/z: 435 (M+Na$^+$).

Example XXI

Scheme 23

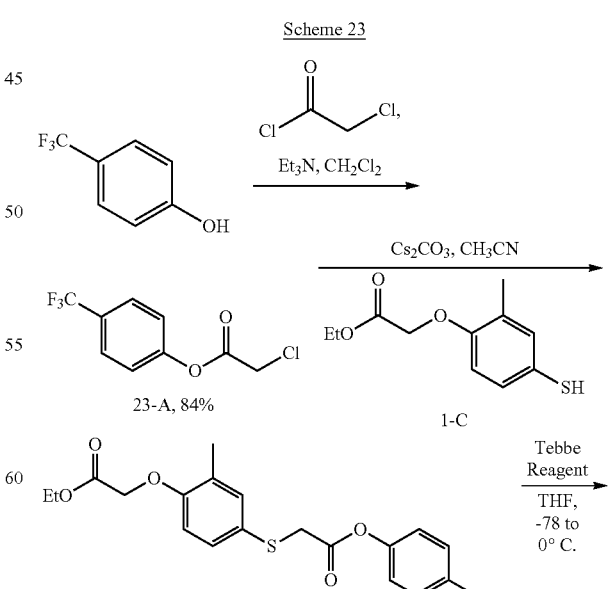

-continued

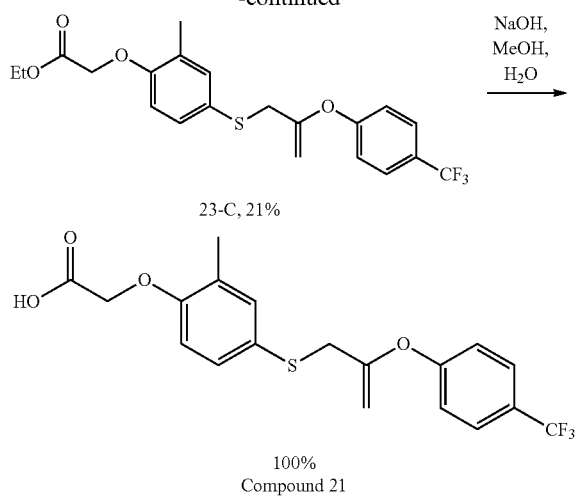

23-C, 21%

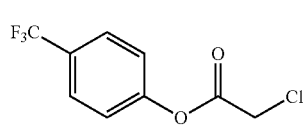

100%
Compound 21

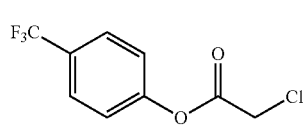

Chloro-acetic acid 4-trifluoromethyl-phenyl ester

To a solution of trifluoromethylphenol (300 mg, 1.85 mmol) in CH$_2$Cl$_2$ (5 mL) at 0° C. were added chloroacetyl chloride (255 mg, 2.26 mmol) and triethylamine (290 mg, 2.87 mmol). After stirring at room temperature overnight, the reaction mixture was diluted with water and extracted with CH$_2$Cl$_2$. The extracts were dried, concentrated, and purified by column chromatography to give 370 mg (84%) of 23-A as a yellow oil; $^1$H NMR (300 MHz, CDCl$_3$) δ 7.68 (d, J=8.5 Hz, 2H), 7.28 (d, J=8.4 Hz, 2H), 4.32 (s, 2H).

23-B

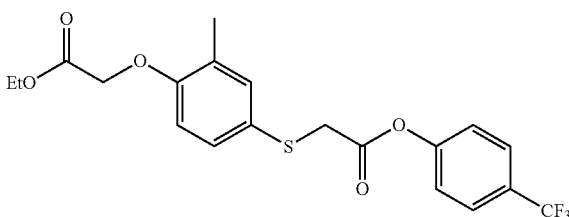

[2-Methyl-4-(4-trifluoromethyl-phenoxycarbonylmethylsulfanyl)-phenoxy]-acetic acid ethyl ester Following general procedure 3 gave 23-B (75%, clear oil); $^1$H NMR (300 MHz, CDCl$_3$) δ 7.63 (d, J=8.6 Hz, 2H), 7.37 (s, 1H), 7.34 (d, J=8.4 Hz, 1H), 7.11 (d, J=8.5 Hz, 2H), 6.65 (d, J=8.4 Hz, 1H), 4.64 (s, 2H), 4.26 (q, J=7.1 Hz, 2H), 3.73 (s, 2H), 2.27 (s, 3H), 1.29 (t, J=7.1 Hz, 3H); MS (ES) m/z: 451 (M+Na$^+$).

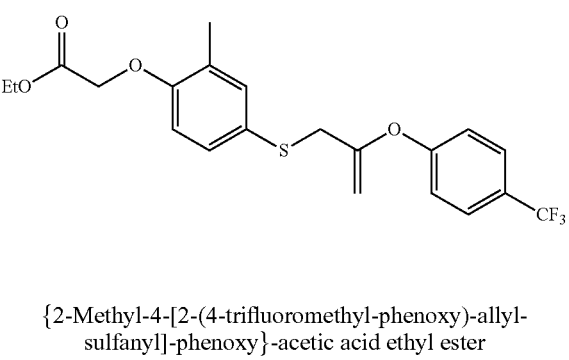

{2-Methyl-4-[2-(4-trifluoromethyl-phenoxy)-allyl-sulfanyl]-phenoxy}-acetic acid ethyl ester To a solution of 23-B (180 mg, 0.421 mmol) in THF (1 mL) at −78° C. was added 0.5 M Tebbe reagent (1.0 mL, 0.5 mmol) in toluene. The mixture was stirred at −78° C. to 0° C. for 1 h, quenched with 6 drops of 2 M NaOH aqueous solution, and filtered through Celite. The filtrate was dried over Na$_2$SO$_4$, concentrated, and purified by column chromatography to give 37 mg (21%) of 23-C as a clear oil; $^1$H NMR (400 MHz, CDCl$_3$) δ 7.58 (d, J=8.4 Hz, 2H), 7.29 (s, 1H), 7.25 (d, J=2.4 Hz, 1H), 7.09 (d, J=8.5 Hz, 2H), 6.64 (d, J=8.4 Hz, 1H), 4.64 (s, 2H), 4.40 (d, J=2.0 Hz, 1H), 4.27 (q, J=7.1 Hz, 2H), 4.19 (d, J=2.0 Hz, 1H), 3.59 (s, 2H), 2.27 (s, 3H), 1.30 (t, J=7.1 Hz, 3H); MS (ES) m/z: 449 (M+Na$^+$).

Compound 21

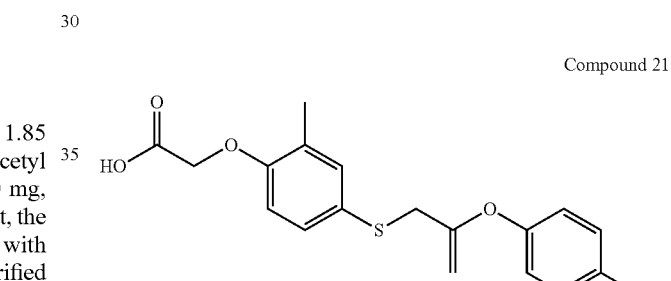

{2-Methyl-4-[2-(4-trifluoromethyl-phenoxy)-allyl-sulfanyl]-phenoxy}-acetic acid

Following general procedure 2 gave Compound 21 (100%, clear oil); $^1$H NMR (300 MHz, CDCl$_3$) δ 7.58 (d, J=8.5 Hz, 2H), 7.27 (m, 2H), 7.09 (d, J=8.3 Hz, 2H), 6.67 (d, J=8.1 Hz, 1H), 4.69 (s, 2H), 4.40 (d, J=2.4 Hz, 1H), 4.19 (d, J=23 Hz, 1H), 3.59 (s, 2H), 2.26 (s, 3H); MS (ES) m/z: 421 (M+Na$^+$); FAB-HRMS (M$^+$). Calcd 398.0800, found 398.0800.

Example XXII

Scheme 26

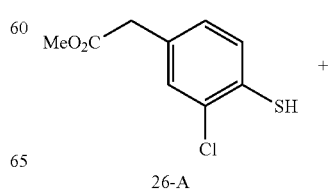

26-A

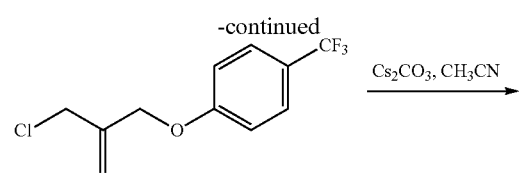

13-A

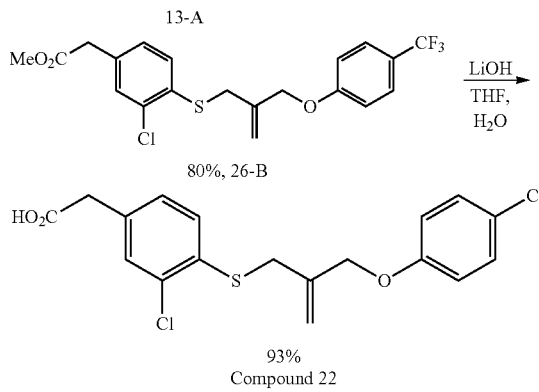

26-B

{3-Chloro-4-[2-(4-trifluoromethyl-phenoxymethyl)-allylsulfanyl]-phenyl}-acetic acid methyl ester Replacing (4-mercapto-2-methyl-phenoxy)-acetic acid ethyl ester 1-C with (3-chloro-4-mercaptophenyl) acetic acid methyl ester 26-A (see WO 9932465) and following general procedure 3 gave the title compound 26-B (80%); $^1$H NMR (300 MHz, CDCl$_3$) δ 7.53 (d, J=8.5 Hz, 2H), 7.31 (d, J=1.8 Hz, 1H), 7.29 (d, J=8.1 Hz, 1H), 7.09 (dd, J=8.1, 1.9 Hz, 1H), 6.96 (d, J=8.5 Hz, 2H), 5.23 (s, 1H), 5.18 (d, J=0.7 Hz, 1H), 4.67 (s, 2H), 3.70 (s, 5H), 3.56 (s, 2H); MS (ES) m/z: 453 (M+Na$^+$). Anal. Calcd for C$_{20}$H$_{18}$ClF$_3$O$_3$S: C, 55.75; H, 4.21. Found: C, 55.58; H, 3.86.

Compound 22

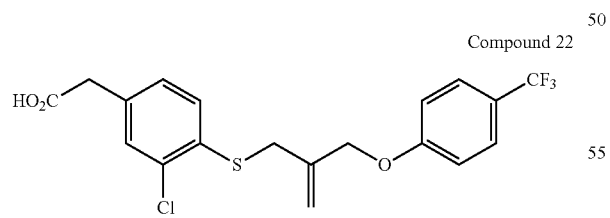

{3-Chloro-4-[2-(4-trifluoromethyl-phenoxymethyl)-allylsulfanyl]-phenyl}-acetic acid Following general procedure 2 gave Compound 22 (93%); $^1$H NMR (300 MHz, CDCl$_3$) δ 7.52 (d, J=8.7 Hz, 2H), 7.31 (d, J=1.7 Hz, 1H), 7.28 (d, J=8.1 Hz, 1H), 7.08 (dd, J=8.1, 1.7 Hz, 1H), 6.96 (d, J=8.7 Hz, 2H), 5.24 (s, 1H), 5.19 (s, 1H), 4.66 (s, 2H), 3.71 (s, 2H), 3.57 (s, 2H); MS (ES) m/z: 439 (M+Na$^+$). Anal. Calcd for C$_{19}$H$_{16}$ClF$_3$O$_3$S: C, 54.75; H, 3.87. Found: C, 54.45; H, 3.54.

Example XXIII

Scheme 28

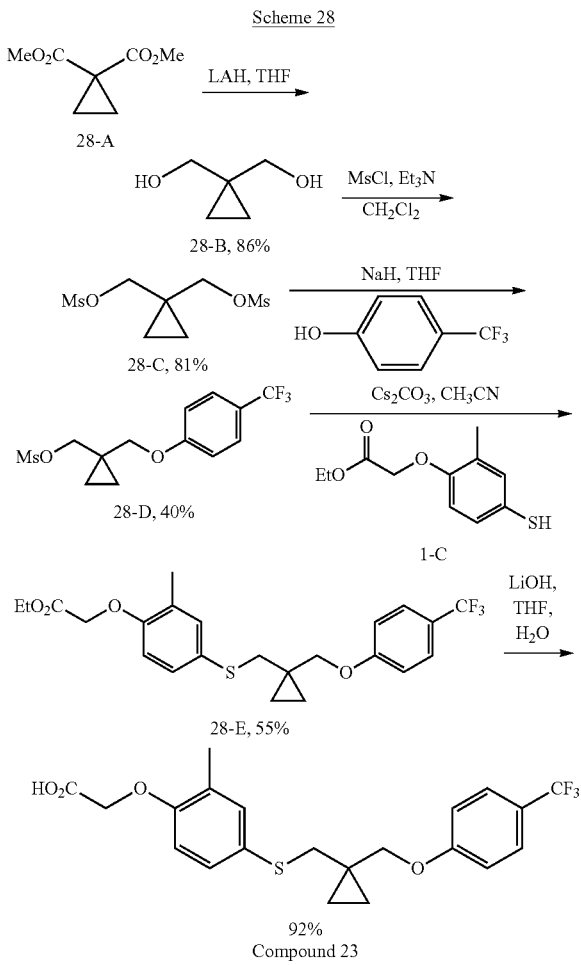

28-B (1-Hydroxymethyl-cyclopropyl)-methanol

To a solution of dimethyl 1,1-cyclopropanedicarboxylate 28-A (791 mg, 5.01 mmol) in Et$_2$O (20 mL) at 0° C. was added lithium aluminum hydride (569 mg, 15.0 mmol) portionwise. The reaction mixture was stirred at room temperature for 4 h and quenched with saturated Na$_2$SO$_4$ at 0° C. The precipitated solid was filtered and washed with THF. The filtrate was concentrated and purified by column chromatography (EtOAc) to give 440 mg (86%) of 28-B; $^1$H NMR (300 MHz, CDCl$_3$) δ 4.02 (s, 2H), 3.56 (s, 4H), 0.48 (s, 4H); MS (ES) m/z: 125 (M+Na$^+$).

Methanesulfonic Acid 1-methanesulfonyloxymethyl-cyclopropylmethyl ester

To a solution of 28-B (440 mg, 4.31 mmol) in CH$_2$Cl$_2$ (6 mL) at 0° C. were added Et$_3$N (2.59 mL, 17.2 mmol) and a solution of methanesulfonyl chloride (1.48 g, 12.9 mmol) in CH$_2$Cl$_2$ (4 mL). The mixture was stirred at room temperature for 2 h and diluted with 1.0 N HCl. The organic layer was separated and the aqueous layer was extracted with CH$_2$Cl$_2$ (×3). The combined organic phases were dried, concentrated, and column chromatographed (EtOAc/hexane: 1/1) to provide 901 mg (81%) of 28-C; $^1$H NMR (300 MHz, CDCl$_3$) δ 4.17 (s, 4H), 3.06 (s, 6H), 0.83 (s, 4H); MS (ES) m/z: 281 (M+Na$^+$).

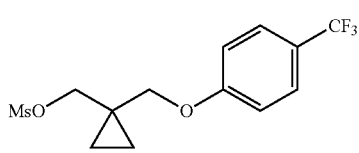

Methanesulfonic Acid 1-(4-trifluoromethyl-phenoxymethyl)-cyclopropylmethyl ester To a suspension of NaH (44 mg, 1.1 mmol; 60% in mineral oil) in THF (1 mL) was added a solution of 4-trifluoromethylphenol (178 mg, 1.10 mmol) in THF (1 mL). After stirring for 30 min at room temperature, the mixture was transferred to a flask containing a solution of 28-C (310 mg, 1.20 mmol) in DMF (2 mL). The resulting mixture was refluxed for 6 h and allowed to cool to room temperature, diluted with water, and extracted with Et$_2$O. The extracts were dried, concentrated, and column chromatographed (EtOAc/hexane: 1/4) to give 141 mg (40%) of 28-D; $^1$H NMR (300 MHz, CDCl$_3$) δ 7.54 (d, J=8.7 Hz, 2H), 6.96 (d, J=8.6 Hz, 2H), 4.26 (s, 2H), 3.92 (s, 2H), 2.97 (s, 3H), 0.802 (s, 2H), 0.798 (s, 2H); MS (ES) m/z: 347 (M+Na$^+$).

{2-Methyl-4-[1-(4-trifluoromethyl-phenoxymethyl)-cyclopropylmethylsulfanyl]-phenoxy}-acetic acid ethyl ester Following general procedure 3 gave 28-E (55%); $^1$H NMR (300 MHz, CDCl$_3$) δ 7.50 (d, J=8.6 Hz, 2H), 7.20 (d, J=1.8 Hz, 1H), 7.15 (dd, J=8.4, 2.2 Hz, 1H), 6.88 (d, J=8.6 Hz, 2H), 6.50 (d, J=8.4 Hz, 1H), 4.53 (s, 2H), 4.24 (q, J=7.1 Hz, 2H), 3.91 (s, 2H), 3.05 (s, 2H), 2.17 (s, 3H), 1.28 (t, J=7.1 Hz, 3H), 0.65-0.55 (m, 4H); MS (ES) m/z: 477 (M+Na$^+$). Anal. Calcd for C$_{23}$H$_{25}$F$_3$O$_4$S: C, 60.78; H, 5.54. Found: C, 60.98; H, 5.43.

Compound 23

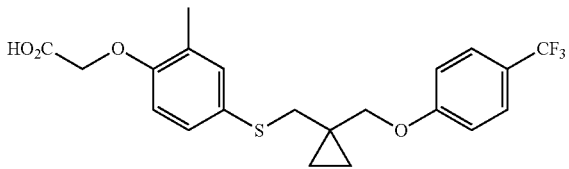

{2-Methyl-4-[1-(4-trifluoromethyl-phenoxymethyl)-cyclopropylmethylsulfanyl]-phenoxy}-acetic acid Following general procedure 2 gave Compound 23 (92%); $^1$H NMR (300 MHz, CDCl$_3$) δ 9.67 (brs, 1H), 7.49 (d, J=8.7 Hz, 2H), 7.20 (s, 1H), 7.16 (dd, J=8.4, 2.1 Hz, 1H), 6.87 (d, J=8.6 Hz, 2H), 6.52 (d, J=8.4 Hz, 1H), 4.58 (s, 2H), 3.91 (s, 2H), 3.06 (s, 2H), 2.16 (s, 3H), 0.66-0.56 (m, 4H); MS (ES) m/z: 449 (M+Na$^+$).

Example XXIV

Scheme 29

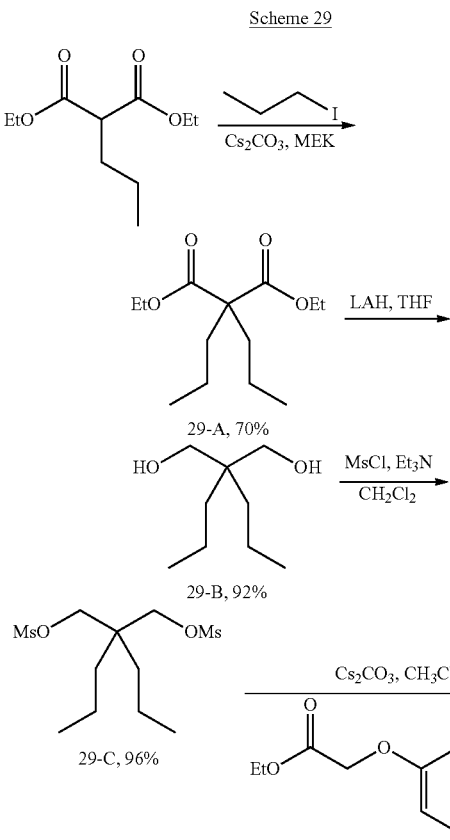

-continued

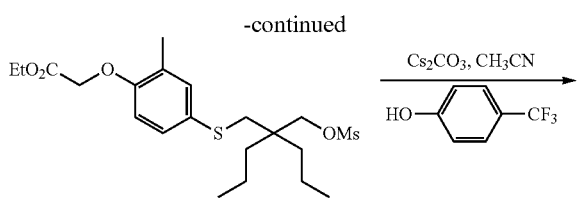

29-D, 35%

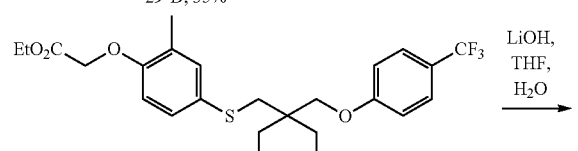

29-E, 3%

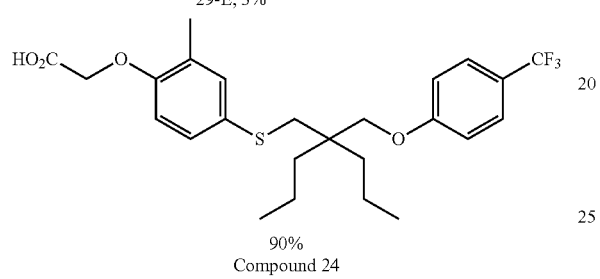

90%
Compound 24

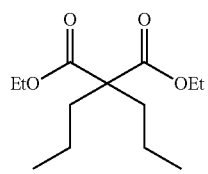

29-A 2,2-Dipropyl-malonic acid diethyl ester

A mixture of diethyl propylmalonate (2.02 mg, 1.00 mmol), 1-iodopropane (255 mg, 1.50 mmol), and $Cs_2CO_3$ (424 mg, 1.30 mmol) in 2-butanone (5 mL) was heated at 70° C. for 15 h and filtered. The filtrate was concentrated and column chromatographed (EtOAc/hexane:1/19) to give 170 mg (70%) of 29-A; $^1$H NMR (300 MHz, $CDCl_3$) δ 4.17 (q, J=7.1 Hz, 4H), 1.88-1.82 (m, 4H), 1.25-1.12 (m, 4H), 1.24 (t, J=7.1 Hz, 6H), 0.92 (t, J=7.2 Hz, 6H); MS (ES) m/z: 267 (M+Na$^+$).

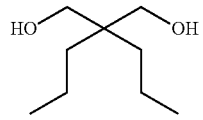

29-B 2,2-Dipropyl-propane-1,3-diol

To a suspension of lithium aluminum hydride (52 mg, 1.4 mmol) in THF (1 mL) at 0° C. was added a solution of 29-A (167 mg, 0.684 mmol) in THF. The reaction mixture was stirred at room temperature for 2 h, quenched with water (0.1 mL) at 0° C., and diluted with 5.0 M NaOH (0.1 mL) and water (1 mL). The precipitated solid was filtered and washed with MeOH/$CH_2Cl_2$. The filtrate was concentrated and purified by column chromatography (EtOAc/hexane: 1/1) to give 101 mg (92%) of 29-B; $^1$H NMR (300 MHz, $CDCl_3$) δ 3.57 (s, 4H), 2.47 (s, 2H), 1.26-1.23 (m, 8H), 0.95-0.90 (m, 6H); MS (ES) m/z: 183 (M+Na$^+$).

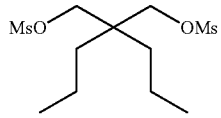

29-C

Methanesulfonic Acid
2-methanesulfonyloxymethyl-2-propyl-pentyl ester

To a solution of 29-B (96 mg, 0.60 mmol) in $CH_2Cl_2$ (1.5 mL) at 0° C. were added $Et_3N$ (0.334 mL, 2.40 mmol) and methanesulfonyl chloride (207 mg, 1.81 mmol). The mixture was stirred at room temperature for 1 h and diluted with saturated $NaHCO_3$. The organic layer was separated and the aqueous layer was extracted with $CH_2Cl_2$ (×3). The combined organic phases were dried, concentrated, and column chromatographed (EtOAc/hexane: 1/1) to provide 182 mg (96%) of 29-C; $^1$H NMR (300 MHz, $CDCl_3$) δ 4.04 (s, 4H), 3.04 (s, 6H), 1.31-1.28 (m, 8H), 0.96-0.91 (m, 6H); MS (ES) m/z: 339 (M+Na$^+$).

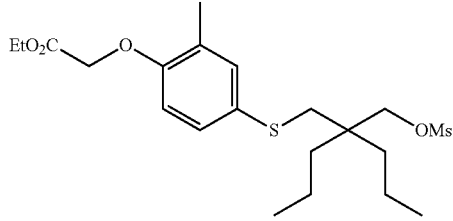

29-D

[4-(2-Methanesulfonyloxymethyl-2-propyl-pentyl-sulfanyl)-2-methyl-phenoxy]-acetic acid ethyl ester Following general procedure 3 gave 29-D (35%); $^1$H NMR (300 MHz, $CDCl_3$) δ 7.23 (d, J=1.6 Hz, 1H), 7.19 (dd, J=8.5, 2.1 Hz, 1H), 6.62 (d, J=8.4 Hz, 1H), 4.61 (s, 2H), 4.25 (q, J=7.1 Hz, 2H), 4.06 (s, 2H), 2.89 (s, 2H), 2.88 (s, 3H), 2.26 (s, 3H), 1.36-1.24 (m, 8H), 1.29 (t, J=7.1 Hz, 3H), 1.20 (t, J=7.0 Hz, 6H); MS (ES) m/z: 469 (M+Na$^+$).

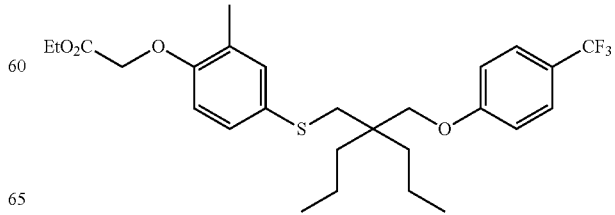

29-E

{2-Methyl-4-[2-propyl-2-(4-trifluoromethyl-phenoxymethyl)-pentylsulfanyl]-phenoxy}-acetic acid ethyl ester A mixture of 29-D (78 mg, 0.17 mmol), Cs$_2$CO$_3$ (111 mg, 0.341 mmol), and trifluoromethylphenol (85 mg, 0.52 mmol) in CH$_3$CN (2 mL) was refluxed overnight. More Cs$_2$CO$_3$ (111 mg, 0.341 mmol) and trifluoromethylphenol (85 mg, 0.52 mmol) were added, and the mixture was refluxed for 24 h. TLC showed very small amount of the desired product and a large amount of starting materials. More Cs$_2$CO$_3$ (111 mg, 0.341 mmol) and trifluoromethylphenol (85 mg, 0.52 mmol) were added, and the mixture was refluxed for another 24 h. Water was added, and the mixture was extracted with Et$_2$O (×3). The extracts were dried, concentrated, and column chromatographed (EtOAc/hexane: 1/9) to provide 3 mg (3%) of 29-E; $^1$H NMR (400 MHz, CDCl$_3$) δ 7.47 (d, J=8.7 Hz, 2H), 7.15 (s, 1H), 7.11 (dd, J=8.4, 1.8 Hz, 1H), 6.81 (d, J=8.6 Hz, 2H), 6.43 (d, J=8.4 Hz, 1H), 4.49 (s, 2H), 4.24 (q, J=7.1 Hz, 2H), 3.76 (s, 2H), 3.00 (s, 2H), 2.14 (s, 2H), 1.43-1.39 (m, 4H), 1.30-1.20 (m, 7H), 0.89 (t, J=7.1 Hz, 6H); MS (ES) m/z: 535 (M+Na$^+$).

Compound 24

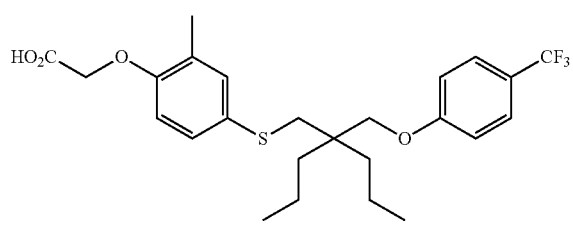

{2-Methyl-4-[2-propyl-2-(4-trifluoromethyl-phenoxymethyl)-pentylsulfanyl]-phenoxy}-acetic acid Following general procedure 2 gave Compound 24 (90%); $^1$H NMR (300 MHz, CDCl$_3$) δ 7.45 (d, J=8.5 Hz, 2H), 7.09 (s, 1H), 7.06 (m, 1H), 6.80 (d, J=8.5 Hz, 2H), 6.44 (m, 1H), 4.34 (s, 2H), 3.75 (s, 2H), 2.97 (s, 2H), 2.05 (s, 3H), 1.41-1.38 (m, 3H), 1.33-1.19 (m, 5H), 0.88 (t, J=6.9 Hz, 6H); MS (ES) m/z: 507 (M+Na$^+$).

Example XXV

Scheme 30

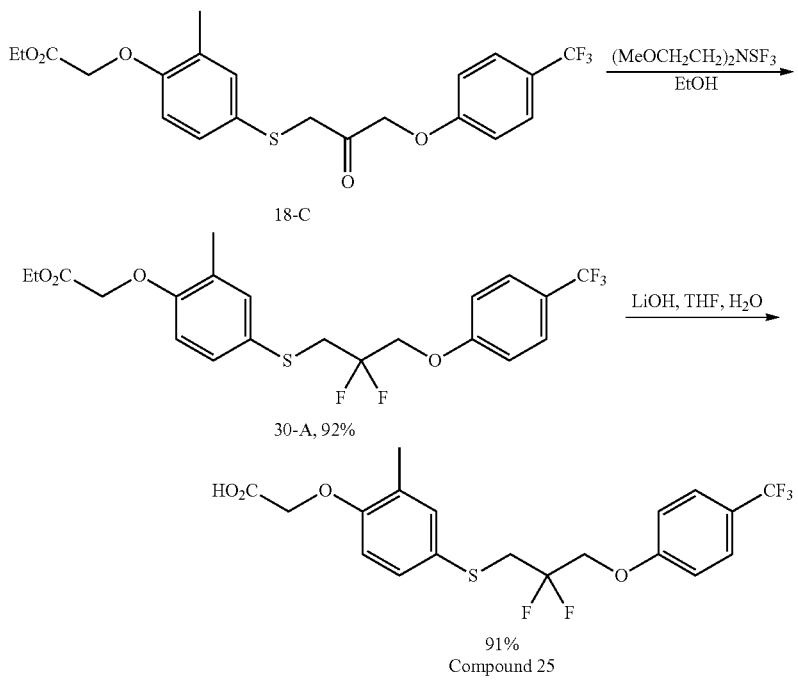

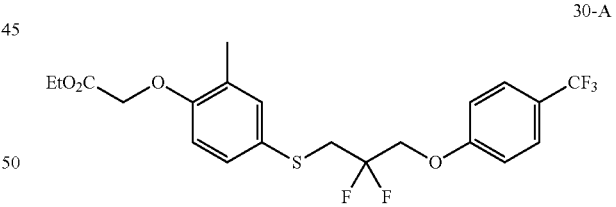

{4-[2,2-Difluoro-3-(4-trifluoromethyl-phenoxy)-propylsulfanyl]-2-methyl-phenoxy}-acetic acid ethyl ester A reaction mixture of 18-C (50 mg, 0.11 mmol), [bis(2-methoxyethyl)amino]sulfur trifluoride (49 mg, 0.22 mmol), and ethanol (0.0012 mL, 0.022 mmol) in CH$_2$Cl$_2$ (2 mL) was stirred at room temperature for 14 h, then diluted with saturated NaHCO$_3$ until CO$_2$ evolution ceased. The mixture was extracted with CH$_2$Cl$_2$, and the extracts were dried, concentrated, and column chromatographed (EtOAc/hexane: 1/7) to provide 47 mg (92%) of 30-A; $^1$H NMR (300 MHz, CDCl$_3$)

δ 7.52 (d, J=8.7 Hz, 2H), 7.24 (s, 1H), 7.21 (dd, J=8.4, 2.0 Hz, 1H), 6.82 (d, J=8.7 Hz, 2H), 6.47 (d, J=8.4 Hz, 1H), 4.50 (s, 2H), 4.29-4.22 (m, 4H), 3.42 (t, J=14.1 Hz, 2H), 2.16 (s, 3H), 1.28 (t, J=7.1 Hz, 3H); MS (ES) m/z: 487 (M+Na⁺). Anal. Calcd for $C_{21}H_{21}F_5O_4S$: C, 54.31; H, 4.56. Found: C, 54.52; H, 4.55.

Compound 25

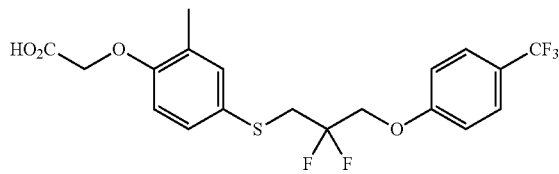

{4-[2,2-Difluoro-3-(4-trifluoromethyl-phenoxy)-propylsulfanyl]-2-methyl-phenoxy}-acetic acid Following general procedure 2 gave Compound 25 (91%); ¹H NMR (300 MHz, CDCl₃) δ 10.47 (brs, 1H), 7.51 (d, J=8.6 Hz, 2H), 7.21 (m, 2H), 6.81 (d, J=8.6 Hz, 2H), 6.49 (d, J=8.3 Hz, 1H), 4.56 (s, 2H), 4.25 (t, J=11.1 Hz, 2H), 3.42 (t, J=14.1 Hz, 2H), 2.15 (s, 3H); MS (ES) m/z: 459 (M+Na⁺).

Example XXVI

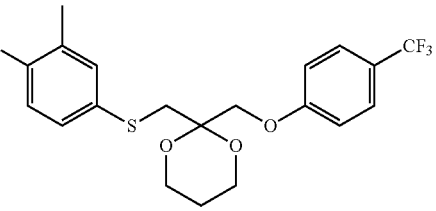

{2-Methyl-4-[2-(4-trifluoromethyl-phenoxymethyl)-[1,3]dioxan-2-ylmethylsulfanyl]-phenoxy}-acetic acid ethyl ester A mixture of 18-C (270 mg, 0.611 mmol) and trimethylsilyl chloride (265 mg, 2.44 mmol) in 1,3-propanediol (1 mL) was stirred at room temperature overnight, diluted with 5% NaHCO₃, and extracted with Et₂O. The extracts were washed with 5% NaHCO₃ and brine, dried, and concentrated to give the crude 31-A; ¹H NMR (300 MHz, CDCl₃) δ 7.48 (d, J=8.8 Hz, 2H), 7.19 (m, 2H), 6.86 (d, J=8.8 Hz, 2H), 6.43 (d, J=8.4 Hz, 1H), 4.48 (s, 2H), 4.24 (q, J=7.1 Hz, 2H), 4.16 (s, 2H), 3.94 (m, 4H), 3.48 (s, 2H), 2.14 (s, 3H), 1.90 (m, 1H), 1.66 (m, 1H), 1.28 (t, J=7.1 Hz, 3H); MS (ES) m/z: 523 (M+Na⁺).

Scheme 31

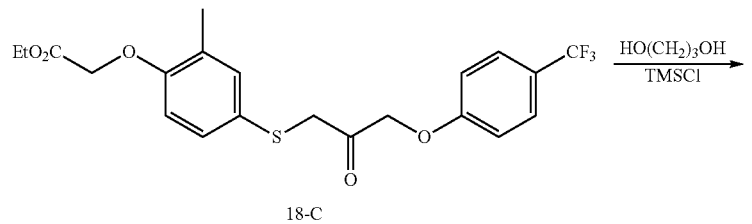

18-C

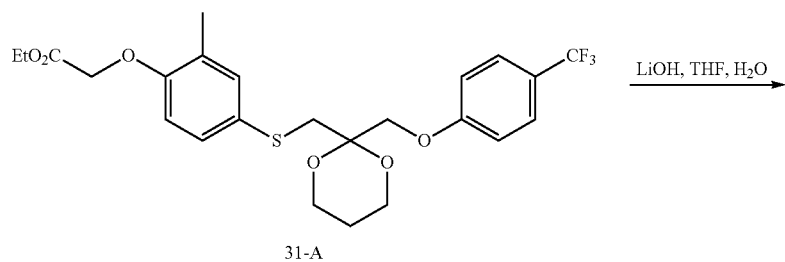

31-A

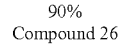

90%
Compound 26

Compound 26
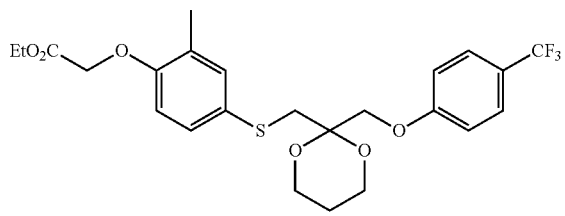
{2-Methyl-4-[2-(4-trifluoromethyl-phenoxymethyl)-[1,3]dioxan-2-ylmethylsulfanyl]-phenoxy}-acetic acid
Following general procedure 2 gave Compound 26 (90%); $^1$H NMR (300 MHz, CDCl$_3$) δ 7.46 (d, J=8.7 Hz, 2H), 7.15 (m, 2H), 6.86 (d, J=8.7 Hz, 2H), 6.43 (d, J=8.2 Hz, 1H), 4.36 (s, 2H), 4.15 (s, 2H), 3.91 (m, 4H), 3.45 (s, 2H), 2.06 (s, 3H), 1.86 (m, 1H), 1.64 (m, 1H); MS (ES) m/z: 495 (M+Na$^+$).
Example XXVII
Scheme 32
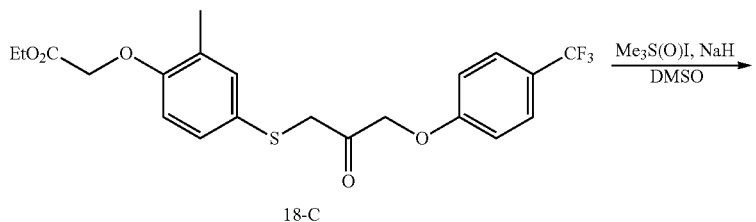
18-C
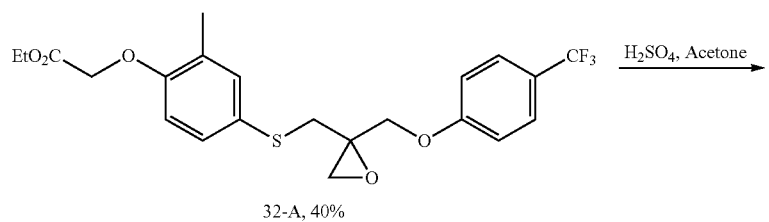
32-A, 40%
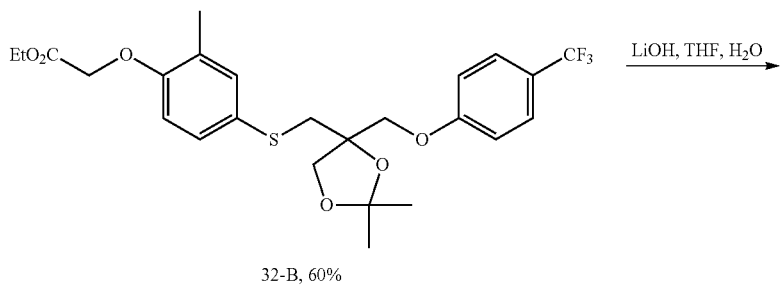
32-B, 60%
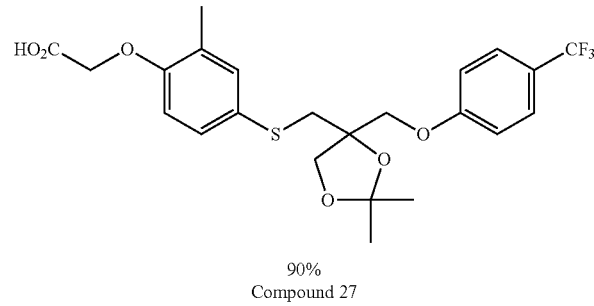
90%
Compound 27

32-A

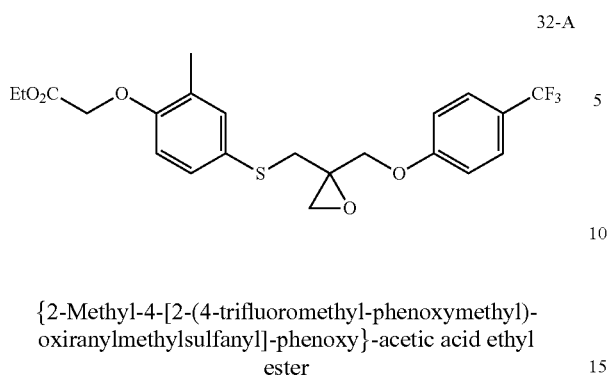

{2-Methyl-4-[2-(4-trifluoromethyl-phenoxymethyl)-oxiranylmethylsulfanyl]-phenoxy}-acetic acid ethyl ester A mixture of trimethylsulfoxonium iodide (69 mg, 0.31 mmol) and NaH (10 mg, 0.25 mmol; 60% in mineral oil) in DMSO (0.5 mL) was stirred at room temperature for 1 h, and then a solution of 18-C (100 mg, 0.226 mmol) in DMSO (0.5 mL) was added. The reaction mixture was heated at −60° C. for 2 h, quenched with water, and extracted with Et$_2$O. The extracts were dried, concentrated, and purified by column chromatography (EtOAc/hexane: 1/4) to afford 41 mg (40%) of 32-A; $^1$H NMR (300 MHz, CDCl$_3$) δ 7.52 (d, J=8.5 Hz, 2H), 7.25 (d, J=1.8 Hz, 1H), 7.21 (dd, J=8.4, 2.1 Hz, 1H), 6.91 (d, J=8.5 Hz, 2H), 6.54 (d, J=8.4 Hz, 1H), 4.56 (s, 2H), 4.37 (d, J=10.6 Hz, 1H), 4.25 (q, J=7.1 Hz, 2H), 4.00 (d, J=10.6 Hz, 1H), 3.42 (d, J=14.3 Hz, 1H), 2.95 (d, J=14.2 Hz, 1H), 2.81 (dd, J=5.4, 0.9 Hz, 1H), 2.67 (d, J=5.4 Hz, 1H), 2.20 (s, 3H), 1.29 (t, J=7.1 Hz, 3H); MS (ES) m/z: 479 (M+Na$^+$).

32-B

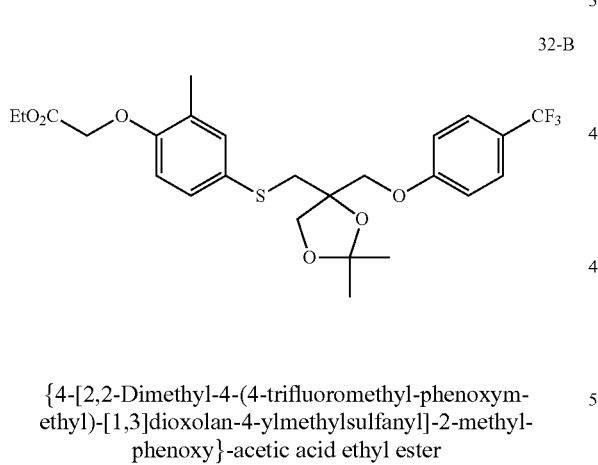

{4-[2,2-Dimethyl-4-(4-trifluoromethyl-phenoxymethyl)-[1,3]dioxolan-4-ylmethylsulfanyl]-2-methyl-phenoxy}-acetic acid ethyl ester A solution of 32-A (80 mg, 0.17 mmol) in acetone (5 mL) was treated with 5 N H$_2$SO$_4$ (0.1 mL) at room temperature for 24 h, and concentrated. The residue was partitioned between EtOAc and water. The organic layer was dried, concentrated, and column chromatographed (EtOAc/hexane: 1:7) to give 55 mg (60%) of 32-B; $^1$H NMR (300 MHz, CDCl$_3$) δ 7.48 (d, J=8.5 Hz, 2H), 7.19 (d, J=1.7 Hz, 1H), 7.15 (dd, J=8.4, 2.2 Hz, 1H), 6.80 (d, J=8.6 Hz, 2H), 6.43 (d, J=8.4 Hz, 1H), 4.48 (s, 2H), 4.24 (q, J=7.1 Hz, 2H), 4.08-3.95 (m, 4H), 3.35 (d, J=13.8 Hz, 1H), 3.19 (d, J=13.8 Hz, 1H), 2.14 (s, 3H), 1.44 (s, 3H), 1.43 (s, 3H), 1.28 (t, J=7.1 Hz, 3H); MS (ES) m/z: 537 (M+Na$^+$).

Compound 27

{4-[2,2-Dimethyl-4-(4-trifluoromethyl-phenoxymethyl)-[1,3]dioxolan-4-ylmethylsulfanyl]-2-methyl-phenoxy}-acetic acid Following general procedure 2 gave Compound 27 (90%); $^1$H NMR (300 MHz, CDCl$_3$) δ 9.42 (brs, 1H), 7.46 (d, J=8.6 Hz, 2H), 7.19 (s, 1H), 7.15 (d, J=8.4 Hz, 1H), 6.79 (d, J=8.6 Hz, 2H), 6.44 (d, J=8.4 Hz, 1H), 4.52 (s, 2H), 4.14-3.93 (m, 4H), 3.36 (d, J=13.8 Hz, 1H), 3.20 (d, J=13.8 Hz, 1H), 2.12 (s, 3H), 1.45 (s, 3H), 1.43 (s, 3H); MS (ES) m/z: 509 (M+Na$^+$).

Example XXVIII

Scheme 33

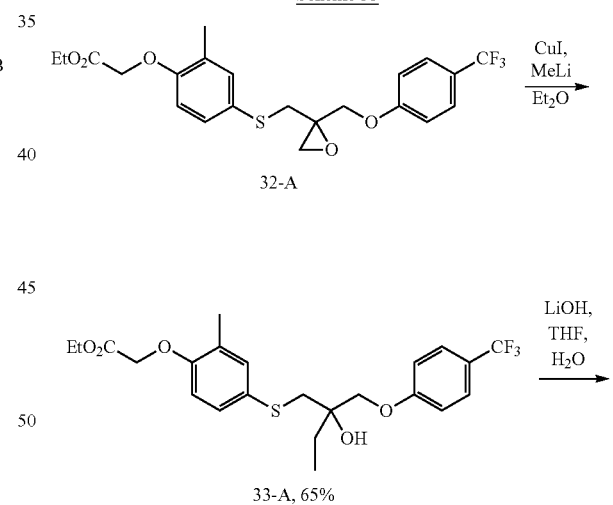

33-A

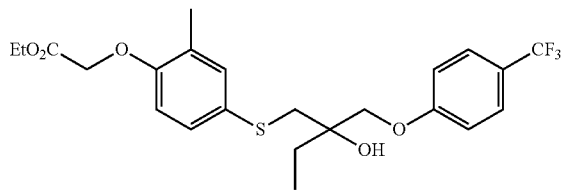

{4-[2-Hydroxy-2-(4-trifluoromethyl-phenoxymethyl)-butylsulfanyl]-2-methyl-phenoxy}-acetic acid ethyl ester To a suspension of CuI (61 mg, 0.32 mmol) in Et$_2$O (0.8 mL) at 0° C. was added 1.4 M MeLi (0.457 mL, 0.640 mmol) in THF. After the mixture was stirred for 1 h, a solution of 32-A (145 mg, 0.32 mmol) in Et$_2$O (1 mL) was added. The mixture was allowed to warm up to room temperature in 2 h and partitioned between Et$_2$O and water. The combined organic layers were dried, concentrated, and column chromatographed (EtOAc/hexane: 1/7) to provide 98 mg (65%) of 33-A; $^1$H NMR (300 MHz, CDCl$_3$) δ 7.48 (d, J=8.6 Hz, 2H), 7.20 (s, 1H), 7.16 (dd, J=8.4, 2.2 Hz, 1H), 6.79 (d, J=8.6 Hz, 2H), 6.44 (d, J=8.4 Hz, 1H), 4.47 (s, 2H), 4.24 (q, J=7.1 Hz, 2H), 3.86 (d, J=9.0 Hz, 1H), 3.79 (d, J=9.0 Hz, 1H), 3.27 (d, J=13.8 Hz, 1H), 3.10 (d, J=13.8 Hz, 1H), 2.59 (s, 1H), 2.13 (s, 3H), 1.74 (q, J=7.6 Hz, 2H), 1.28 (t, J=7.1 Hz, 3H), 0.96 (t, J=7.5 Hz, 3H); MS (ES) m/z: 495 (M+Na$^+$).

Compound 28

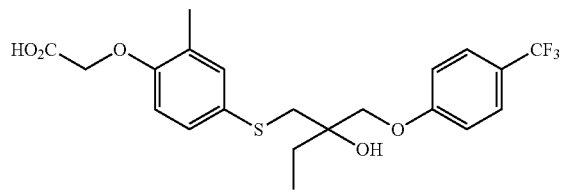

{4-[2-Hydroxy-2-(4-trifluoromethyl-phenoxymethyl)-butylsulfanyl]-2-methyl-phenoxy}-acetic acid Following general procedure 2 gave Compound 28 (91%); $^1$H NMR (300 MHz, CDCl$_3$) δ 7.46 (d, J=8.6 Hz, 2H), 7.20 (s, 1H), 7.17 (d, J=8.4, 1 H), 6.77 (d, J=8.6 Hz, 2H), 6.45 (d, J=8.4 Hz, 1H), 4.52 (s, 2H), 3.86 (d, J=9.0 Hz, 1H), 3.78 (d, J=9.0 Hz, 1H), 3.27 (d, J=13.8 Hz, 1H), 3.12 (d, J=13.8 Hz, 1H), 2.12 (s, 3H), 1.75 (q, J=7.6 Hz, 2H), 0.96 (t, J=7.5 Hz, 3H); MS (ES) m/z: 467 (M+Na$^+$).

Example XXIX

35-A

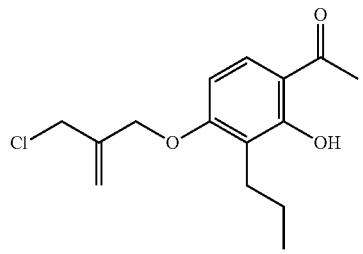

1-[4-(2-Chloromethyl-allyloxy)-2-hydroxy-3-propylphenyl]-ethanone

A mixture of 1-(2,4-dihydroxy-3-propyl-phenyl)-ethanone (158 mg, 0.814 mmol), methanesulfonic acid 2-chloromethyl-allyl ester 5-A (750 mg, 4.06 mmol), and Cs$_2$CO$_3$ (662 mg, 2.03 mmol) in 2-butanone (3 mL) was stirred at room temperature for 6 h, acidified with 1 N HCl, and extracted with Et$_2$O. The extracts were dried, concentrated, and column chromatographed (EtOAc/hexane:1/7) to provide 190 mg (83%) of the title compound 35-A; $^1$H NMR (300 MHz, CDCl$_3$) δ 7.59 (d, J=9.0 Hz, 1H), 6.46 (d, J=9.0 Hz, 1H), 5.41 (s, 1H), 5.37 (s, 1H), 4.70 (s, 2H), 4.20 (s, 2H), 2.66 (t, J=7.6 Hz, 2H), 2.56 (s, 3H), 1.55 (m, 2H), 0.95 (t, J=7.4 Hz, 3H); MS (ES) m/z: 305 (M+Na$^+$).

Example XXX

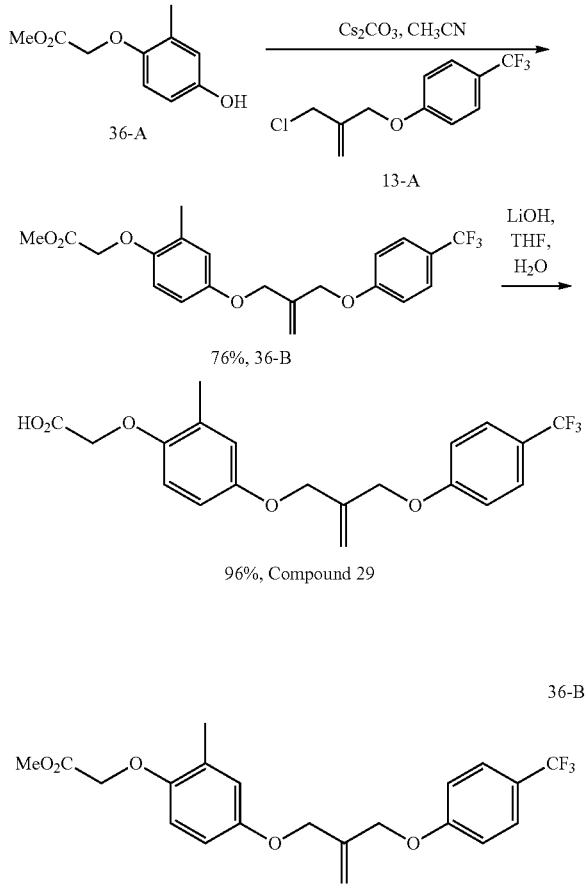

Replacing (4-mercapto-2-methyl-phenoxy)-acetic acid ethyl ester 1-C with (4-hydroxy-2-methyl-phenoxy)-acetic acid methyl ester 36-A, which can be readily made according to, for example, Sznaidman et al., Bioorganic & Medicinal Chemistry Letters 13 (2003) 1517-1521, and following general procedure 3 gave the title compound 36-B (76%); $^1$H NMR (400 MHz, CDCl$_3$) δ 7.53 (d, J=8.8 Hz, 2H), 6.99 (d, J=8.7 Hz, 2H), 6.76 (d, J=1.8 Hz, 1H), 6.66 (m, 2H), 5.41 (s, 1H), 5.39 (s, 1H), 4.67 (s, 2H), 4.59 (s, 2H), 4.57 (s, 2H), 3.79 (s, 3H), 2.26 (s, 3H); MS (ES) m/z: 433 (M+Na$^+$).

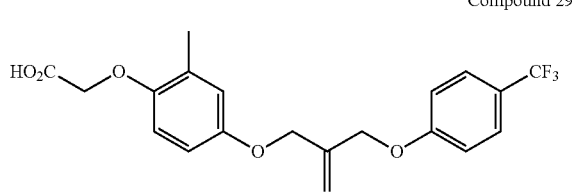

Compound 29

Following general procedure 2 gave Compound 29 (96%); $^1$H NMR (400 MHz, CDCl$_3$) δ 7.54 (d, J=8.7 Hz, 2H), 6.99 (d, J=8.7 Hz, 2H), 6.78 (s, 1H), 6.69 (m, 2H), 5.42 (s, 1H), 5.40 (s, 1H), 4.67 (s, 2H), 4.63 (s, 2H), 4.58 (s, 2H), 2.26 (s, 3H); MS (ES) m/z: 419 (M+Na$^+$).

D. FORMULATION AND ADMINISTRATION

The present compounds are PPAR delta agonists and are therefore useful in treating or inhibiting the progression of PPAR delta mediated conditions, such as diabetes, cardiovascular diseases, Metabolic X Syndrome, hypercholesterolemia, hypo-HDL-cholesterolemia, hyper-LDL-cholesterolemia, dyslipidemia, atherosclerosis, obesity, and complications thereof. For instance, complications of diabetes include such conditions as neuropathy, nephropathy, and retinopathy.

The invention features a method for treating a subject with a PPAR delta mediated disease, said method comprising administering to the subject a therapeutically effective amount of a pharmaceutical composition comprising a compound of the invention. The invention also provides a method for treating or inhibiting the progression of diabetes or impaired glucose tolerance in a subject, wherein the method comprises administering to the subject a therapeutically effective amount of a pharmaceutical composition comprising a compound of the invention.

The compounds of the present invention may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier.

A carrier may take a wide variety of forms depending on the form of preparation desired for administration. These pharmaceutical compositions are desirably in unitary dosage form suitable, preferably, for oral administration or parenteral injection. For example, in preparing the compositions in oral dosage form, any of the usual pharmaceutical media may be employed. These include water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. In view of their ease in administration, tablets and capsules represent the most advantageous oral dosage unit form, in which case solid pharmaceutical carriers are generally employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Such additives may facilitate the administration to the skin and/or may be helpful for preparing the desired compositions. These compositions may be administered in various ways, e.g., as a transdermal patch, as a spot-on, as an ointment. Acid addition salts of the compounds of formula I, due to their increased water solubility over the corresponding base form, are more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Pharmaceutically acceptable acid addition salts include the therapeutically active non-toxic acid addition salts of disclosed compounds. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term addition salt also comprises the solvates which the disclosed compounds, as well as the salts thereof, are able to form. Such solvates are for example hydrates, alcoholates and the like. Conversely the salt form can be converted by treatment with alkali into the free base form.

Stereoisomeric forms define all the possible isomeric forms which the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

Those of skill in the treatment of disorders or conditions mediated by the PPAR delta could easily determine the effective daily amount from the test results presented hereinafter and other information. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.05 mg to 250 mg or 750 mg, and in particular 0.5 to 50 mg of active ingredient per unit dosage form. Examples include 2 mg, 4 mg, 7 mg, 10 mg, 15 mg, 25 mg, and 35 mg dosage forms. Compounds of the invention may also be prepared in time-release or subcutaneous or transdermal patch formulations. Disclosed compound may also be formulated as a spray or other topical or inhalable formulations.

The exact dosage and frequency of administration depends on the particular compound of Formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines.

The next section includes detailed information relating to the use of the disclosed compounds and compositions.

E. USE

The compounds of the present invention are pharmaceutically active, for example, as PPAR delta agonists. According to one aspect of the invention, the compounds are preferably selective PPAR delta agonists, having an activity index (e.g., PPAR delta potency over PPAR alpha/gamma potency) of 10 or more, and preferably 15, 25, 30, 50 or 100 or more.

According to the invention, the disclosed compounds and compositions are useful for the amelioration of symptoms associated with, the treatment of, and the prevention of, the following conditions and diseases: phase I hyperlipidemia, pre-clinical hyperlipidemia, phase II hyperlipidemia, hypertension, CAD (coronary artery disease), coronary heart disease, and hypertriglyceridemia. Preferred compounds of the invention are useful in lowering serum levels of low-density lipoproteins (LDL), intermediate density lipoprotein (IDL), and/or small-density LDL and other atherogenic molecules, or molecules that cause atherosclerotic complications, thereby reducing cardiovascular complications. Preferred compounds also are useful in elevating serum levels of high-density lipoproteins (HDL), in lowering serum levels of triglycerides, LDL, and/or free fatty acids. It is also desirable to lower fasting plasma glucose (FPG)/HbA1c.

The invention also features pharmaceutical compositions which include, without limitation, one or more of the disclosed compounds, and pharmaceutically acceptable carrier or excipient.

1. Dosages

Those skilled in the art will be able to determine, according to known methods, the appropriate dosage for a patient, taking into account factors such as age, weight, general health, the type of symptoms requiring treatment, and the presence of other medications. In general, an effective amount will be between 0.1 and 1000 mg/kg per day, preferably between 1 and 300 mg/kg body weight, and daily dosages will be between 10 and 5000 mg for an adult subject of normal weight. Capsules, tablets or other formulations (such as liquids and film-coated tablets) may be of between 5 and 200 mg, such as 10, 15, 25, 35, 50 mg, 60 mg, and 100 mg and can be administered according to the disclosed methods.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

3. Combination Therapy

The compounds of the present invention may be used in combination with other pharmaceutically active agents. These agents include lipid lowering agents, and blood pressure lowering agents such as statin drugs and the fibrates.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

Anti-diabetic agents include thiazolidinedione and non-thiazolidinedione insulin sensitizers, which decrease peripheral insulin resistance by enhancing the effects of insulin at target organs and tissues.

Some of the following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as:

(1) rosiglitazone (2,4-thiazolidinedione,5-((4-(2-(methyl-2-pyridinylamino)ethoxy)phenyl)methyl)-, (Z)-2-butenedioate (1:1) or 5-((4-(2-(methyl-2-pyridinylamino)ethoxy)phenyl)methyl)-2,4-thiazolidinedione, known as AVANDIA; also known as BRL 49653, BRL 49653C, BRL 49653c, SB 210232, or rosiglitazone maleate);

(2) pioglitazone (2,4-thiazolidinedione, 5-((4-(2-(5-ethyl-2-pyridinyl)ethoxy)phenyl)methyl)-, monohydrochioride, (+−)- or 5-((4-(2-(5-ethyl-2-pyridyl)ethoxy)phenyl) methy)-2,4-thiazolidinedione, known as ACTOS, ZACTOS, or GLUSTIN; also known as AD 4833, U 72107, U 72107A, U 72107E, pioglitazone hydrochloride (USAN));

(3) troglitazone (5-((4-((3,4-dihydro-6-hydroxy-2,5,7,8-tetramethyl-2H-1-benzopyran-2-yl)methoxy)phenyl) methyl)-2,4-thiazolidinedione, known as NOSCAL, REZULIN, ROMOZIN, or PRELAY; also known as Cl 991, CS 045, GR 92132, GR 92132X);

(4) isaglitazone ((+)-5-[[6-[(2-fluorophenyl)methoxy]-2-naphthalenyl]methyl]-2,4-thiazolidinedione or 5-((6-((2-fluorophenyl)methoxy)-2-naphthalenyl)methyl-2, 4-thiazolidinedione or 5-(6-(2-fluorobenzyloxy) naphthalen-2-ylmethyl)thiazolidine-2,4-dione, also known as MCC-555 or neoglitazone); and (5) 5-BTZD.

Additionally, the non-thiazolidinediones that act as insulin sensitizing agents include, but are not limited to:

(1) JT-501 (JTT 501, PNU-1827, PNU-716-MET-0096, or PNU 182716: isoxazolidine-3,5-dione, 4-((4-(2-phenyl-5-methyl)-1,3-oxazolyl)ethylphenyl-4)methyl-);

(2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl)methyl)-2-methoxy-N-((4-(trifluoromethyl)phenyl)methyl)benzamide); and (3) Farglitazar (L-tyrosine, N-(2-benzoylphenyl)-o-(2-(5-methyl-2-phenyl-4-oxazolyl)ethyl)- or N-(2-benzoylphenyl)-O-(2-(5-methyl-2-phenyl-4-oxazolyl)-ethyl)-L-tyrosine, or GW2570 or G I-262570).

Other agents have also been shown to have PPAR modulator activity such as PPAR gamma, SPPAR gamma, and/or PPAR delta/gamma agonist activity. Examples are listed below:

(1) AD 5075;
(2) R 119702 ((+−)-5-(4-(5-Methoxy-1H-benzimidazol-2-ylmethoxy)benzyl)thiazolin-2,4-dione hydrochloride, or Cl 1037 or CS 011);
(3) CLX-0940 (peroxisome proliferator-activated receptor alpha agonist/peroxisome proliferator-activated receptor gamma agonist);
(4) LR-90 (2,5,5-tris(4-chiorophenyl)-1,3-dioxane-2-carboxylic acid, PPARdelta/γ agonist);
(5) Tularik (PPARγ agonist);
(6) CLX-0921 (PPARγ agonist);
(7) CGP-52608 (PPAR agonist);
(8) GW-409890 (PPAR agonist);
(9) GW-7845 (PPAR agonist);
(10) L-764406 (PPAR agonist);
(11) LG-101280 (PPAR agonist);
(12) LM-4156 (PPAR agonist);
(13) Risarestat (CT-112);
(14) YM 440 (PPAR agonist);
(15) AR-H049020 (PPAR agonist);
(16) GW 0072 (4-(4-((2S,5S)-5-(2-(bis(phenylmethyl) amino)-2-oxoethyl)-2-heptyl-4-oxo-3-thiazo lidinyl) butyl)benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);
(22) GW 1929 (N-(2-benzoylphenyl)-0-(2-(methyl-2-pyridinylamino)ethyl)-L-tyrosine, known as GW 2331, PPAR alpha/γ agonist);
(23) SB 219994 ((S)-4-(2-(2-benzoxazolylmethylamino) ethoxy)-alpha-(2,2,2-trifluoroethoxy)benzen epropanoic acid or 3-(4-(2(N-(2-benzoxazolyl)-N-methylamino)ethoxy)phenyl)-2 (S)-(2,2,2-trifluoroethoxy) propionic acid or benzenepropanoic acid,4-(2-(2-benzoxazolylmethylamino)ethoxy)-alpha-(2,2,2-trifluoroethoxy)(alphaS) PPARalpha/γ agonist);
(24) L-796449 (PPAR alpha/γ agonist);
(25) Fenofibrate (Propanoic acid, 2-[4-(4-chlorobenzoyl) phenoxy]-2-methyl-, 1-methylethyl ester, known as TRICOR, LIPCOR, LIPANTIL, LIPIDIL MICRO PPAR alpha agonist);
(26) GW-9578 (PPAR alpha agonist);
(27) GW-2433 (PPAR alpha/γ agonist);
(28) GW-0207 (PPARγ agonist);
(29) LG-100641 (PPARγ agonist);
(30) LY-300512 (PPARγ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and
(36) GW-1536 (PPAR alpha/y agonist).

(B) Other insulin sensitizing agents include, but are not limited to:

(1) INS-1 (D-chiro inositol or D-1,2,3,4,5,6-hexahydroxy-cyclohexane);
(2) protein tyrosine phosphatase 1 B (PTP-1B) inhibitors;
(3) glycogen synthase kinase-3 (GSK3) inhibitors;
(4) beta 3 adrenoceptor agonists such as ZD 2079 ((R)-N-(2-(4-(carboxymethyl)phenoxy)ethyl)-N-(2-hydroxy-2-phenethyl)ammonium chloride, also known as ICI D 2079) or AZ 40140;
(5) glycogen phosphorylase inhibitors;
(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;
(11) YM 268 (5,5'-methylene-bis(1,4-phenylene)bismethylenebis(thiazolidine-2,4-dione);
(12) TS 971;
(13) T 174 ((+−)-5-(2,4-dioxothiazolidin-5-ylmethyl)-2-(2-naphthylmethyl)benzoxazole);
(14) SDZ PGU 693 ((+)-trans-2 (S-((4-chlorophenoxy) methyl)-7alpha-(3,4-dichlorophenyl)tetrahydropyrrolo (2,1-b) oxazol-5(6H)-one);

(15) S 15261 ((−)-4-(2-((9H-fluoren-9-ylacetyl)amino) ethyl)benzoic acid 2-((2-methoxy-2-(3-(trifluoromethyl)phenyl)ethyl)amino)ethyl ester);
(16) AZM 134 (Alizyme);
(17) ARIAD;
(18) R 102380;
(19) PNU 140975 (1-(hydrazinoiminomethyl)hydrazino) acetic acid;
(20) PNU 106817 (2-(hydrazinoiminomethyl)hydrazino) acetic acid;
(21) NC2100 (5-((7-(phenylmethoxy)-3-quinolinyl)methyl)-2,4-thiazolidinedione;
(22) MXC3255;
(23) MBX 102;
(24) ALT 4037;
(25) AM 454;
(26) JTP 20993 (2-(4-(2-(5-methyl-2-phenyl-4-oxazolyl) ethoxy)benzyl)-malonic acid dimethyl diester);
(27) Dexlipotam (5 (R)-(1,2-dithiolan-3-yl)pentanoic acid, also known as (R)-alpha lipoic acid or (R)-thioctic acid);
(28) BM 170744 (2, 2-Dichloro-12-(p-chlorophenyl)dodecanoic acid);
(29) BM 152054 (5-(4-(2-(5-methyl-2-(2-thienyl)oxazol-4-yl)ethoxy)benzothien-7-ylmethyl)thiazolidine-2,4-dione);
(30) BM 131258 (5-(4-(2-(5-methyl-2-phenyloxazol-4-yl) ethoxy)benzothien-7-ylmethyl)thiazolidine-2,4-dione);
(31) CRE 16336 (EML 16336);
(32) HQL 975 (3-(4-(2-(5-methyl-2-phenyloxazol-4-yl) ethoxy)phenyl)-2(S)-(propylamino)propionic acid);
(33) DRF 2189 (5-((4-(2-(1-Indolyl)ethoxy)phenyl)methyl)thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors
(38) mitogen-activated protein kinase (MAPK) inhibitors p38 MAPK Stimulators
(39) phosphatidyl-inositide triphosphate
(40) insulin recycling receptor inhibitors
(41) glucose transporter 4 modulators
(42) TNF-a antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.
(C) Biguanides, which decrease liver glucose production and increases the uptake of glucose. Examples include metformin such as:

(1) 1,1-dimethylbiguanide (e.g., Metformin—DepoMed, Metformin-Biovail Corporation, or METFORMIN GR (mefformin gastric retention polymer)); and
(2) mefformin hydrochloride (N,N-dimethylimidodicarbonimidic diamide monohydrochloride, also known as LA 6023, BMS 207150, GLUCOPHAGE, or GLUCOPHAGE XR.

(D) Alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the post-prandial glucose peak. Examples include, but are not limited to:
(1) acarbose (D-glucose, O-4,6-dideoxy-4-(((1S-(1alpha, 4alpha,5beta,6alpha))-4,5,6-trihydroxy-3-(hydroxymethyl)-2-cyclohexen-1-yl)amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE);
(2) Miglitol (3,4,5-piperidinetriol, 1-(2-hydroxyethyl)-2-(hydroxymethyl)-, (2R (2alpha, 3beta, 4alpha, 5beta))- or (2R,3R,4R,5S)-1-(2-hydroxyethyl)-2-(hydroxymethyl-3,4,5-piperidinetrioi, also known as BAY 1099, BAY iNA 1099, BAY-m-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl)amino)-alpha-b-glucopyranosyl-(1-4)-alpha-D-glucopyranosyl-(1-4)-D-glucopyranose);
(4) emiglitate (4-(2-((2R,3R,4R,5S)-3,4,5-trihydroxy-2-(hydroxymethyl)-1-piperidinyl)ethoxy)benzoic acid ethyl ester, also known as BAY o 1248 or MKC542);
(5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and
(6) Voglibose (3,4-dideoxy-4-((2-hydroxy-1-(hydroxymethyl)ethyl)amino)-2-C-(hydroxymethyl)-D-epi-inositol or D-epi-Inosito1,3,4-dideoxy-4-((2-hydroxy-1-(hydroxymethyl)ethyl)amino)-2-C-(hydroxymethyl)-, also known as A 71100, AO 128, BASEN, GLUSTAT, VOGLISTAT.

(E) Insulins include regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:
(1) Biota;
(2) LP 100;
(3) (SP-5-21)-oxobis(1-pyrrolidinecarbodithioato-S,S') vanadium,
(4) insulin aspart (human insulin (28B-L-aspartic acid) or B28-Asp-insulin, also known as insulin X14, INA-X14, NOVORAPID, NOVOMIX, or NOVOLOG);
(5) insulin detemir (Human 29B-(N6-(1-oxotetradecyl)-L-lysine)-(1A-21A), (1B-29B)-Insulin or NN 304);
(6) insulin lispro ("28B-L-lysine-29B-L-proline human insulin, or Lys(B28), Pro(B29) human insulin analog, also known as lys-pro insulin, LY 275585, HUMALOG, HUMALOG MIX 75/25, or HUMALOG MIX 50/50);

(7) insulin glargine (human (A21-glycine, B31-arginine, B32-arginine) insulin HOE 901, also known as LANTUS, OPTISULIN);
(8) Insulin Zinc Suspension, extended (Ultralente), also known as HUMULIN U or ULTRALENTE;
(9) Insulin Zinc suspension (Lente), a 70% crystalline and 30% amorphous insulin suspension, also known as LENTE ILETIN II, HUMULIN L, or NOVOLIN L;
(10) HUMULIN 50/50 (50% isophane insulin and 50% insulin injection);
(11) HUMULIN 70/30 (70% isophane insulin NPH and 30% insulin injection), also known as NOVOLIN 70/30, NOVOLIN 70/30 PenFill, NOVOLIN 70/30 Prefilled;
(12) insulin isophane suspension such as NPH ILETIN II, NOVOLIN N, NOVOLIN N PenFill, NOVOLIN N Prefilled, HUMULIN N;
(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);
(14) ARIAD;
(15) LY 197535;
(16) L-783281; and
(17) TE-17411.
(F) Insulin secretion modulators such as:
(1) glucagon-like peptide-1 (GLP-1) and its mimetics;
(2) glucose-insulinotropic peptide (GIP) and its mimetics;
(3) exendin and its mimetics;
(4) dipeptyl protease (DPP or DPPIV) inhibitors such as
    (4a) DPP-728 or LAF 237 (2-pyrrolidinecarbonitrile,1-(((2-((5-cyano-2-pyridinyl)amino)ethyl)amino)acetyl), known as NVP-DPP-728, DPP-728A, LAF-237);
    (4b) P 3298 or P32/98 (di-(3N-((2S,3S)-2-amino-3-methyl-pentanoyl)-1,3-thiazolidine)fumarate);
    (4c) TSL 225 (tryptophyl-1,2,3,4-tetrahydroisoquinoline-3-carboxylic acid);
    (4d) Valine pyrrolidide(valpyr);
    (4e) 1-aminoalkylisoquinolinone-4-carboxylates and analogues thereof;
    (4f) SDZ 272-070 (1-(L-Valyl)pyrrolidine);
    (4g) TMC-2A, TMC-2B, or TMC-2C;
    (4h) Dipeptide nitriles (2-cyanopyrrolodides);
    (4i) CD26 inhibitors; and
    (4j) SDZ 274-444;
(5) glucagon antagonists such as AY-279955; and
(6) amylin agonists which include, but are not limited to, pramlintide (AC-137, Symlin, tripro-amylin or pramlintide acetate).

The present compounds may also increase insulin sensitivity with little or no increase in body weight than that found with the use of existing PPAR gamma agonists. Oral antidiabetic agents may include insulin, sulfonylureas, biguanides, meglitinides, AGI's, PPAR alpha agonists, and PPAR gamma agonists, and dual PPAR alpha/gamma agonists.

The present compounds also may increase fat and/or lipid metabolism, providing a method for losing weight, losing fat weight, lowering body mass index, lowering lipids (such as lowering triglycerides), or treating obesity or the condition of being overweight. Examples of lipid lowering agents include bile acid sequestrants, fibric acid derivatives, nicotinic acid, and HMGCoA reductase inhibitors. Specific examples include statins such as LIPITOR®, ZOCOR®, PRAVACHOL®, LESCOL®, and MEVACOR®, and pitavasiatin (nisvastatin) (Nissan, Kowa Kogyo, Sankyo, Novartis and extended release forms thereof, such as ADX-159 (extended release lovastatin), as well as Colestid, Locholest, Questran, Atromid, Lopid, and Tricor.

Examples of blood pressure lowering agents include antihypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, Imdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

F. BIOLOGICAL EXAMPLES

Transfection Assay Method for PPAR Receptors

HEK293 cells were grown in DMEM/F-12 Media supplemented with 10% FBS and glutamine (GIBCOBRL). The cells were co-transfected with DNA for PPAR-Gal4 (PPARα, γ or δ) receptor and Gal4-Luciferase Reporter using the DMRIE-C Reagent. On the following day, the medium was replaced with 5% Charcoal treated FBS growth medium. After six hours, cells were trypsinized and seeded at a density of 50,000 cell/well into 96 well plates and incubated overnight at 37° C. in a 5% $CO_2$ incubator. Cells were then treated with test compounds or vehicle and incubated for 24 hours at 37° C. in a 5% $CO_2$ incubator. Luciferase activity was assayed using the Steady-Glo Luciferase Assay Kit from Promega. DMRIE-C Reagent was purchased from GIBCO Cat. No. 10459-014. OPTI-MEM I Reduced Serum Medium was purchased from GIBCO Cat. No. 31985. Steady-Glo Luciferase Assay Kit was purchased from Promega Part# E254B.

A variety of example compounds have been made and tested, with a range of in vitro results. Below are representative compounds and data; in some cases, where multiple $EC_{50}$'s are shown, multiple measurements were taken. Naturally, different compounds in Formula (I) may have not have activities identical to any one compound below.

TABLE 2

| In Vitro Data | |
| --- | --- |
| Compound Number | $EC_{50}$ (PPAR delta) nM |
| 1 | 13.2, 18.7, 17.8, 34.1, 14.7 |
| 2 | 26.4, 27.1 |
| 3 | 711 |
| 4 | 29, 27.8 |
| 5 | 79.2, 51.8 |
| 6 | 56.6, 42.9 |
| 7 | 138 |
| 8 | >500 |
| 9 | 216 |
| 10 | 238 |
| 11 | 45.1, 48.3 |
| 12 | >1000 |
| 13 | >500 |

TABLE 2-continued

| In Vitro Data | |
|---|---|
| Compound Number | $EC_{50}$ (PPAR delta) nM |
| 14 | >1000 |
| 15 | 22.7, 22.1 |
| 16 | 87.8, 51.4 |
| 17 | 32.1, 38.7 |
| 18 | 59.1, 31.9 |
| 19 | 67.7, 49.7 |
| 20 | 194 |
| 21 | >1000 |
| 22 | 28.9, 68.3 |
| 23 | 27.8, 22.9, 19.3 |
| 24 | 9.7, 7.4 |
| 25 | 147 |
| 26 | 43.8, 47.3 |
| 27 | 119 |
| 28 | 122 |
| 29 | 249 |

G. OTHER EMBODIMENTS

The features and principles of the invention are illustrated in the discussion, examples, and claims herein. Various adaptations and modifications of the invention will be apparent to a person of ordinary skill in the art and such other embodiments are also within the scope of the invention. Publications cited herein are incorporated in their entirety by reference.

The invention claimed is:

1. A method for treating a condition selected from the group consisting of diabetes, cardiovascular diseases, Metabolic X Syndrome, hypercholesterolemia, hypo-HDL-cholesterolemia, hyper-LDL-cholesterolemia, dyslipidemia, atherosclerosis, and obesity comprising administering to a patient in need of such treatment an effective amount of a compound having the following structure

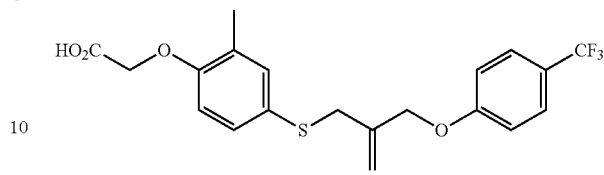

or a pharmaceutically acceptable salt thereof.

2. The method of claim 1, wherein the condition is diabetes.

3. The method of claim 1, wherein the condition is cardiovascular diseases.

4. The method of claim 1, wherein the condition is Metabolic X Syndrome.

5. The method of claim 1, wherein the condition is hypercholesterolemia.

6. The method of claim 1, wherein the condition is hypo-HDL-cholesterolemia.

7. The method of claim 1, wherein the condition is hyper-LDL-cholesterolemia.

8. The method of claim 1, wherein the condition is dyslipidemia.

9. The method of claim 1, wherein the condition is atherosclerosis.

10. The method of claim 1, wherein the condition is obesity.

* * * * *